(12) United States Patent
Townsend et al.

(10) Patent No.: US 8,574,314 B2
(45) Date of Patent: Nov. 5, 2013

(54) RESILIENT PROSTHETIC AND ORTHOTIC COMPONENTS WHICH INCORPORATE A PLURALITY OF SAGITTALLY ORIENTED STRUTS

(75) Inventors: Barry W. Townsend, Bakersfield, CA (US); Byron Kent Claudino, Bakersfield, CA (US); Monty Moshier, Washinton, UT (US); Dallin Leach, Santa Clara, UT (US)

(73) Assignee: Bioquest Prosthetics LLC, Bakersfield, CA (US)

( * ) Notice: Subject to any disclaimer, the term of this patent is extended or adjusted under 35 U.S.C. 154(b) by 289 days.

(21) Appl. No.: 12/886,758

(22) Filed: Sep. 21, 2010

(65) Prior Publication Data

US 2011/0071650 A1    Mar. 24, 2011

Related U.S. Application Data

(63) Continuation-in-part of application No. 10/594,798, filed as application No. PCT/US2005/011291 on Apr. 1, 2005, now Pat. No. 8,236,062, and a continuation-in-part of application No. 10/473,682, filed on Sep. 30, 2003, now Pat. No. 7,507,259.

(60) Provisional application No. 60/558,119, filed on Apr. 1, 2004, provisional application No. 61/277,414, filed on Sep. 24, 2009, provisional application No. 61/338,534, filed on Feb. 19, 2010, provisional application No. 61/336,375, filed on Jan. 21, 2010.

(51) Int. Cl.
*A61F 2/66* (2006.01)

(52) U.S. Cl.
USPC ............ 623/55; 623/27; 623/49; 623/52

(58) Field of Classification Search
USPC .................. 623/27, 49, 52, 55; 29/426.1
See application file for complete search history.

(56) References Cited

U.S. PATENT DOCUMENTS

| | | | |
|---|---|---|---|
| 640,540 | A | 1/1900 | Daniels |
| 810,180 | A | 1/1906 | Wintermute |
| 1,502,593 | A | 11/1923 | Shrodes |
| 2,453,969 | A | 11/1948 | Carter |
| 3,335,428 | A | 8/1967 | Gajdos |

(Continued)

FOREIGN PATENT DOCUMENTS

| | | | | |
|---|---|---|---|---|
| CA | 2103341 A1 | 4/1995 | ............. | A61F 2/66 |
| DE | 325171 C1 | 10/1920 | | |

(Continued)

OTHER PUBLICATIONS

Supplementary Partial European Search Report; EP 02 75 7836; Date : Mar. 7, 2006.

(Continued)

*Primary Examiner* — Richard Chang
(74) *Attorney, Agent, or Firm* — Antonelli, Terry, Stout & Kraus, LLP.

(57) ABSTRACT

A method of making a resilient prosthetic/orthotic component, particularly a shank for a lower extremity prosthesis in which the shank includes multiple sections which are unbounded in one or more portions of each other, and wherein the shank sections incorporate at least one voids and inserted materials between one or more shank sections to enhance shank flexibility while reducing stresses which can cause premature failure.

4 Claims, 41 Drawing Sheets

(56) References Cited

U.S. PATENT DOCUMENTS

| | | | |
|---|---|---|---|
| 4,547,913 A | 10/1985 | Phillips | |
| 4,555,817 A | 12/1985 | McKendrick | |
| 4,645,509 A | 2/1987 | Poggie et al. | 623/55 |
| 4,721,510 A | 1/1988 | Cooper et al. | |
| 4,822,363 A | 4/1989 | Phillips | |
| 4,892,554 A | 1/1990 | Robinson | |
| 4,911,724 A | 3/1990 | Fikes | |
| 4,938,776 A | 7/1990 | Masinter | |
| 4,959,073 A | 9/1990 | Merlette | |
| 4,994,086 A | 2/1991 | Edwards | |
| 5,019,109 A | 5/1991 | Voisin | |
| 5,062,859 A | 11/1991 | Naeder | |
| 5,066,305 A | 11/1991 | Firth | |
| 5,112,356 A | 5/1992 | Harris et al. | 623/49 |
| 5,116,383 A | 5/1992 | Shorter et al. | |
| 5,139,525 A | 8/1992 | Kristinsson | |
| 5,156,632 A | 10/1992 | Wellershaus | |
| 5,181,932 A | 1/1993 | Phillips | |
| 5,181,933 A | 1/1993 | Phillips | |
| 5,217,500 A | 6/1993 | Phillips | |
| 5,219,365 A | 6/1993 | Sabolich | |
| 5,258,039 A | 11/1993 | Goh et al. | |
| 5,290,319 A | 3/1994 | Phillips | |
| 5,312,669 A | 5/1994 | Bedard | |
| 5,314,499 A | 5/1994 | Collier, Jr. | 623/47 |
| 5,376,133 A | 12/1994 | Gramnas | |
| 5,376,139 A | 12/1994 | Pitkin | |
| 5,376,141 A | 12/1994 | Phillips | |
| 5,387,246 A | 2/1995 | Phillips | |
| 5,443,522 A | 8/1995 | Hiemisch | |
| 5,443,527 A | 8/1995 | Wilson | |
| 5,458,656 A | 10/1995 | Phillips | |
| 5,464,441 A * | 11/1995 | Phillips | 623/27 |
| 5,482,513 A | 1/1996 | Wilson | |
| 5,486,209 A | 1/1996 | Phillips | |
| 5,507,838 A | 4/1996 | Chen | |
| 5,509,936 A | 4/1996 | Rappoport et al. | |
| 5,509,937 A | 4/1996 | Allard et al. | |
| 5,509,938 A | 4/1996 | Phillips | |
| 5,514,185 A | 5/1996 | Phillips | |
| 5,545,230 A | 8/1996 | Kinsinger et al. | |
| 5,549,714 A | 8/1996 | Phillips | |
| 5,571,213 A | 11/1996 | Allen | |
| 5,593,456 A | 1/1997 | Merlette | |
| 5,593,457 A | 1/1997 | Phillips | |
| 5,653,767 A | 8/1997 | Allen et al. | |
| 5,653,768 A | 8/1997 | Kania | |
| 5,695,526 A | 12/1997 | Wilson | |
| 5,695,527 A | 12/1997 | Allen | |
| 5,702,488 A | 12/1997 | Wood et al. | |
| 5,725,598 A | 3/1998 | Phillips | |
| 5,728,176 A | 3/1998 | Phillips | |
| 5,728,177 A | 3/1998 | Phillips | |
| 5,746,773 A | 5/1998 | Littig | |
| 5,766,264 A | 6/1998 | Lundt | |
| 5,766,265 A | 6/1998 | Phillips | |
| 5,776,205 A | 7/1998 | Phillips | 623/55 |
| 5,800,568 A | 9/1998 | Atkinson et al. | |
| 5,800,569 A | 9/1998 | Phillips | |
| 5,824,112 A | 10/1998 | Phillips | |
| 5,897,594 A | 4/1999 | Martin et al. | |
| 5,899,944 A | 5/1999 | Phillips | |
| 5,944,760 A | 8/1999 | Christensen | |
| 5,976,191 A | 11/1999 | Phillips | |
| 5,993,488 A | 11/1999 | Phillips | |
| 6,009,572 A | 1/2000 | Morris | |
| 6,051,026 A | 4/2000 | Biedermann et al. | 623/38 |
| 6,071,313 A | 6/2000 | Phillips | |
| 6,077,301 A | 6/2000 | Pusch | |
| 6,083,265 A | 7/2000 | Shorter et al. | |
| 6,099,572 A | 8/2000 | Mosler et al. | |
| 6,187,052 B1 | 2/2001 | Molino et al. | |
| 6,197,066 B1 | 3/2001 | Gabourie | |
| 6,200,934 B1 | 3/2001 | Muller et al. | |
| 6,206,932 B1 | 3/2001 | Johnson | |
| 6,206,934 B1 | 3/2001 | Phillips | |
| 6,228,043 B1 | 5/2001 | Townsend et al. | |
| 6,241,776 B1 | 6/2001 | Christensen | |
| 6,270,468 B1 | 8/2001 | Townsend et al. | |
| 6,280,479 B1 | 8/2001 | Phillips | |
| 6,290,730 B1 | 9/2001 | Pitkin et al. | |
| 6,350,286 B1 | 2/2002 | Atkinson et al. | |
| 6,402,790 B1 | 6/2002 | Celebi | |
| 6,406,500 B1 | 6/2002 | Phillips | |
| 6,443,995 B1 | 9/2002 | Townsend et al. | |
| 6,514,293 B1 | 2/2003 | Jang et al. | |
| 6,527,811 B1 | 3/2003 | Phillips | |
| 6,562,075 B2 | 5/2003 | Townsend et al. | |
| 6,602,295 B1 | 8/2003 | Doddroe et al. | |
| 6,663,673 B2 | 12/2003 | Christensen | |
| 6,669,737 B2 | 12/2003 | Mosler et al. | |
| 7,108,723 B2 | 9/2006 | Townsend et al. | |
| 7,172,630 B2 | 2/2007 | Christensen | |
| 7,226,485 B2 | 6/2007 | Townsend et al. | |
| 7,341,603 B2 | 3/2008 | Christensen | |
| 7,374,578 B2 | 5/2008 | Townsend et al. | |
| 7,410,503 B2 | 8/2008 | Townsend et al. | |
| 1,429,272 A1 | 9/2008 | Townsend et al. | |
| 7,507,259 B2 | 3/2009 | Townsend et al. | |
| 7,578,852 B2 | 8/2009 | Townsend et al. | |
| 2002/0040249 A1 | 4/2002 | Phillips | |
| 2002/0077706 A1 | 6/2002 | Phillips | |
| 2002/0087216 A1 | 7/2002 | Atkinson et al. | |
| 2002/0116072 A1 | 8/2002 | Rubie et al. | |
| 2002/0133237 A1 | 9/2002 | Christensen | |
| 2003/0009238 A1 | 1/2003 | Whayne | |
| 2003/0028256 A1 | 2/2003 | Townsend et al. | |
| 2003/0045944 A1 | 3/2003 | Mosler et al. | |
| 2003/0093158 A1 | 5/2003 | Phillips et al. | |
| 2003/0120354 A1 | 6/2003 | Doddroe et al. | |
| 2003/0191540 A1 | 10/2003 | Townsend et al. | |
| 2004/0209716 A1 | 10/2004 | Vacek et al. | |
| 2007/0213841 A1 | 9/2007 | Townsend et al. | |

FOREIGN PATENT DOCUMENTS

| | | | |
|---|---|---|---|
| DE | 1971298 C1 | 5/1998 | |
| DE | 298 20 904 U1 | 6/1999 | |
| DE | 298 23 435 U1 | 9/1999 | |
| DE | 29920434 U1 | 5/2002 | |
| DK | EP 0 648 479 A1 | 10/1993 | |
| EP | 0 331 468 | 9/1989 | |
| EP | 0 648 479 A1 | 4/1995 | |
| EP | 0793949 A1 | 9/1997 | |
| FR | 2 640 499 A1 | 6/1990 | A61F 2/66 |
| FR | 2 734 151 | 11/1996 | |
| FR | 2734151 | 11/1996 | |
| GB | 2 173 569 | 10/1986 | |
| JP | 9-327473 | 12/1997 | |
| JP | 11-299815 | 11/1999 | |
| WO | WO 91/00070 | 1/1991 | A61F 2/66 |
| WO | WO 9410942 A1 | 5/1994 | |
| WO | WO 97/17042 | 5/1997 | |
| WO | WO 00/71061 A1 | 11/2000 | |
| WO | WO 02/02034 A1 | 1/2002 | |
| WO | WO 02/30340 | 4/2002 | |
| WO | WO 2005/097008 | 10/2005 | |

OTHER PUBLICATIONS

Supplementary Partial European Search Report; EP 02 71 3785; Date : Mar. 7, 2006.

International Search Report; PCT/US05/34037; Filing Date: Sep. 26, 2005.

International Search Report (Jul. 1998); International application No. PCT/US01/48954.

International Search Report (Jul. 1998); International application No. PCT/US02/09589.

International Search Report (Apr. 2002); International application No. PCT/US02/09573.

International Search Report (Apr. 2002); International application No. PCT/US02/09571.

(56) References Cited

OTHER PUBLICATIONS

International Search Report (Jul. 1998); International application No. PCT/US02/30471.
PCT Written Opinion from International Application No. PCT/US02/06901.
Supplementary European Search Report; EP 02 71 3785; May 22, 2006.
Supplementary European Search Report; EP 02 75 7836; May 25, 2006.
International Search Report; PCT/US03/09506; filed Mar. 31, 2003.
Universal Offset Pyramid Adapters; 2 pages.
International Search Report; PCT/US05/11304; Filing Date: Apr. 1, 2005.
International Search Report; PCT/US05/11291; Filing Date: Apr. 1, 2005.
Canadian Office Action dated Feb. 16, 2009, Application No. 2,446,768; 3 pages; Owner: Barry W. Townsend, et al.; Title: Prosthetic Foot With Tunable Performance.
European Office Action dated Apr. 3, 2009 ; Application No. 02 733 905.0-2310 ; 4 pages ; Applicant : Barry W. Townsend, et al.
International Search Report dated Jul. 30, 2002, from International Application No. PCT/US02/06901.
International Search Report/Written Opinion, PCT/US2011/052475, Jan. 20, 2012.
International Preliminary Report on Patentability, PCT/US2011/052475 (Nov. 15, 2012).

* cited by examiner

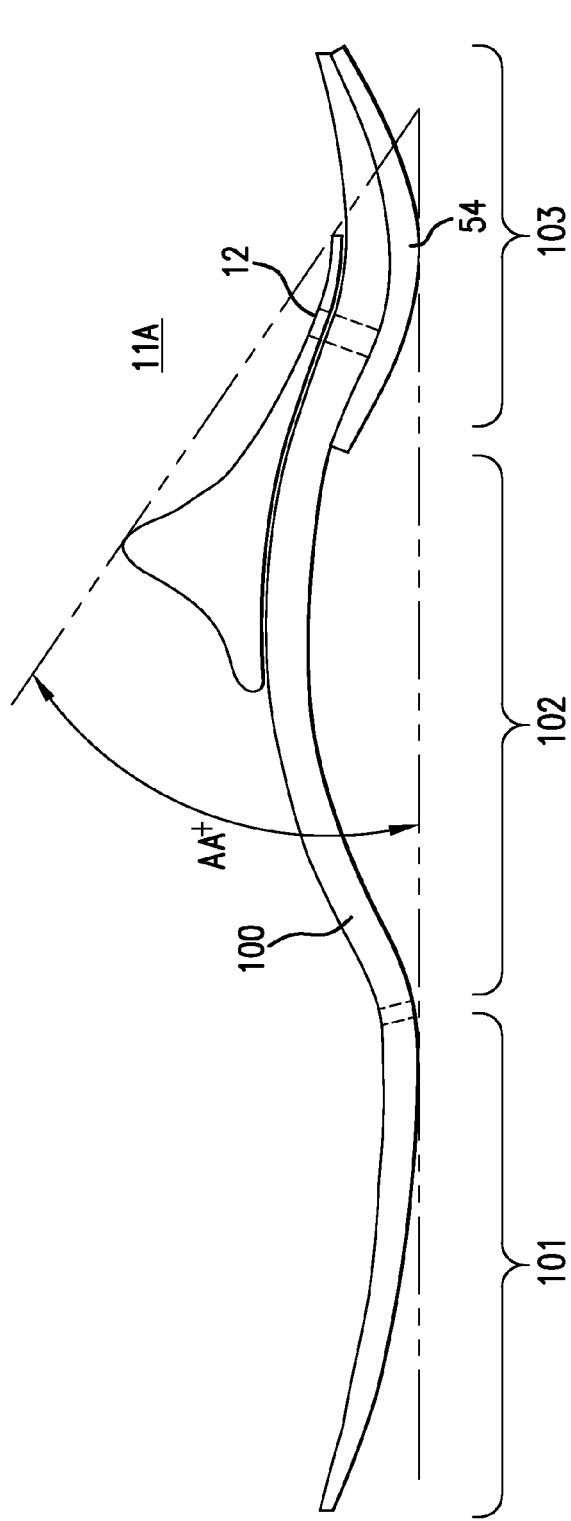
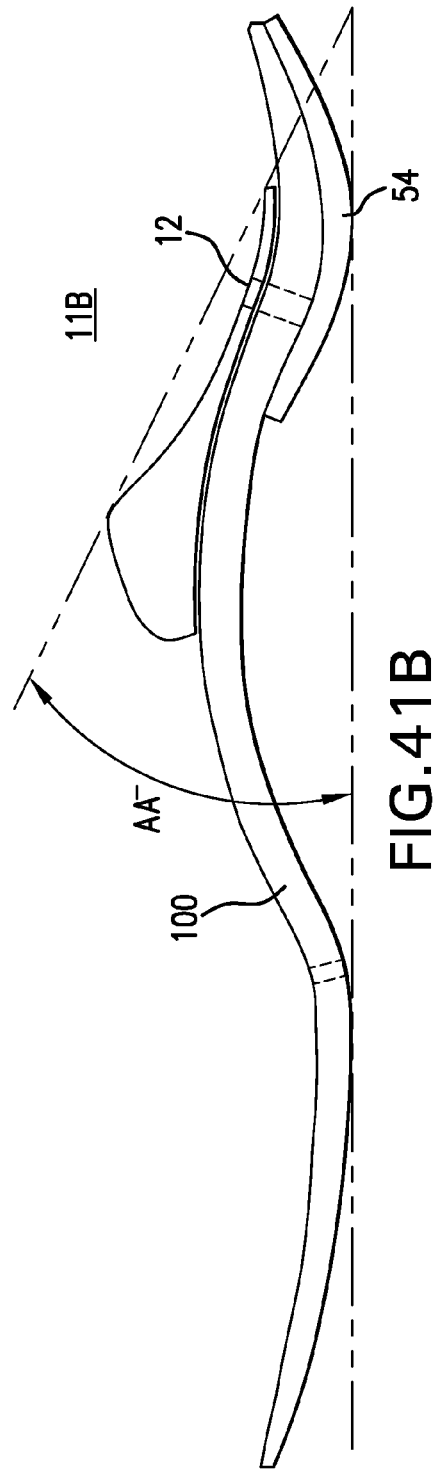
FIG. 41A
FIG. 41B

RESILIENT PROSTHETIC AND ORTHOTIC COMPONENTS WHICH INCORPORATE A PLURALITY OF SAGITTALLY ORIENTED STRUTS

RELATED APPLICATIONS

This application is a continuation in part of application Ser. No. 10/594,798 filed Sep. 29, 2006, now U.S. Pat. No. 8,236, 062 issued Aug. 7, 2012, as the U.S. national phase under 35 U.S.C. 371 of international application no. PCT/US2005/011291 filed Apr. 1, 2005 which is a continuation in part of U.S. application Ser. No. 10/814,260 filed Apr. 1, 2004, now U.S. Pat. No. 7,611,543 issued Nov. 3, 2009, and which claims priority of U.S. provisional application Ser. No. 60/558,119 filed Apr. 1, 2004, and which is a continuation in part of U.S. application Ser. No. 10/814, 155 filed Apr. 1, 2004, now U.S. Pat. No. 7,410,503 issued Aug. 12, 2008, and which application Ser. No. 10/594,798 is also a continuation in part of U.S. application Ser. No. 10/473, 682 filed Mar. 29, 2002, now U.S. Pat. No. 7,507,259 issued Mar. 24, 2009. application Ser. No. 12/886,758 also claims priority of U.S. provisional applications Nos. 61/277,414 filed Sep. 24, 2009, 61/336,375 filed Jan. 21, 2010 and 61/338,534 filed Feb. 19, 2010. The disclosures of these prior applications and provisional applications are hereby incorporated by reference.

TECHNICAL FIELD

The present invention relates to resilient prosthetic and orthotic components providing improved dynamic response as these capabilities relate to applied force mechanics and, more particularly, to an improved lower extremity prosthesis and to a method of manufacturing the same.

BACKGROUND

A jointless artificial foot prosthesis is disclosed by Martin et al. in U.S. Pat. No. 5,897,594. Unlike earlier solutions wherein the artificial foot has a rigid construction provided with a mechanical joint hinge in order to imitate the function of the ankle, the jointless artificial foot of Martin et al. employs a resilient foot insert which is arranged inside a foot molding. The insert is of approximately C-shaped design in longitudinal section, with the opening to the rear, and takes up the prosthesis load with its upper C-limb and via its lower C-limb transmits that load to a leaf spring connected thereto. The leaf spring as seen from the underside is of convex design and extends approximately parallel to the sole region, forward beyond the foot insert into the foot toe-tip region. The Martin et al. invention is based on the object of improving the jointless artificial foot with regard to damping the impact of the heel, the elasticity, the heel-to-toe walking and the lateral stability, in order thus to permit the wearer to walk in a natural manner, the intention being to allow the wearer both to walk normally and also to carry out physical exercise and to play sports. Other similar designs, such as, U.S. Pat. Nos. 6,077, 301; 6,669,737 B2; and 6,009,572; and German Patent No DE 299 20 434 U1, have been introduced. Additionally the upper branch of the C-limb is horizontally oriented whereby a prosthetic leg/shank is attached there to. This horizontally oriented upper branch responds to a ground reaction force created in amputee gait by displacing in a proximal and distal direction and not in a substantially anterior/posterior direction. This proximal and distal displacement accomplishes their claimed damping the impact of the heel. The c-shaped foot insert proximal and distal horizontally oriented branches are made rigid with respect to moments. The proximal branch rigidity is derived by a rigid metal coupling element connected to the proximal surface of this branch. This rigid coupling element provides a coupling means for a prosthetic leg/shank element to be coupled thereto. The distal branch rigidity is derived by being attached to a proximal surface of the aforesaid distal leaf spring. The functional deficiency of this design is related to the fact it is a foot insert for an artificial foot wherein the c-shaped spring is configured specifically for a foot. In contrast a human foot is defined as being made up of 25 bones and these bones are distal to a leg/shank. The human leg/shank is a weight bearing longitudinally oriented structure. The human shank is surrounded proximally by muscles wherein these muscles terminate distally as tendons. In gait, these tendons function as mechanical springs. The tendon insertions are located on several of the foot bones. These tendon insertions work in concentration with the human ankle joint to direct closed kinetic chain ankle motion. A prosthetic resilient insert configured for an artificial foot does not include a prosthetic resilient leg/shank element of sufficient length to replicate human calf musculature biomechanical function.

A resilient prosthetic leg/shank which is substantially vertically oriented, which includes a plurality of sagittally oriented struts which are anterior facing convexly curved at their lower ends, whereby they are attached to a prosthetic foot replicates human shank with muscle and ankle function more accurately than a resilient foot insert configured for a prosthetic foot. Therefore, the dynamic response characteristics of these known artificial feet are limited. There is a need for a higher performance prosthetic foot having improved applied mechanics design features which can improve amputee athletic performances involving activities such as running, jumping, sprinting, starting, stopping and cutting, for example.

Other prosthetic feet have been proposed by Van L. Phillips which allegedly provide an amputee with an agility and mobility to engage in a wide variety of activities which were precluded in the past because of the structural limitations and corresponding performances of prior art prostheses. Running, jumping and other activities are allegedly sustained by these known feet which, reportedly, may be utilized in the same manner as the normal foot of the wearer. See U.S. Pat. Nos. 6,071,313; 5,993,488; 5,899,944; 5,800,569; 5,800,568; 5,728,177; 5,728,176; 5,824,112; 5,593,457; 5,514,185; 5,181,932; 4,822,363; 5,217,500; 5,464,441; 5,725,598; and 4,547,913 for example. The dynamic response deficiencies of these known designs relate to leg/shank and foot elements being substantially vertically oriented at their lower end and or utilizing a posterior facing convexly curved ankle area.

Prosthetic design is dynamic, owing, in part, to: the perennial aspiration of creating more comfortable, versatile, or niche products; increased understanding of human anatomy and biomechanics; and recent innovations in designs and materials. One example of recent innovations in design is assignee's anterior facing convexly curved calf shank which has been proven to improve prosthetic dynamics when used in connection with specific foot keel configurations and other components. This anterior facing convexly curved calf shank/leg is disclosed in commonly owned U.S. Pat. Nos. 6,562, 075; 7,507,259; 7,429,272; 7,410,503; 7,578,852; and 7,374, 578, for example.

However, it is noted that the current existing designs and materials still have significant drawbacks which may be improved upon. More particularly, many existing designs gratuitously incorporate metal or other components which whether individually, or in combination with the overall devices, fail to optimize life expectancy and weight. Metal components are known to wear and lose strength characteristics over time. Furthermore, metal components add to the weight of the prostheses, generally an undesirable characteristic. Other advantageous properties are foregone through emphasis on use of metal components in foot prostheses.

Lighter weight materials provide many advantages when incorporated into prostheses. Carbon fiber, as merely one example, combines a high strength-to-weight ratio with low thermal expansion. Although many prostheses may use a combination of lighter weight materials such as carbon fiber in connection with other metal components, the current art fails to optimize the use of lighter weight materials due to lack of innovation of the underlying design structures compatible with the materials.

One example of how lack of innovation of underlying design structures limits the use of lighter weight materials is evident from the lack of use of the carbon fiber materials in the anterior facing convexly curved and other such calf shank configurations. More specifically, the use of carbon fiber materials to create such shanks and associated foot keels results in inter-laminate shear stresses which split layers of carbon fiber, resulting in partial or complete failure of the resilient component.

Accordingly, there is a lack of innovation with respect to foot prosthetics that would allow for optimization of the use of lighter weight materials, particularly in the shank and foot keel, while maintaining and improving upon other developments and structures in the prosthetic and orthotic industries.

Summary

In order to allow the amputees to attain a higher level of performance, there is a need for a high function prosthetic foot/lower extremity prosthesis having improved applied mechanics, a foot which may out perform the human foot and also out perform the prior art prosthetic feet. It is of interest to the amputee to have a high performance prosthetic foot having improved applied mechanics, high low dynamic response, and alignment adjustability that can be fine tuned to improve the horizontal and vertical components of activities which can be task specific in nature.

The improved lower extremity prosthesis/prosthetic foot of the present invention addresses these needs. According to an example embodiment disclosed herein, the prosthetic foot of the invention comprises a longitudinally extending foot keel having a forefoot portion at one end, a hindfoot portion at an opposite end and a relatively long midfoot portion extending between and upwardly arched from the forefoot and hindfoot portions. A calf shank including an anterior facing convexly curved lower portion is also provided. An optional adjustable fastening arrangement attaches the curved lower end of the calf shank to a posterior aspect of the upwardly arched midfoot portion of the foot keel to form an ankle joint area of the prosthetic foot.

The optional adjustable fastening arrangement permits adjustment of the alignment of the calf shank and the foot keel with respect to one another in the longitudinal direction of the foot keel for tuning the performance of the prosthetic foot. By adjusting the alignment of the opposed upwardly arched midfoot portion of the foot keel and the anterior facing convexly curved lower portion of the calf shank with respect to one another in the longitudinal direction of the foot keel, the dynamic response characteristics and motion outcomes of the foot are changed to be task specific in relation to the needed/desired horizontal and vertical linear velocities. A multi-use prosthetic foot is disclosed having high and low dynamic response capabilities, as well as triplaner motion characteristics, which improve the functional outcomes of amputees participating in sporting and/or recreational activities. A prosthetic foot especially for sprinting is also disclosed.

The calf shank in several embodiments has its lower end reversely curved in the form of a spiral with the calf shank extending upward anteriorly from the spiral to an upstanding upper end thereof. This creates a calf shank with an integrated ankle at the lower end thereof, when the calf shank is secured to the foot keel, it creates a variable radii response outcome similar to a parabola-shaped calf shank of the invention. The calf shank with spiral lower end is secured to the foot keel by way of a coupling element. In several disclosed embodiments the coupling element includes a riser/stop to limit/resist dorsiflexion of the calf shank in gait. According to a feature of several embodiments the coupling element is monolithically formed with the forefoot portion of the foot keel. According to one embodiment the coupling element extends posteriorly as a cantilever over the midfoot portion and part of the hindfoot portion of the foot keel where it is reversely curved upward to form an anterior facing concavity in which the lower end of the calf shank is housed. The reversely curved lower end of the calf shank is supported at its end from the coupling element. The resulting prosthesis has improved efficiency. A posterior calf device employing one or a plurality of springs is provided on the prosthesis according to an additional feature of the invention. The posterior calf device can be formed separately from the calf shank and connected there to or the device and calf shank can be monolithically formed. The device and shank store energy during force loading and return stored energy during force unloading for increasing the kinetic power generated for propulsive force by the prosthesis in gait. Furthermore, the resilient foot keels and calf shanks/legs in the disclosed embodiments could also be provided with a plurality of sagittally oriented sections/struts thereby creating a resilient member comprising: a lower portion; a middle portion; an upper portion; wherein said member incorporates at least a plurality of sagittally oriented resilient sections/struts, with at least a gap between said sections, said sections being anterior facing convexly curved in said lower portion, said middle portion arising from said lower portion, said upper portion arising from said middle portion and said upper portion incorporating a leg attachment/adapter allowing said member to be attached to a component worn by an amputee, said upper and middle portions being substantially vertically oriented, whereby in response to midstance to late midstance gait force at least said middle portion of said member deflects in a longitudinal direction for storing energy, thereby causing said leg attachment/adapter to be displaced in said longitudinal direction.

Moreover this new resilient shank/leg multi-strutted member provides a longer life expectancy and decreased weight. The use of carbon fiber material in the aforementioned member which includes an intermediate gap between adjacent sections/struts solves the problem with interlaminate shear stresses (which split the layers of traditional carbon fiber members) by allowing the individual shank/leg sections/struts of the shank to extend during expansion loading without interlaminate shear failure. This expansion loading occurs from midstance to late midstance phase of amputee gait. Specifically, in one embodiment voids or spaces are formed in the resilient shank by removing lengths of material intermediate the ends of the shank to form the spaces between the sections. The resulting shank structure facilitates compression and expansion of the member as the sections/struts flex toward or expand away from each other giving more desirable overall flex characteristics.

Three different types of voids or spaces maybe combined to facilitate shank/leg motion. Two types are created by removing a proximal portion of a section/strut between two adjacent sagittally oriented sections/struts. Another gap type is created by removing a portion of a single section/strut intermediate its proximal and distal ends. In several embodiments of a foot keel, an ankle, a coupling element, and a shank/leg maybe bifurcated by at least a longitudinally extending slot. This bifurcation creates an unbounded portion along its longitudinal extent thereby creating a plurality of longitudinal elements. No spacer elements, per se, are provided between the respective sections/struts of the multiple shank sections of the shank/leg although various materials may be provided between sections to facilitate independent movement thereof during expansion and compression. For example, Teflon, silicone grease, or another friction reducing substance may be added between sections. Similarly, silicone rubber or any number of other soft materials may be added between or among sections of the shank. Several types of bifurcated products can each be provided with either a taller or a shorter version of the shank. A novel method of manufacturing monolithically formed, resilient prosthetic and orthotic components with multiple shank sections is disclosed more fully hereinafter. A method of utilizing a release film between selected sections of the component is also disclosed wherein the release film creates a separating barrier during manufacture and use so that adjacent sections/struts do not mechanically bond together.

The orthotics industry is in need of a resilient ankle joint which replicates the biomechanical function of the calf shank's anterior and posterior muscles. The dynamic response, i.e. energy storing and release, capabilities of current technology is extremely limited because the resilient spring mass is so small it is dysfunctional. The need exists for a higher functioning orthotic ankle joint which is functionally superior. The present invention addresses this need with the improved resilient, multi-section; multi-strut ankle joint of the invention which includes the same applied mechanics as the prosthetic calf shank/leg member as disclosed herein.

These and other objects, features and advantages of the present invention will become more apparent from a consideration of the following detailed description of disclosed example embodiments of the invention and the accompanying drawings.

BRIEF DESCRIPTION OF THE DRAWINGS

FIGS. 41A and B is a side view of the two resilient foot keels with hindfoot pads and two different thicknesses of coupling elements/risers.

DETAILED DESCRIPTION

Figure 3:
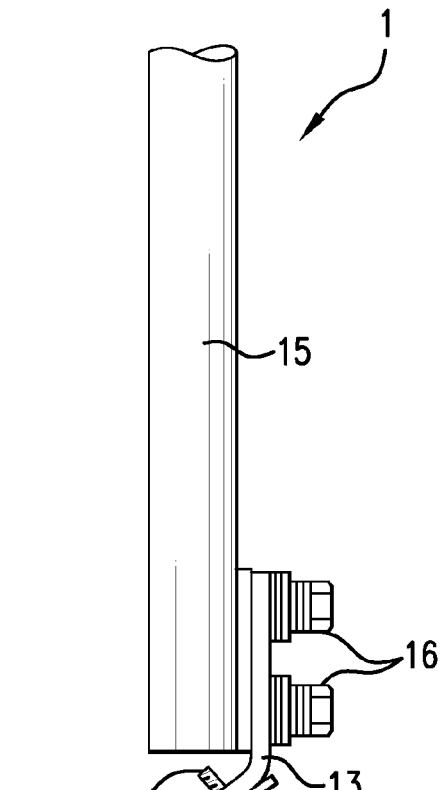
FIG. 3 is a side view of a prosthetic foot according to an example embodiment of the invention with pylori adapter/leg attachment and pylori connected thereto for securing the foot to the lower leg of an amputee.
Figure 3:
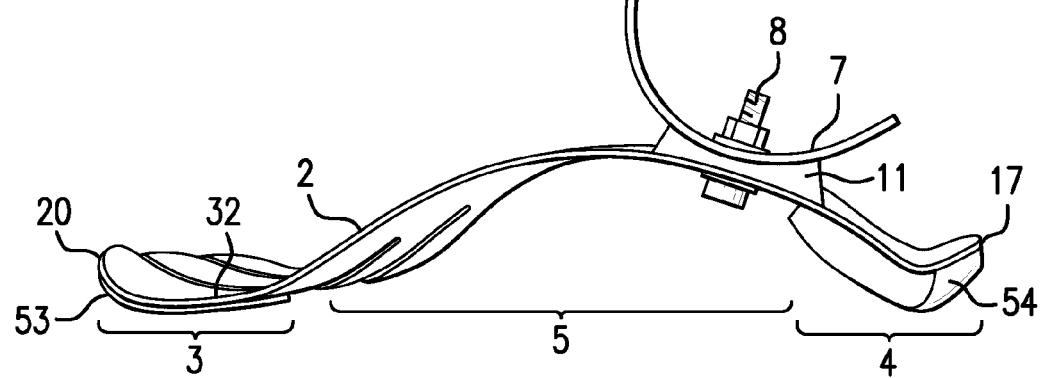
Figure 4:
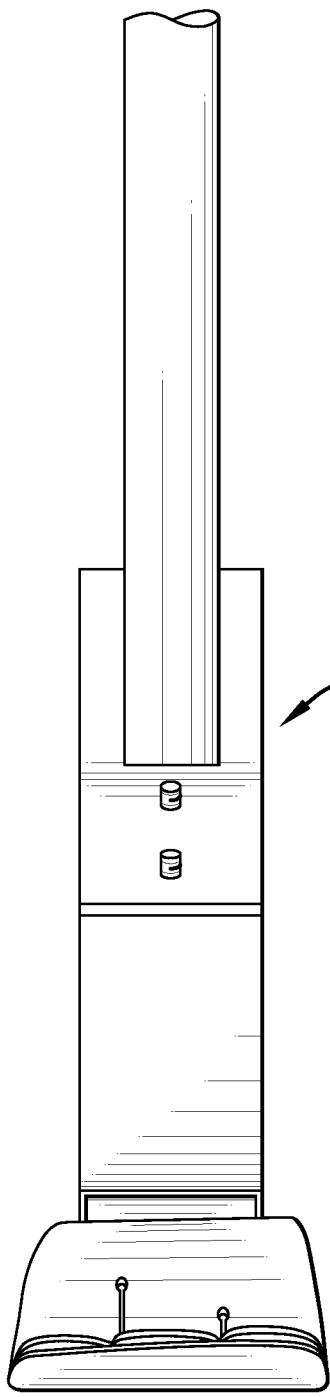
FIG. 4 is a front view of the prosthetic foot with pylori adapter and pylori of FIG. 3.
Figure 5:
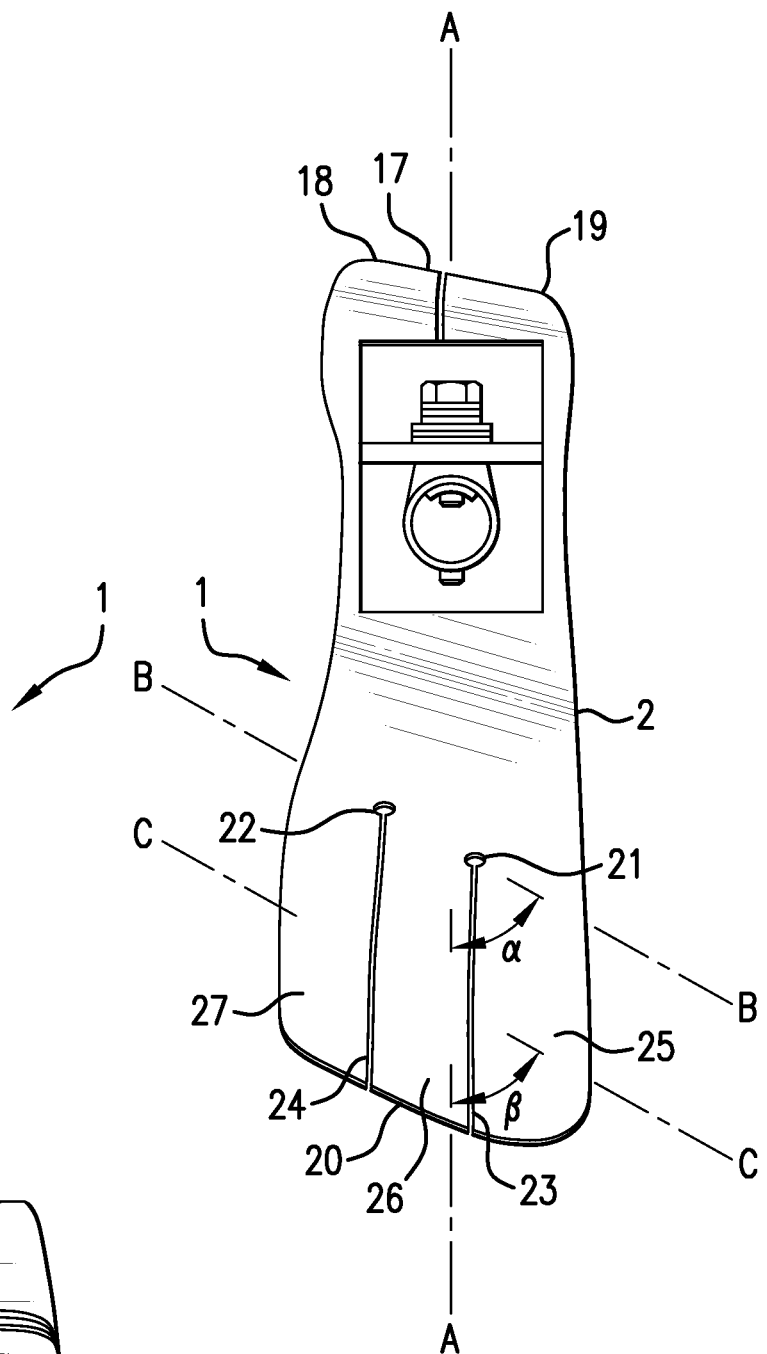
FIG. 5 is a top view of the embodiment of FIGS. 3 and 4.

Referring now to the drawings, a prosthetic foot 1 in the example embodiment of FIGS. 3-5 is seen to comprise a longitudinally extending foot keel 2 having a forefoot portion 3 at one end, a hindfoot portion 4 at an opposite end and an upwardly arched midfoot portion 5 extending between the forefoot and hindfoot portions. The midfoot portion 5 is upward convexly curved over its entire longitudinal extent between the forefoot and hindfoot portions in the example embodiment.

An upstanding calf shank/leg member 6 of the foot 1 is attached at a portion of a downward convexly curved lower end 7 thereof to a proximate, posterior surface of the keel midfoot portion by way of a releasable fastener 8 and coupling element 11. The fastener 8 is a single bolt with nut and washers in the example embodiment, but could be a releasable clamp or other fastener for securely positioning and retaining the calf shank on the foot keel when the fastener is tightened.

Figure 8:
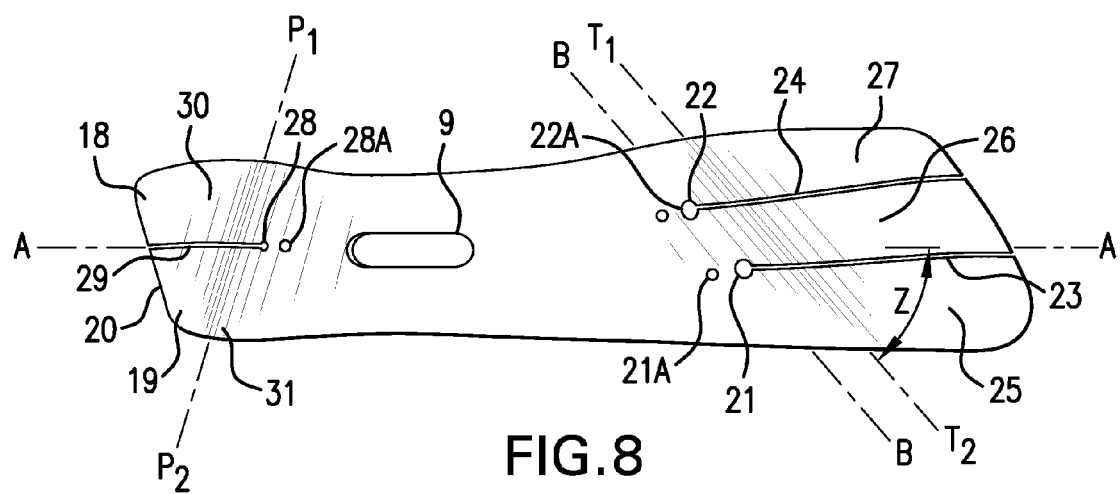
FIG. 8 is a bottom view of the foot keel in the prosthetic foot in FIG. 3 which provides high low dynamic response characteristics as well as biplaner motion capabilities.
Figure 15:
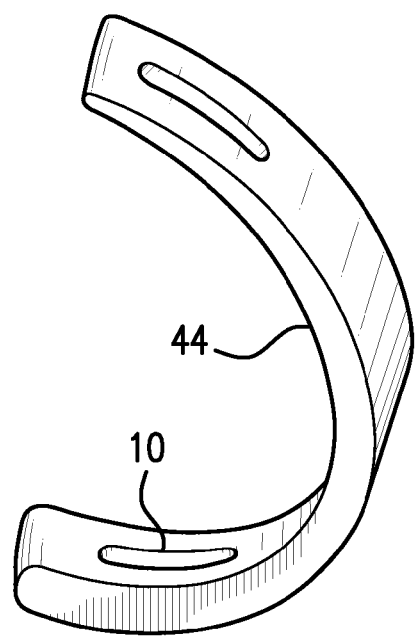
FIG. 15 is a side view from slightly above and to the front of a parabola shaped calf shank of the prosthetic foot of the invention, the thickness of the calf shank tapering toward its upper end.

A hole 9 or, preferably a longitudinally extending opening is formed in a proximate, posterior surface of the keel midfoot portion 5, see FIG. 8. A longitudinally extending opening 10 is also formed in the curved lower end 7 of the calf shank 6 like that shown in FIG. 15, for example. The releasable fastener 8 extends through the openings 9 and 10 which permit adjusting the alignment of the calf shank and the foot keel with respect to one another in the longitudinal direction, A-A in FIG. 5, when the fastener 8 is loosened or released for tuning the performance of the prosthetic foot 10 to be task specific. Thus, the fastener 8, coupling element 11 and longitudinally extending openings 9 and 10 constitute an adjustable fastening arrangement for attaching the calf shank to the foot keel to form an ankle joint area of the prosthetic foot. However, the skilled artisan will recognize the fastening arrangement need not be adjustable and that a hole for the fastener need not be a longitudinally extending opening.

Figure 1:
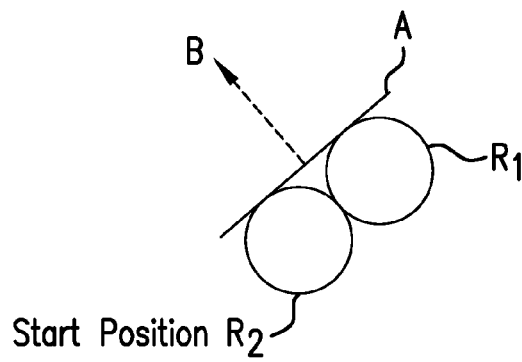
FIG. 1 is a schematic illustration representing the two adjacent radii of curvatures R1 and R2, one against the other, of a foot keel and calf shank of a prosthetic foot of the invention which creates a dynamic response capability and motion outcome of the foot in gait in the direction of arrow B which is perpendicular to the tangential line A connecting the two radii.
Figure 2:
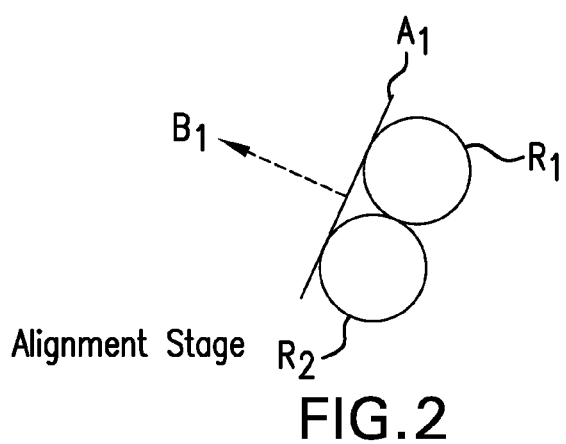
FIG. 2 is a view similar to FIG. 1 but showing the alignment of the two radii having been changed in the prosthetic foot according to the invention to increase the horizontal component and decrease the vertical component of the dynamic response capability and motion outcome of the foot in gait so that arrow B1, perpendicular to tangential line A1, is more horizontally directed than is the case depicted in FIG. 1.

The effects of adjusting the alignment of the calf shank 6 and foot keel 2 are seen from a consideration of FIGS. 1 and 2, wherein the two radii R1 and R2, one next to another, represent the adjacent, facing, domed or convexly curved surfaces of the foot keel midportion 5 and the calf shank 6. When two such radii are considered one next to another, motion capability exists perpendicular to a tangential line, A in FIG. 1, A1 in FIG. 2, drawn between the two radii. The interrelationship between these two radii determines a direction of motion outcomes. As a consequence, dynamic response force application of the foot 1 is dependent on this relationship. The larger the radius, the more dynamic response capability. However, the tighter a radius, the quicker it responds.

The alignment capability of the calf shank and foot keel in the prosthetic foot of the invention allows the radii to be shifted so that horizontal or vertical linear velocities with the foot in athletic activities are affected. For example, to improve the horizontal linear velocity capability of the prosthetic foot 1, an alignment change can be made to affect the relationship of the calf shank's radius and the foot keel radius. That is, to improve the horizontal linear velocity characteristic, the bottom radius R2, of the foot keel, is made more distal than its start position, FIG. 2 as compared with FIG. 1. This changes the dynamic response characteristics and motion outcomes of the foot 1 to be more horizontally directed and as a result greater horizontal linear velocity can be achieved with the same applied forces.

Figure 23:
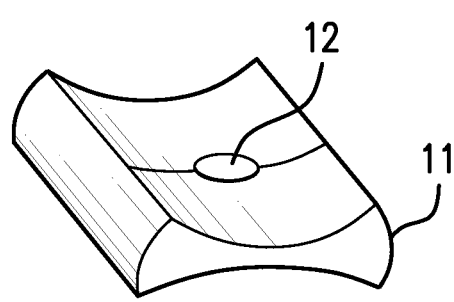
FIG. 23 is a side view, from slightly above, of a metal alloy, plastic, or composite coupling element used in the optional adjustable fastening arrangement of the invention for attaching the calf shank to the foot keel as shown in FIG. 3.
Figure 24:
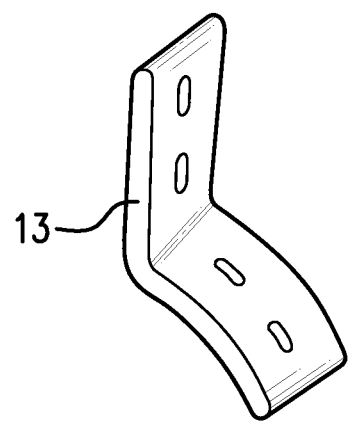
FIG. 24 is a view from the side and slightly to the front of a pylori adapter/leg attachment used on the prosthetic foot of FIGS. 3-5, and also useful with the foot of FIGS. 28 and 29, for connecting the foot to a pylori to be attached to an amputee's leg.

The amputee can, through practice, find a setting for each activity that meets his/her needs as these needs relate to horizontal and vertical linear velocities. A jumper and a basketball player, for example, need more vertical lift than a sprint runner. The coupling element 11 is a plastic, a composite or metal alloy alignment coupling element (see FIGS. 3, 4, 23 and 41A&B) sandwiched between the attached foot keel 2 and calf shank 6. The releasable fastener 8 extends through a hole 12 in the coupling element. The coupling element extends along the attached portion of the calf shank and the proximate, posterior aspect of the keel midfoot portion 5. The coupling element 11 in FIG. 41 is similar to coupling element 11 in FIGS. 3, 4, and 23. However, the coupling element 11A and 11B in FIG. 41 has an anterior riser portion of different thickness. The different thicknesses change the longitudinal alignment characteristics of the calf/shank/leg member to the foot keel. This difference in longitudinal alignment is shown by an acute angle "AA" wherein a thicker anterior riser portion as shown FIG. 41 11A has a larger/greater acute angle AA+, in comparison to a smaller riser portion 11B having an acute angle AA−. Varying the thickness of the riser portion permits accommodating different shoe heel heights with, for example, a thicker riser portion 11A accommodating ⅝ to 1¼ inch heel height shoes, and a thinner riser portion 11B accommodating flats zero to ⅝ inch heel heights.

Figure 30:
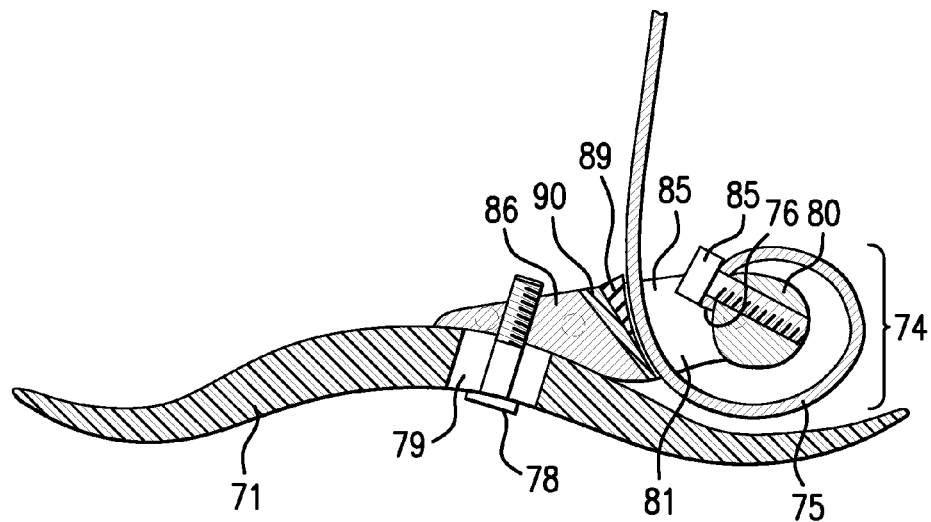
FIG. 30 is a cross-sectional view of the prosthetic foot of FIGS. 28 and 29 taken along the line 30-30 in FIG. 29.
Figure 31A:
FIGS. 31A and 31B are sectional views of wedges of different thicknesses which may be used in the dorsiflexion stop of the coupling element as shown in FIG. 30.
Figure 31B:
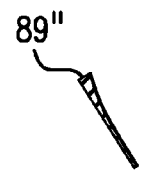

The monolithically formed resilient shank/leg member with multiple sections or struts as disclosed herein has a resistance to muscle induced plantarflexion moment in midstance to late midstance phase of amputee gait which is enhanced by coupling elements shown in FIGS. 30 (89); 31A (89); 31B (89); 32 (113); 41 (11A, 11B); 47B (11); 47C (11); 48A (11); 48B (11); 48C (11); 49 (11); 50 (11); 51 (11); and 52 (11); 58 (11); 61A (11); 61B (11); and 62 (11). These coupling elements include a dorsiflexion limiting riser portion. In the mid to late midstance phase of gait the distal anterior surface of the shank/leg member engages the riser portion anterior proximal surface which has a net effect of increasing the plantarflexion muscle moment.

With references to the embodiment of FIG. 3, the curved lower end 7 of the calf shank 6 is in the shape of a parabola with the smallest radius of curvature of the parabola located at the lower end and extending upwardly and initially anteriorly in the parabola shape. A posteriorly facing concavity is formed by the curvature of the calf shank as depicted in FIG. 3. The parabola shape is advantageous in that it has increased dynamic response characteristics in creating both improved horizontal linear velocity associated with the relatively larger radii proximal terminal end thereof, while having a smaller radius of curvature at its lower end for quicker response characteristics. The larger radii of curvature at the upper end of the parabola shape enable the tangential line A, explained with reference to FIGS. 1 and 2, to remain more vertically oriented with changes in alignment, which creates improved horizontal linear velocity.

The parabolic shaped calf shank responds to initial contact ground forces in human gait by compressing or coiling in on itself. This makes the radii of the parabola curve smaller, and as a consequence, the resistance to compression is decreased. In contrast, as the parabolic shaped calf shank responds to heel off ground reaction force (GRF) in human gait by expanding, this makes the radii of the parabola curve larger and as a consequence resistance is much greater than the aforementioned compressive resistance. These resistances are associated with the human's anterior and posterior calf muscle function in human gait. At initial contact to foot flat of human gait, the smaller anterior calf muscle group responds to GRF by eccentrically contracting to lower the foot to the ground and a muscle dorsiflexion moment is created. From foot flat to toe off the larger posterior calf muscle group responds to GRF also by eccentrically contracting and a greater muscle plantar flexion moment is created. This moment size relates to the calf anterior and posterior muscle group difference in size. As a consequence, the prosthetic calf shank's resistance to the muscle dorsiflexion and plantar flexion moments in human gait are mimicked and normal gait is achieved. The parabolic shaped shank's variable resistance capability mimics the human calf musculature function in human gait and running and jumping activities, and as a consequence prosthetic efficiency is achieved.

The parabolic shaped calf shank angular velocity is affected by the aforementioned compression and expansion modes of operation. As the parabolic shaped calf shank expands in response to late mid-stance forces, the size of the radii which make up the contour of the shank become larger. This increase in radii size has a direct relationship to an increase in angular velocity. The mathematical formula for ankle joint sagittal plane kinetic power, KP, of the prosthesis is KP=moment×angular velocity. Therefore, any increase in the mechanical form's angular velocity will increase the kinetic power. For example, the calf shanks of FIGS. 19-22, each have a portion above the anterior facing convexly curved lower portion thereof which is reversely curved, i.e. posterior facing convexly curved. If these shank's mechanical forms where made with the same materials with the same widths and thicknesses, the reversely curved upper portion would compress as the lower portion of the shank would expand— canceling the potential for an increase in angular velocity, and as a consequence, the angular velocity would be negatively affected which in turn would negatively affect the magnitude of ankle joint sagittal plane kinetic power which is generated in gait.

The human utilizes the conservation of energy system to accomplish locomotion on land. Potential energy, the energy of position, is created in the mid-stance phase of gait. In this single support mid-stance phase of gait, the body's center of mass is raised to its highest vertical excursion. From this high point the center of mass moves forward and down; therefore potential energy is transformed into kinetic energy. This kinetic energy loads mechanical forms, i.e. human soft tissues and resilient prosthetic components, with elastic energy. These mechanical forms are required to efficiently utilize the stored elastic energy to create the kinetic power to do the work of land-based locomotion.

The human foot, ankle, and shank with soft tissue support is a machine which has two primary biomechanical functions in level ground walking. One is to change a vertically oriented ground reaction force into forward momentum and, second, to restrict the fall of the body's center of mass. A prosthetic foot, ankle and shank with posterior calf device, also referred to as an artificial muscle device of the present invention must also accomplish these two biomechanical functions. The coiled spring calf shanks of FIGS. 28-30, 72; 32, 110; 35-36, 122; 37A, 200; 42-46, 122; and 49-52, 122; have increased elastic energy storage capacity as compared to calf shank 6 of FIGS. 3-5. The coiled spring lower portion of the shank 122 more accurately represents a functional ankle joint. The resilient posterior calf devices on the prosthesis of the invention also add elastic energy storage capacity to the prosthetic system. This increase in elastic energy storage capacity increases the magnitude of the kinetic power generated during gait to very near normal (human foot) values. The biomechanical functional operation of the prosthetic ankle joint as represented by 74, FIG. 30, and those having a coiled spring lower portion as in the embodiments of FIGS. 32-37, 42-46, 49-52 will be discussed. As mentioned above, the first biomechanical function of the "machine" made up of the human foot, ankle and shank is to change the direction of a vertically oriented ground reaction force into forward momentum. It accomplishes this at the ankle joint by a heel rocker effect. To create the highest magnitude of forward momentum between initial contact and midstance phases of gait, an ankle moment must be created. Prior art prosthetic feet that utilize a solid ankle cushion heel and/or posterior facing convexly curved design as in U.S. Pat. No. 6,071,313 to Phillips (the Phillips design) for example, have an ankle joint that does not create this moment. As a consequence, they have a vertically oriented initial loading ground reaction response. Since momentum is governed by vector rules, only a small horizontal displacement occurs in comparison to a large vertical displacement. In contrast, with the present invention the coiled spring ankle of the calf shanks 72, 105, 122, and 200 of FIGS. 28-30, 32-34 and 35-37, 42-46, 49-52 respectively, for example, create a 45° initial loading displacement angle, which creates equal vertical and horizontal displacements. This 45° displacement angle preserves forward momentum and inertia and improves the efficiency of the prosthetic foot, ankle and shank machine. In this initial loading phase of gait, the body's center of mass is at its lowest point, so any increase in this lowering of the body's center of mass decreases the efficiency of the overall machine.

Figure 26:
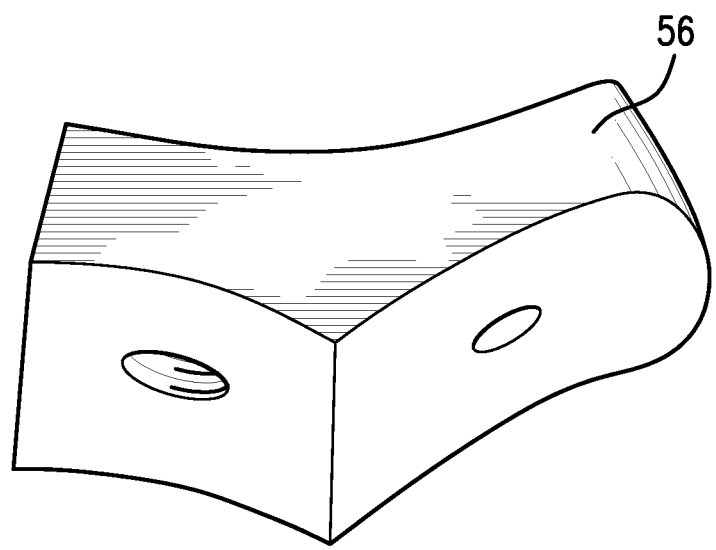
FIG. 26 is an enlarged side view of the coupling element in FIG. 25.
Figure 27:
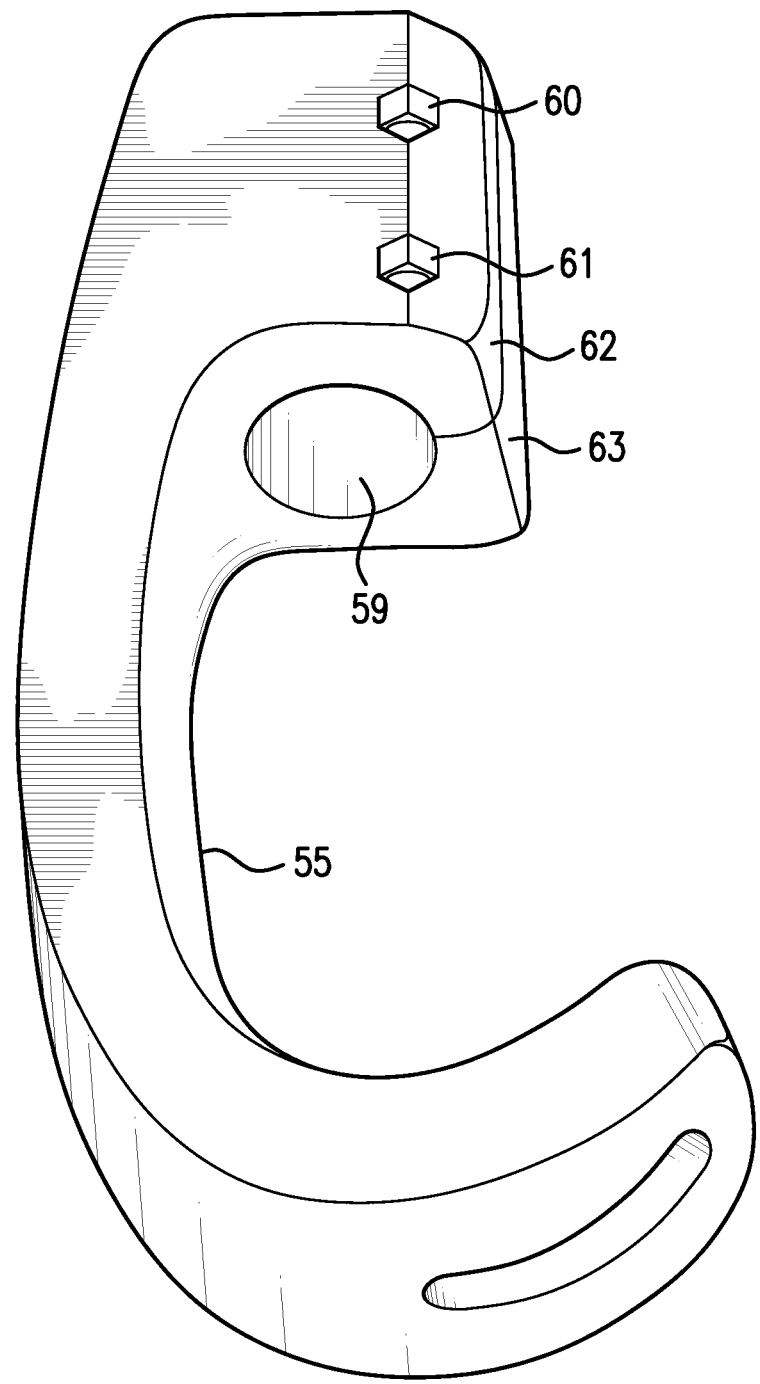
FIG. 27 is an enlarged side view of the calf shank of the prosthetic foot of FIG. 25.

The human and prosthetic foot, ankle and shank midstance to heel-off biomechanical function and operation will now be considered. There are two primary biomechanical functions of the aforementioned machine in this phase of gait. One is to create ankle joint sagittal plane kinetic power to propel the trailing and soon-to-be-swinging limb forward for the next step, and secondarily to lessen the fall of the body's center of mass. Prior art prosthetic feet that utilize a rigid pylori shank cannot store enough elastic energy to create any significant magnitude of kinetic power. The scientific literature suggests that even though these feet have varied mechanical designs, they all function about the same, creating only 25% of normal human ankle joint sagittal plane kinetic power. The Phillips design prostheses and the many other prior art foot, ankle and shank replacements have improved ankle joint sagittal plane kinetic power values in the range of 35 to 40% of normal. This represents a 70% increase in kinetic power function; however, it is significantly compromised. In contrast, the prosthesis of the present invention, with the calf shank 55, FIGS. 25-27, for example, has been shown to produce 86% of normal ankle joint sagittal plane kinetic power in gait. This represents a 244% increase in kinetic power over prior art prosthetic feet that utilize a rigid pylori and a 143% increase over the Phillips type prostheses. The present invention is also an improvement over the prior art in not allowing the body's center of mass to fall excessively and in its contribution to forward momentum. Significantly, with a Phillips design prosthesis the toe region moves vertically upward and backward during heel-off force loading in the gait cycle, in open kinetic chain movement patterns; however, in closed kinetic chain movement patterns, which occur in the gait cycle, the ankle area of the shank in these prior art prostheses moves forward and upward. This forward movement is translational kinetic motion creating an inefficient gait pattern. On the other hand, in open kinetic chain movement pattern the toe region of the prosthetic system of the present invention moves vertically upward and forward during the same heel rise force loading. Therefore, the ankle area of the present invention in closed kinetic chain movement patterns initially remains in one position in a rotational sense and translates anterior and upward to help initiate knee flexion when it is needed. This stationary rotational motion increases ankle angular velocity which increases ankle kinetic power.

A human being walks at approximately three miles per hour. A four minute miler runs at 12 miles per hour and a ten second, 100 meter sprinter sprints at 21 miles per hour. These are 1 to 4 and 1 to 7 ratios. The horizontal component of each task is greater as the velocity of the activity increases. As a consequence, the size of the prosthetic calf shank radii can be predetermined. A walker needs a smaller radii parabolic curved calf shank than a miler and a sprinter. A sprint runner needs a parabolic curved calf shank that is seven times as large. This relationship shows how to determine the parabolic radii for walkers, runners and sprinters. It is of significance because sprint runners have increased range of motion requirements and their calf shanks must be stronger to accept the increased loads associated with this activity. A wider or larger parabolic calf shank will have a relatively flatter curve, which equates to greater structural strength with increased range of motion.

The proximal length of the resilient shank should be made as long as possible. Any increase in length will increase the elastic energy storage mass and create greater kinetic power. The calf shank's proximal end can attach to the tibial tubercle height of a prosthetic socket worn by a transtibial amputee. It could also attach to the proximal anterior aspect of a prosthetic knee housing.

As shown in the embodiment of FIG. 3, a pylori adapter/leg attachment 13 is connected to the upper end of the calf shank 6 by fasteners 14. The adapter 13 in turn is secured to the lower end of pylori 15 by fasteners 16. Pylori 15 is secured to the lower limb of the amputee by a supporting structure (not shown) worn by an amputee. The forefoot, midfoot and hindfoot portions of the foot keel 2 are formed of a single piece of resilient material in the example embodiment. For example, a solid piece of material, elastic in nature, having shape-retaining characteristics when deflected by the ground reaction forces can be employed. More particularly, the foot keel and also the calf shank can be formed of a metal alloy or a laminated composite material having reinforcing fiber laminated with polymer matrix material. In particular, a high strength graphite, Kevlar, or fiberglass laminated with epoxy thermosetting resins, or extruded plastic utilized under the trade name of Delrin, or degassed polyurethane copolymers, may be used to form the foot keel and also the calf shank. The functional qualities associated with these materials afford high strength with low weight and minimal creep. The thermosetting epoxy resins are laminated under vacuum utilizing prosthetic industry standards. The polyurethane copolymers can be poured into negative molds and the extruded plastic can be machined. Each material of use has its advantages and disadvantages. It has been found that the laminated composite material for the foot keel and the calf shank can also advantageously be a thermo-formed (prepreg) laminated composite material manufactured per industry standards, with reinforcing fiber and a thermoplastic polymer matrix material for superior mechanical expansion qualities. A suitable commercially available composite material of this kind is CYLON® made by Cytec Fiberite Inc. of Havre de Grace, Md.

The resilient material's physical properties as they relate to stiffness, flexibility and strength are all determined by the thickness of the material. A thinner material will deflect easier than a thicker material of the same density. The material utilized, as well as it's physical properties, are both associated with the stiffness to flexibility characteristics in the prosthetic foot keel and calf shank. The thickness of the foot keel and calf shank are uniform or symmetrical in the example embodiment of FIGS. 3-5, but the thickness along the length of these components can be varied as discussed below, such as by making the hindfoot and forefoot areas thinner and more responsive to deflection than the midfoot region. The foot keel and shank in each of the several embodiments of the invention disclosed herein have a relatively low moment of inertia in the sagittal plane as compared with that in the frontal plane. This is a result of the mechanical form of these members, which are wider in the frontal plane than thick in the sagittal plane.

To aid in providing the prosthetic foot 1 with a high low dynamic response capability, the midfoot portion 5 is formed by a longitudinal arch such that the medial aspect of the longitudinal arch has a relatively higher dynamic response capability than the lateral aspect of the longitudinal arch. For this purpose, in the example embodiment, the medial aspect of the longitudinal arch concavity is larger in radius than the lateral aspect thereof.

The interrelationship between the medial to lateral radii size of the longitudinal arch concavity of the midfoot portion 5 is further defined as the anterior posterior plantar surface weight bearing surface areas of the foot keel 2. The line T1-T2 on the anterior section of 5 in FIG. 8 represents the anterior plantar surface weight bearing area. Line P1-P2 represents the posterior plantar weight-bearing surface of 5. The plantar weight bearing surfaces on the lateral side of the foot would be represented by the distance between T1-P1. The plantar weight bearing surfaces on the medial side of the foot 2 are represented by the distance between P2-T2. The distances represented by T1-P1 and P2-T2 determine the radii size, and as a result the high low dynamic response interrelationship is determined and can be influenced by converging or diverging these two lines T1-T2 to P1-P2. As a result, high low dynamic response can be determined in structural design.

The posterior end 17 of the hindfoot portion 4 is shaped in an upwardly curved arch that reacts to ground reaction forces during heel strike by compressing for shock absorption. The heel formed by the hindfoot portion 4 is formed with a posterior lateral corner 18 which is more posterior and lateral than the medial corner 19 to encourage hindfoot eversion motion during initial contact phase of gait. The anterior end 20 of the forefoot portion 3 is shaped in an upwardly curved arch to simulate the human toes being dorsiflexed in the heel rise toe off position of the late stance phase of gait. Rubber or foam pads 53 and 54 are provided on the lower forefoot and hindfoot as cushions.

Improved biplaner motion capability of the prosthetic foot is created by medial and lateral expansion joint holes 21 and 22 extending through the forefoot portion 3 between dorsal and plantar surfaces thereof. Expansion joints 23 and 24 extend forward from respect ones of the holes to the anterior edge of the forefoot portion to form medial, middle and lateral expansion struts 25-27 which create improved biplaner motion capability of the forefoot portion of the foot keel. The expansion joint holes 21 and 22 are located along a line, B-B in FIG. 5, in the transverse plane which extends at an angle a of 35° to the longitudinal axis A-A of the foot keel with the medial expansion joint hole 21 more anterior than the lateral expansion joint hole 22.

The angle $\alpha$ of line B-B to longitudinal axis A-A in FIG. 5 can be as small as 15° and still derive a high low dynamic response. As this angle a changes, so should the angle Z of the line T1-T2 in FIG. 8. The expansion joint holes 21 and 22 as projected on a sagittal plane are inclined at an angle of 45° to the transverse plane with the dorsal aspect of the holes being more anterior than the plantar aspect. With this arrangement, the distance from the releasable fastener 8 to the lateral expansion joint hole 22 is shorter than the distance from the releasable fastener to the medial expansion joint hole 21 such that the lateral portion of the prosthetic foot 1 has a shorter toe lever than the medial for enabling midfoot high and low dynamic response. In addition, the distance from the releasable fastener 8 to the lateral plantar weight bearing surface as represented by the line T1-T2 at T1 is shorter than the distance from the releasable fastener to the medial plantar surface weight bearing surface as represented by the line T1-T2 at T2 such that the lateral portion of the prosthetic foot 1 has a shorter toe lever than the medial for enabling midfoot high low dynamic response.

The anterior of the hindfoot portion 4 of the foot keel 2 further includes an expansion joint hole 28 extending through the hindfoot portion 4 between dorsal and plantar surfaces thereof. An expansion joint 29 extends posteriorly from the hole 28 to the posterior edge of the hindfoot portion to form expansion struts 30 and 31. These create improved biplaner motion capability of the hindfoot portion of the foot.

A dorsal aspect of the midfoot portion 5 and the forefoot portion 3 of the foot keel 2 form the upwardly facing concavity, 32 in FIG. 3, so that it mimics in function the fifth ray axis of motion of a human foot. That is, the concavity 32 has a longitudinal axis C-C which is oriented at an angle (15 degrees to 35 degrees) to the longitudinal axis A-A of the foot keel with the medial being more anterior than the lateral to encourage fifth ray motion in gait as in the oblique low gear axis of rotation of the second to fifth metatarsals in the human foot.

Figures 37A, 37B:
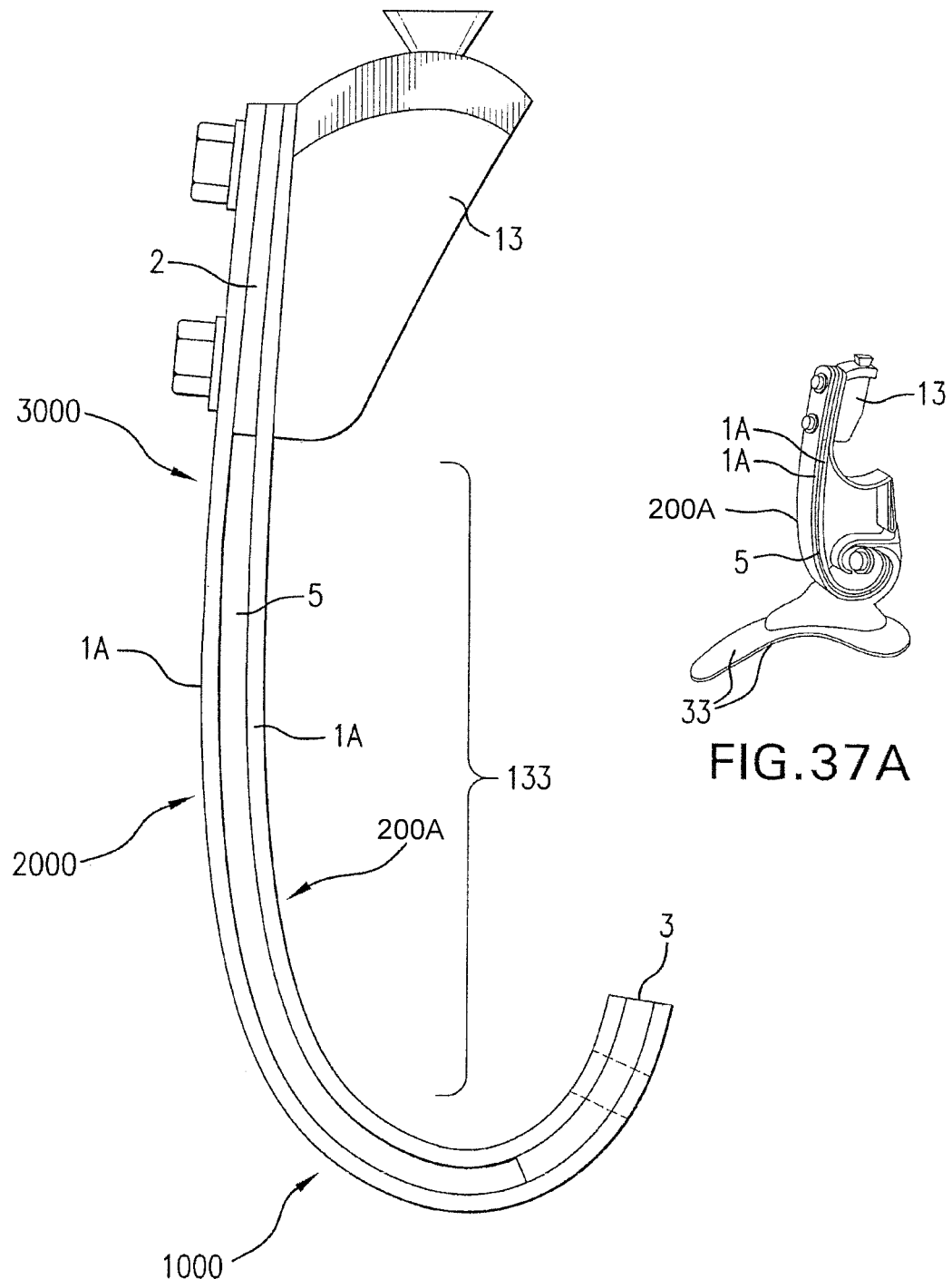
FIG. 37A is a perspective view of a still further variation of a prosthetic system which includes a resilient shank/leg member showing a plurality of sagittally oriented sections/struts with a space between adjacent sections/struts, the shank being connected to a foot keel by way of a coupling element and fasteners as in the embodiment of FIG. 25 with an adapter/leg attachment connected to the upper end of the shank.
FIG. 37B is a side view of the shank with leg attachment in FIG. 32A showing a plurality of sagittally oriented sections/struts with a gap between the sections intermediate the upper and lower ends of the shank.

The importance of biplaner motion capability can be appreciated when an amputee walks on uneven terrain or when the athlete cuts medially or laterally on the foot. The direction of the ground force vector changes from being sagittally oriented to having a frontal plane component. The ground will push medially in opposite direction to the foot pushing laterally. As a consequence to this, the calf shank leans medially and weight is applied to the medial structure of the foot keel. In response to these pressures, the medial expansion joint struts 25 and 31 of the foot keel 2 dorsiflex (deflect upward) and invert, and the lateral expansion joint struts 27 and 30 plantar flex (deflect downwards) and evert. This motion tries to put the plantar surface of the foot flat on the ground (plantar grade). Furthermore, prosthetic triplaner motion which includes, transverse, frontal, and sagittal plane motion can be further improved with the monolithically formed member with multiple sections/struts as shown in FIGS. 37A&B, 38, 40, 47 B&C, 48A-B&C, 54, 56, 60, and 62, being coupled to a coupling element 11 which is coupled to the feet keel of the invention. Moreover, any of the disclosed calf shank shapes as shown in FIGS. 1 (6); 15 (44); 16 (45); 17 (46); 18 (47); 19 (48); 20 (49); 21 (50); 22 (51); 25 (550); 32 (105, 106, 110); 37 (200); 38 (201); 40 (202); 47B (203); 47C (204); 48A (205); 48B (206); 48C (207); 49 (122); 54 (208); and 60 (209) could be utilized as a monolithically formed multi-strutted resilient member with multiple sagittally spaced sections/struts.

Figure 47A:
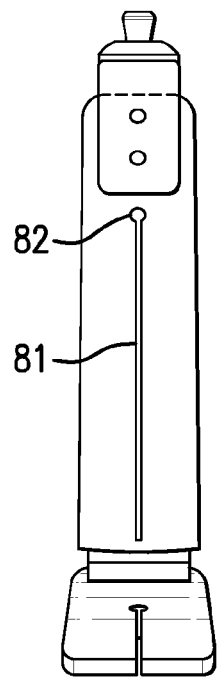
FIG. 47A is an anterior view of a prosthetic foot, ankle and shank/leg member showing a calf shank/leg member and foot keel with a longitudinal split/bifurcation extending from expansion joint holes.

To improve the prosthetic system's triplaner motion capability, the prosthetic system further includes longitudinally extending bifurcation slits and expansion joint holes which create a plurality of longitudinal struts. FIG. 47A was disclosed in commonly owned U.S. Pat. No. 7,507,259. It shows an anterior view of a prosthetic system which includes a proximal expansion joint hole 82 and a corresponding expansion slot bifurcation 81. This specific disclosure was to an expansion slot 82 intermediate the ends of the shank member 202. This split/bifurcation provides an improvement to the system's transverse plane motion capability. In the priority provisional application No. 61/336,375 referred to above a split hindfoot and midfoot were disclosed wherein at least a proximal expansion joint hole 600, as shown in FIGS. 47C and 48B, is a starting point for a longitudinal split 900 which extends downward from hole 600. This longitudinal split 900 separates the shank/leg member in substantially its entirety thereby creating a plurality of longitudinal struts. Furthermore, as shown in FIG. 47C the coupling element 11 is longitudinally split, at 900, in its entirety and the foot keel is split, 900, in the hindfoot and midfoot regions to a second expansion joint hole 601 which is located in the forefoot region. Of course, the skilled artisan will understand that the foot keel could be split, 900, in its entirety as shown in FIG. 48B. Other longitudinal splits/bifurcations 900, are disclosed in FIGS. 47B, 48A, and 48C. For example, in FIG. 47B the foot keel hindfoot 4', coupling element/riser 11, and calf shank/leg member are not longitudinally split/bifurcated. However, the foot keel has an expansion joint hole (not shown) located in the hindfoot region 4 of the foot wherein an expansion joint/bifurcation 900 extends to the toe thereby creating a plurality of midfoot and forefoot longitudinal struts. Another embodiment is shown in FIG. 48A wherein the foot keel has an expansion joint hole in the hindfoot (not shown) and an expansion joint bifurcation 900 extends from there to the toe end. In this embodiment, the coupling element 11 and the riser portion is split, 900, in its entirety. FIG. 48C shows another embodiment of the shank/leg member wherein the longitudinal split/bifurcation 900 splits the entire length of the member. Instead of utilizing two fasteners 13A to attach a proximal adapter/leg attachment 13 to the proximal member 3000, as shown in FIG. 48B, four fasteners 800 would be utilized in the four holes, as shown in FIG. 48C. The primary benefit of a longitudinal split/bifurcation 900 in the shank/leg member with split coupling element 11 and with a split 900 in the hindfoot/midfoot and or in the hindfoot, midfoot, and forefoot is that the longitudinally oriented members can flex in a frontal plane direction to improve the prosthetic system's ground compliance. This improvement in ground compliance is enhanced by the anterior facing convexly curved lower portion of the shank/leg member because it creates a mitered hinge effect similar to subtalar joint teachings in commonly owned U.S. Pat. No. 7,429,272 B2. Furthermore, a subtalar joint resilient element with a sagittally oriented joint axis which is deviated so the anterior aspect of the joint axis is more proximal than the posterior aspect could be utilized between the shank/leg distal portion and the foot keel to further improve the prosthetic system's frontal and transverse plane motion capability.

Figure 38:
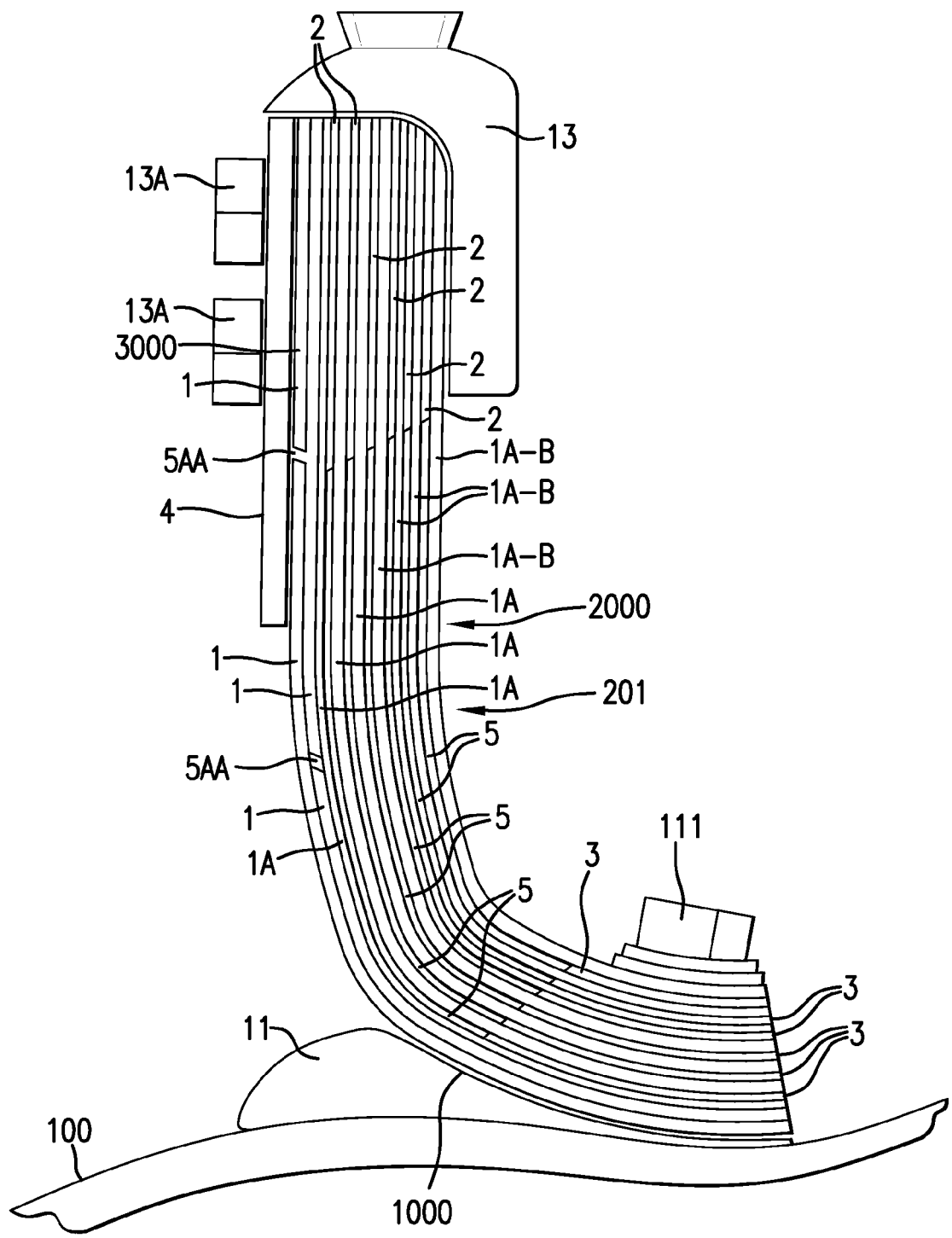
FIG. 38 is a side view of a further variation of a shank with multiple shank sections with a gap or space between adjacent sections intermediate the upper and lower ends of the shank.
Figure 47B:
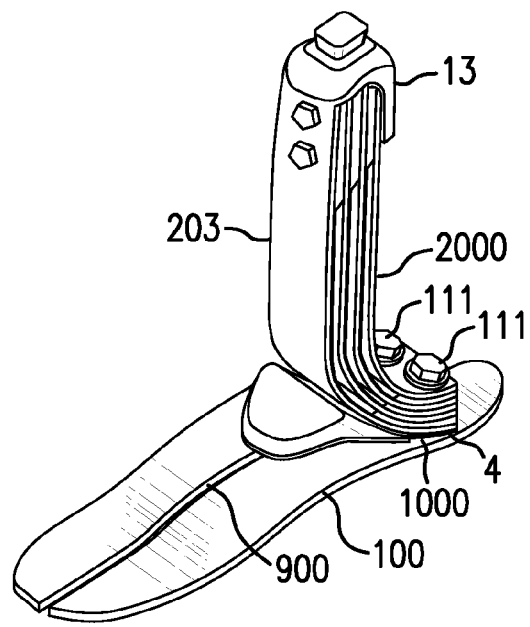
FIG. 47B is a perspective view of a prosthesis showing a foot keel with at least a longitudinal split/bifurcation in the mid- and hind foot areas.
Figure 47C:
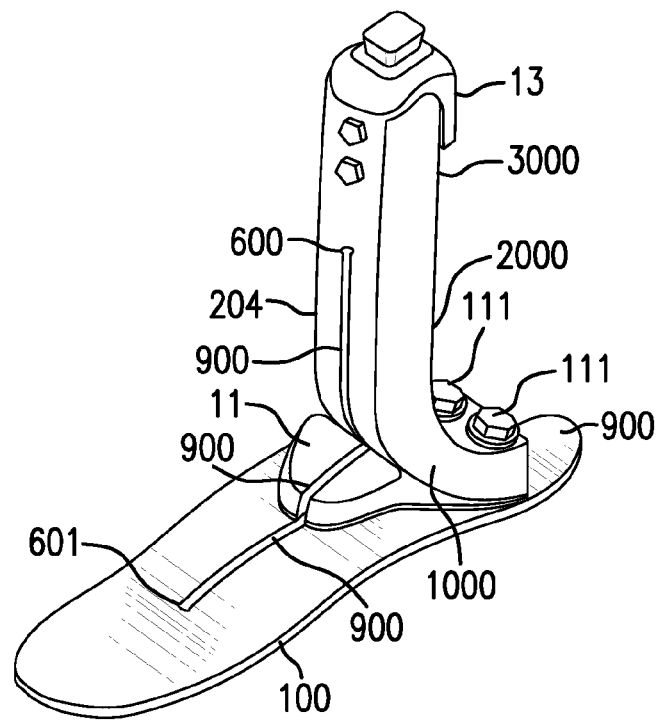
FIG. 47C is a perspective view of a prosthesis showing a longitudinal split/bifurcation arising from expansion slot holes wherein the foot keel mid/hind foot, the shank to foot keel coupling element/riser, and the distal two thirds of the shank are longitudinally split bifurcated.
Figures 48A, 48B:
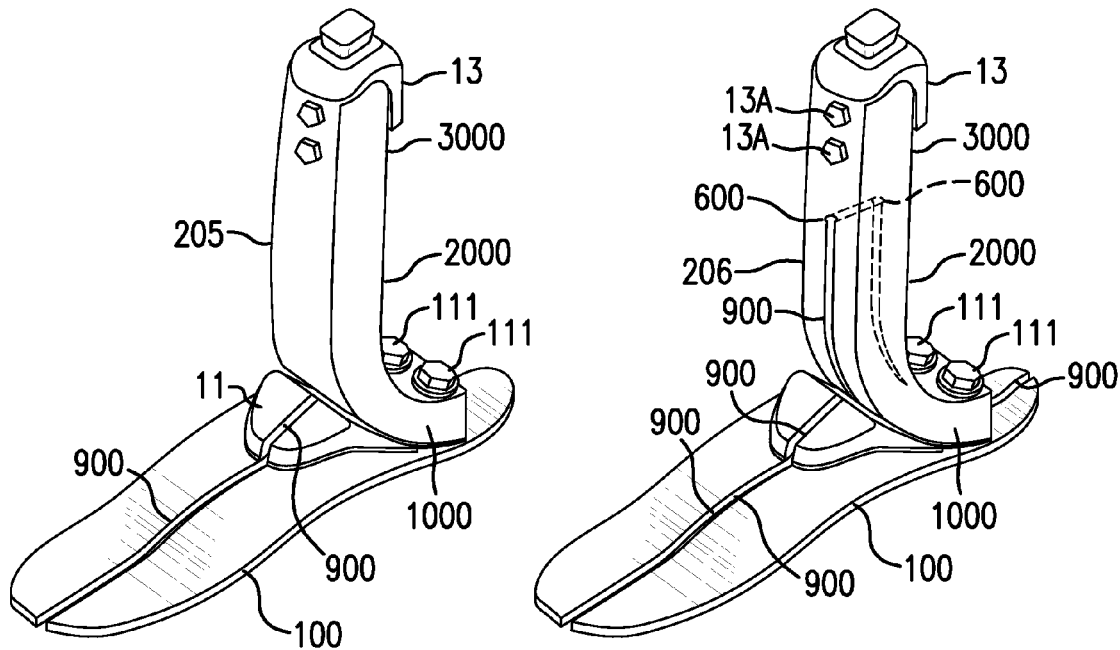
FIG. 48A is a perspective view of a prosthesis with a variation of the longitudinal split/bifurcation wherein the foot keel fore/mid foot and the foot keel to calf shank coupling element riser are longitudinally split/bifurcated.
FIG. 48B is a perspective view of a prosthesis showing another longitudinal split/bifurcation variation wherein the foot keel and shank to foot coupling element/riser are bifurcated in their entirety, and wherein the calf shank/leg is longitudinally split/bifurcated in substantially the middle and distal portions.
Figure 48C:
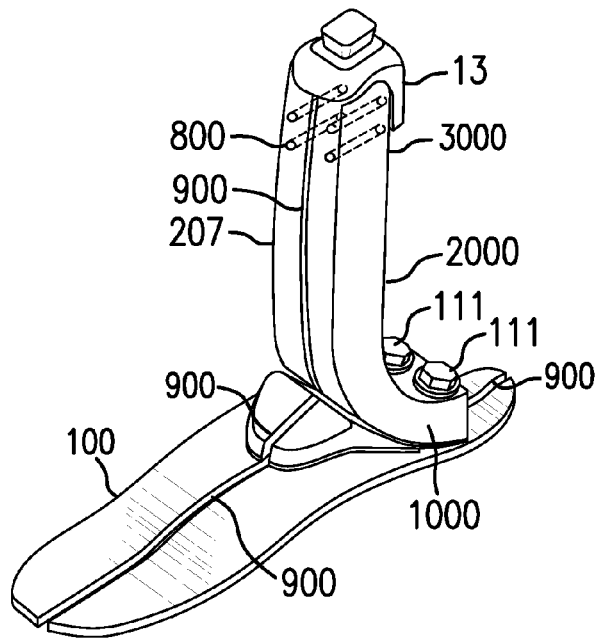
FIG. 48C shows a perspective view of a prosthesis wherein the shank/leg, the riser, and the foot keel are longitudinally bifurcated in their entirety.

The calf shank 201 in FIG. 38 can be utilized on the foot keels in FIGS. 47B, C and 48A, B, C feet and on the foot keels 100 in FIGS. 41A and 41B. "In such case the prosthesis includes: a resilient longitudinally extending foot keel 100 having forefoot 101, midfoot 102, and hindfoot 103 portions; a resilient upstanding calf shank 201 connected to the foot keel and extending upwardly there from, characterized in that the calf shank 201 has a lower portion 1000 forming an ankle area and subtalar area of the prosthetic foot, a middle portion 2000, and a proximal portion 3000 which includes an adapter/leg attachment 13 for the shank to connect to a supporting structure worn by an amputee, the lower portion posteriorly terminating in an end of the shank and extending upward from the foot keel by way of an anterior facing convexly curved surface, 2000, the shank being compressible and expandable in the sagittal FIG. 32A Line A-A, transverse, and frontal planes during gait to simulate human ankle joint plantatflexion and dorsiflexion, human subtalar inversion, eversion, and transverse plane motion, the shank extending upward above the ankle joint area 1000 to a middle portion 2000 which extends upward to a proximal portion 3000 to form a lower, prosthetic part of a leg above the ankle subtalar joint area 1000. The shank further includes a plurality of sagittally oriented shank sections/struts 1, 1A, 1A-B with a plurality of air gaps 5, 5A, 5AA being located between sections/struts each strut being wider side to side than it is thick front to back, the shank sections/struts 1A being spaced between the shanks upper and lower portions, 3000, and a coupling element, 11A/11B, FIGS. 41A/41B, spaced between the shank's lower portion 1000 and the foot keel 100. The coupling element proximal surface is contoured in a downward convexly curved shape wherein the lower portion of the shank engages the coupling element anterior portion in forefoot loading in amputee gait and wherein the shank 201 and the keel midfoot 102 and hindfoot 103 areas include a mid-sagittal plane expansion joint hole 601 extending through the midfoot portion between dorsal and plantar surfaces thereof and an expansion joint hole 600 extending through said shanks upper portion between anterior and posterior surfaces thereof and an expansion joint 900 extending posteriorly from respective midfoot expansion joint hole 601 to the hindfoot 5 posterior edge, the expansion joint 900 continuously extending through the shank lower and middle, 1000 and 2000, portions to the expansion joint hole 600 and wherein the bifurcation 900 may extend through the shank's upper portion 3000 to form the medial and lateral expansion struts thereby creating improved triplaner motion capability of the forefoot, midfoot, and hindfoot portions, 101, 102, and 103, of said foot.

Figure 6:
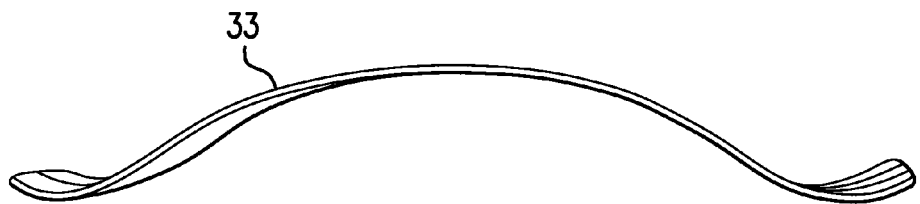
FIG. 6 is a side view of another foot keel of the invention, especially for sprinting, which may be used in the prosthetic foot of the invention.
Figure 7:
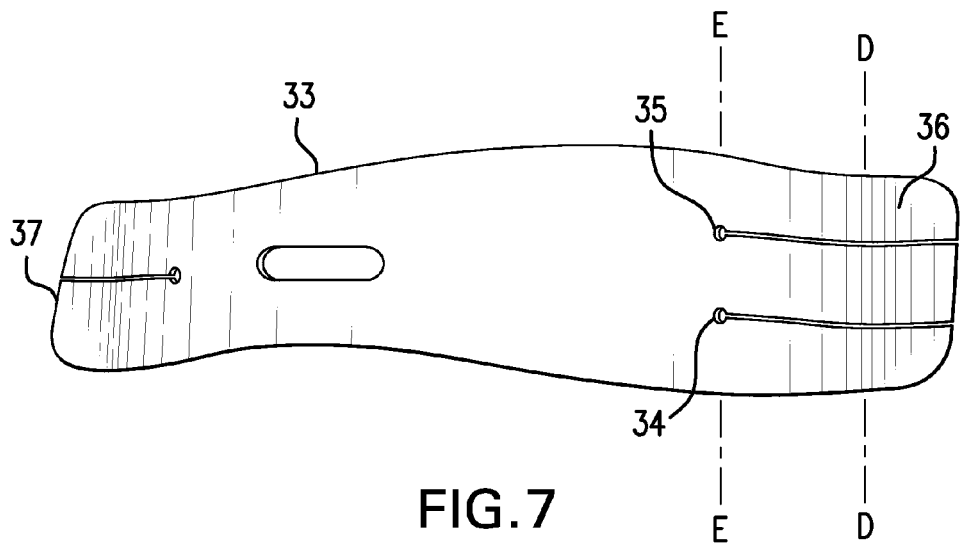
FIG. 7 is a top view of the foot keel of FIG. 6.

Another foot keel 33 of the invention, especially for sprinting, may be used in the prosthetic foot of the invention, see FIGS. 6 and 7. The body's center of gravity in a sprint becomes almost exclusively sagittal plane oriented. The prosthetic foot does not need to have a low dynamic response characteristic. As a consequence, the 15° to 35 degrees external rotation orientation of the longitudinal axis of the forefoot, midfoot concavity as in foot keel 2 is not needed. Rather, the concavity's longitudinal axis D-D orientation should become parallel to the frontal plane as depicted in FIGS. 6 and 7. This makes the sprint foot respond in a sagittal direction only. Further, the orientation of the expansion joint holes 34 and 35 in the forefoot and midfoot portions, along line E-E, is parallel to the frontal plane, i.e., the lateral hole 35 is moved anteriorly and in line with the medial hole 34 and parallel to the frontal plane. The anterior terminal end 36 of the foot keel 33 is also made parallel to the frontal plane. The posterior terminal heel area 37 of the foot keel is also parallel to the frontal plane. These modifications effect in a negative way the multi-use capabilities of the prosthetic foot. However, its performance characteristics become task specific. Another variation in the sprint foot keel 33 is in the toe, ray region of the forefoot portion of the foot where 15° of dorsiflexion in the foot keel 2 are increased to 25-40° of dorsiflexion in foot keel 33. The foot keel in this and the other embodiments could also be made without the expansion joints, expansion joint holes and expansion joint struts disclosed herein. This would reduce the ground compliance of the foot keel on uneven surfaces. However, in such case ground compliance can be achieved by the provision of a subtalar joint in the prosthesis as disclosed in commonly owned U.S. Pat. No. 7,429,272.

Figure 9:
FIG. 9 is a side view of an additional foot keel of the invention for the prosthetic foot particularly useful for sprinting by an amputee that has had a Syme amputation of the foot.
Figure 10:
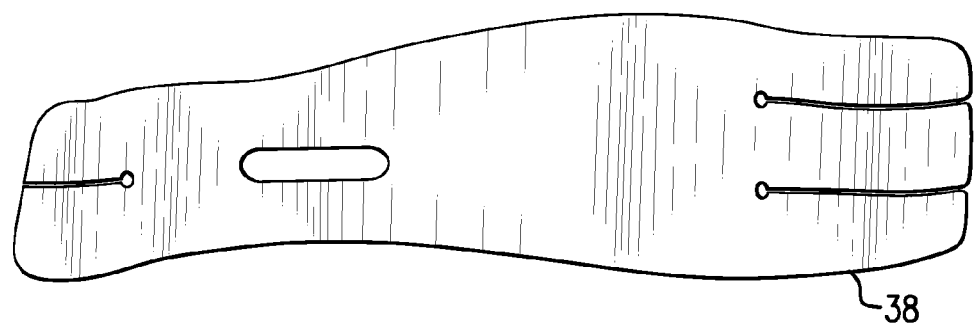
FIG. 10 is a top view of the foot keel of FIG. 9.

FIGS. 9 and 10 depict an additional foot keel 38 of the invention for the prosthetic foot particularly useful for sprinting by an amputee that has had a Syme amputation of the foot. For this purpose, the midfoot portion of the foot keel 38 includes a posterior, upwardly facing concavity 39 in which the curved lower end of the calf shank is attached to the foot keel by way of the releasable fastener. This foot keel can be utilized by all lower extremity amputees. The foot keel 38 accommodates the longer residual limb associated with the Syme level amputee. Its performance characteristics are distinctively quicker in dynamic response capabilities. Its use is not specific to this level of amputation. It can be utilized on all transtibial and transfemoral amputations. The foot keel 40 in the example embodiment of FIGS. 11 and 12 also has a concavity 41 for a Syme amputee, the foot keel providing the prosthetic foot with high low dynamic response characteristic as well as biplaner motion capabilities like those of the example embodiment in FIGS. 3-5 and 8.

The functional characteristics of the several foot keels for the prosthetic foot 1 are associated with the shape and design features as they relate to concavities, convexities, radii size, expansion, compression, and material physical properties—all of these properties relating to, reacting to, ground forces in walking, running and jumping activities.

Figure 13:
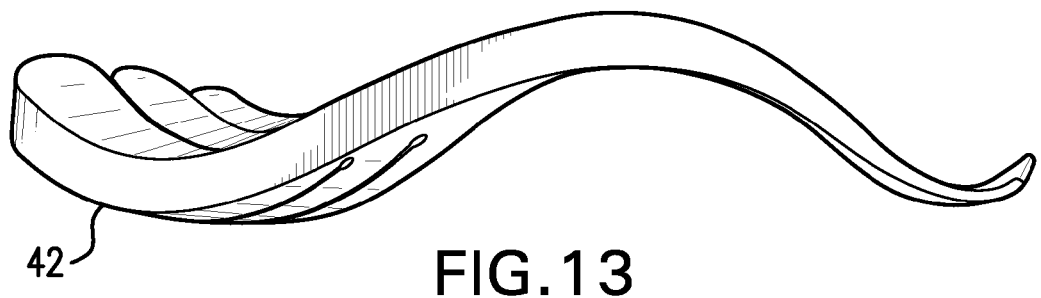
FIG. 13 is a side view of a foot keel of the invention wherein the thickness of the keel tapers, e.g., is progressively reduced, from the midfoot portion to the hindfoot portion of the keel.
Figure 14:
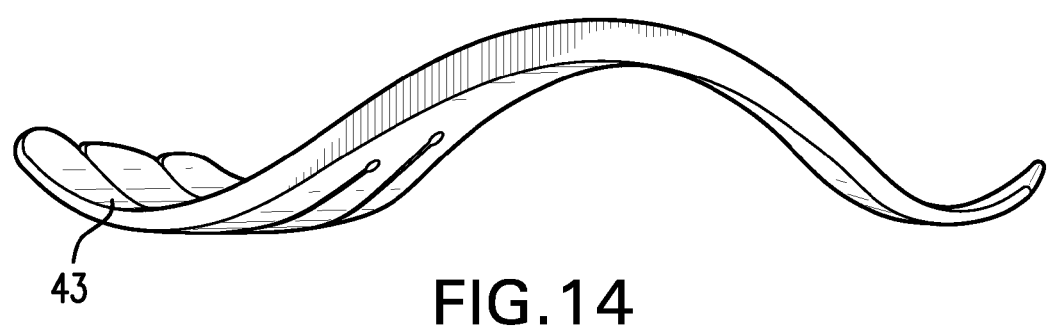
FIG. 14 is a side view of another form of the foot keel wherein the thickness of the keel tapers from the midfoot toward both the forefoot and hindfoot portions of the keel.
Figure 16:
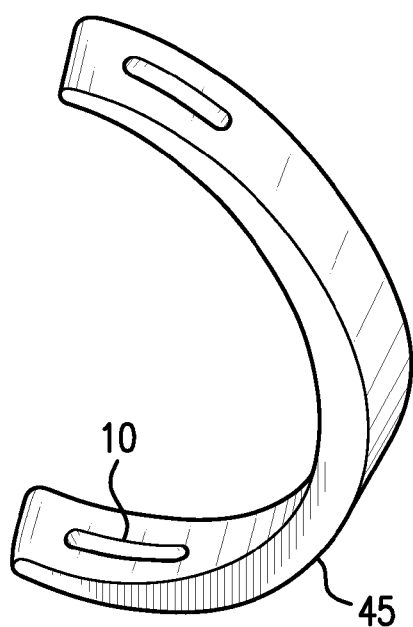
FIG. 16 is a side view like FIG. 15 but showing another calf shank tapered from the middle towards both its upper and lower ends.
Figure 17:
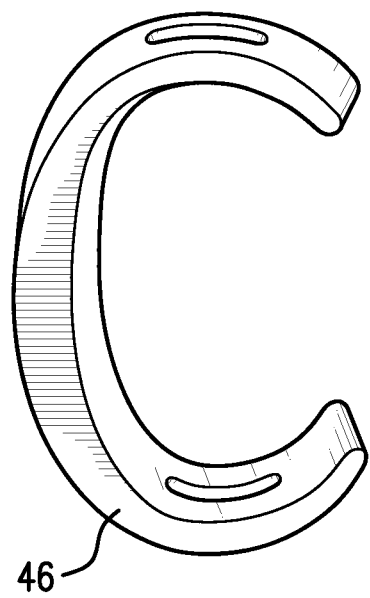
FIG. 17 is a side view of a C-shaped calf shank for the prosthetic foot, the calf shank thickness tapering from the middle towards both its upper and lower ends.
Figure 18:
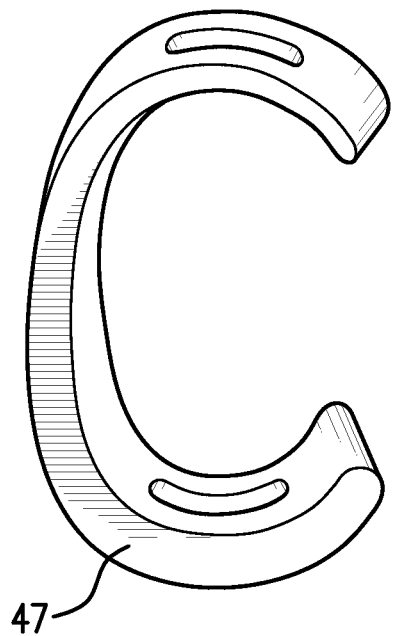
FIG. 18 is a side view of another example of a C-shaped calf shank for the prosthetic foot, the thickness of the calf shank being progressively reduced from its midportion to its upper end.
Figure 19:
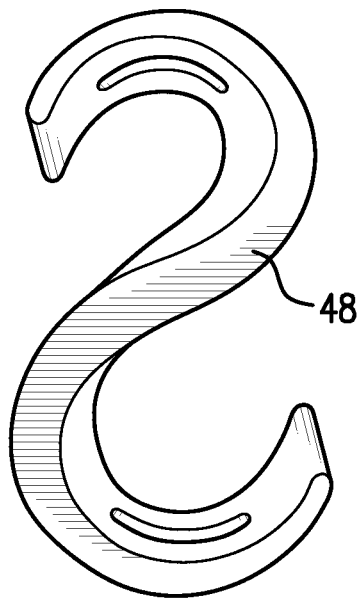
FIG. 19 is a side view of an S-shaped calf shank for the prosthetic foot, both ends being progressively reduced in thickness from the middle thereof.
Figure 20:
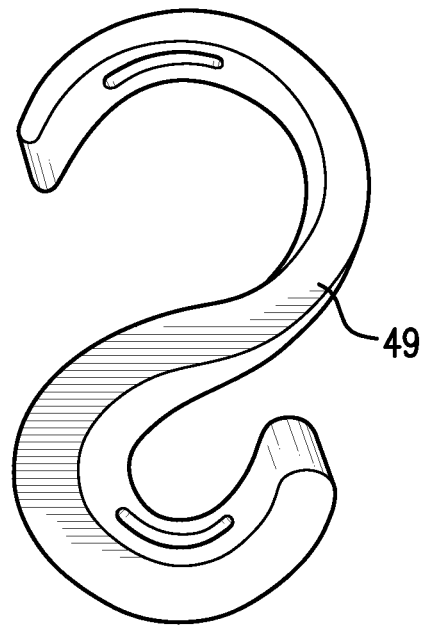
FIG. 20 is a further example of an S-shaped calf shank which is tapered in thickness only at its upper end.
Figure 21:
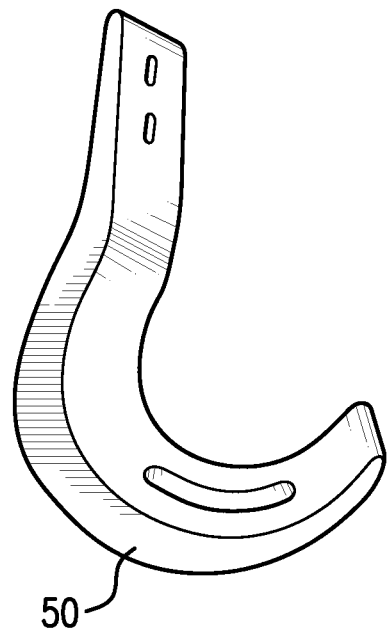
FIG. 21 is a side view of a J-shaped calf shank, tapered at each end, for the prosthetic foot of the invention.
Figure 22:
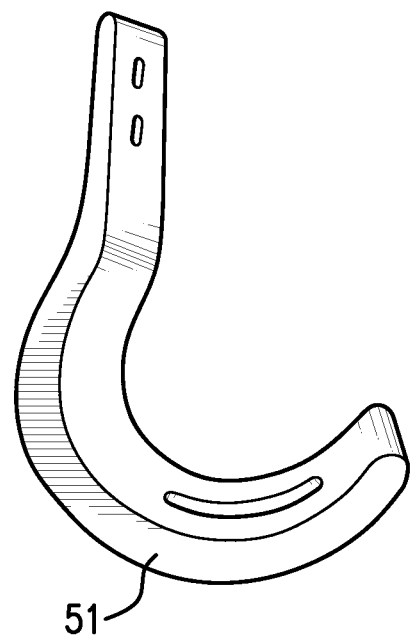
FIG. 22 is a view like FIG. 21 but showing a J-shaped calf shank which is progressively reduced in thickness towards only its upper end.

The foot keel 42 in FIG. 13 is like that in the example embodiment of FIGS. 3-5 and 8, except that the thickness of the foot keel is tapered from the midfoot portion to the posterior of the hindfoot. The foot keel 43 in FIG. 14 has its thickness progressively reduced or tapered at both its anterior and posterior ends. Similar variations in thickness are shown in the calf shank 44 of FIG. 15 and the calf shank 45 of FIG. 16 which may be used in the prosthetic foot 1. Each design of the foot keel and calf shank create different functional outcomes, as these functional outcomes relate to the horizontal and vertical linear velocities which are specific to improving performance in varied athletic related tasks. The capability of multiple calf shank configurations and adjustments in settings between the foot keel and the calf shank create a prosthetic foot calf shank relationship that allows the amputee and/or the prosthetist the ability to tune the prosthetic foot for maximum performance in a selected one or a wide variety of sport and recreational activities.

Other calf shanks for the prosthetic foot 1 are illustrated in FIGS. 17-22 and include C-shaped calf shanks 46 and 47, S-shaped calf shanks 48 and 49 and modified J-shaped calf shanks 50 and 51. The upper end of the calf shank could also have a straight vertical end with an adapter/leg attachment in the form of a pyramid attachment plate attached to this proximal terminal end. A male pyramid could be bolted to and through this vertical end of the calf shank. Plastic or aluminum fillers to accept the proximal male pyramid and the distal foot keel could also be provided in the elongated openings at the proximal and distal ends of the calf shank. The prosthetic foot of the invention is a modular system preferably constructed with standardized units or dimensions for flexibility and variety in use.

The foot keels 2, 33, 38, 42 and 43 in the several embodiments, are each 24 cm long with the proportions of the shoe 1 shown to scale in FIGS. 3, 4 and 5, and in the several views of the different calf shanks and foot keels. However, as will be readily understood by the skilled artisan, the specific dimensions of the prosthetic foot can be varied depending on the size, weight and other characteristics of the amputee being fitted with the foot.

The operation of the prosthetic foot 1 in walking and running stance phase gait cycles will now be considered. Newton's three laws of motion, that relate to law of inertia, acceleration and action-reaction, are the basis for movement kinematics in the foot 2. From Newton's third law, the law of action-reaction, it is known that the ground pushes on the foot in a direction equal and opposite to the direction the foot pushes on the ground. These are known as ground reaction forces. Many scientific studies have been done on human gait, running, and jumping activities. Force plate studies show us that Newton's third law occurs in gait. From these studies, we know the direction the ground pushes on the foot.

The stance phase of walking/running activities can be further broken down into deceleration and acceleration phases. When the prosthetic foot touches the ground, the foot pushes anteriorly on the ground and the ground pushes back in an equal and opposite direction—that is to say the ground pushes posteriorly on the prosthetic foot. This force makes the prosthetic foot move. The stance phase analysis of walking and running activities begins with the contact point being the posterior lateral corner 18, FIGS. 5 and 8, which is offset more posteriorly and laterally than the medial side of the foot. This offset at initial contact causes the foot to evert and the calf shank ankle area to plantarflex. The calf shank always seeks a position that transfers the body weight through its shank, e.g., it tends to have its long vertical member in a position to oppose the ground force. This shank compression (i.e. plantarflexion) causes the foot to be lowered to the ground. The shanks proximal portion always seeks a position to oppose the ground reaction force.

The ground reaction force cause calf shanks 44, 45, 46, 47, 50 and 51 to compress with the proximal end moving posterior. With calf shanks 48, 49 the distal ½ of the calf shank would compress depending on the distal concavities orientation. If the distal concavity is compressed in response to the GRF the proximal concavity would expand. The calf shank lower tight radius compresses simulating human ankle joint plantar flexion and the forefoot is lowered by compression to the ground. As the lower shank compresses the foot keel hindfoot area compresses upward. Both of these compressive forces act as shock absorbers. This shock absorption is further enhanced by the offset posterior lateral heel 18 which causes the foot to evert, which also acts as a shock absorber, once the calf shank has stopped moving into plantar flexion and with the ground pushing posteriorly on the foot.

The compressed members of the foot keel and calf shank then start to unload—that is they seek their original shape and the stored energy is released—which causes the calf shank proximal end to move anteriorly in an accelerated manner. As the calf shank approaches its vertical starting position, the ground forces change from pushing posteriorly to pushing vertically upward against the foot. Since the prosthetic foot has posterior and anterior plantar surface weight bearing areas and these areas are connected by a non-weight bearing long arch shaped mid portion, the vertically directed forces from the prosthesis cause the long arch shaped mid portion to load by expansion. The posterior and anterior weight-bearing surfaces diverge. These vertically directed forces are being stored in the long arch midportion of the foot—as the ground forces move from being vertical in nature to anteriorly directed. The calf shank expands—simulating ankle dorsiflexion. This causes the prosthetic foot to pivot off of the anterior plantar weight-bearing surface. As weight unloading occurs, the long arch of the midfoot portion 5 changes from being expanded and it seeks its original shape which creates a simulated plantarflexor muscle group burst of energy return. This releases the stored vertical compressed force energy into improved expansion capabilities.

The long arch of the foot keel and the calf shank resist expansion of their respective structures. As a consequence, the calf shank anterior progression is arrested and the foot starts to pivot off the anterior plantar surface weight-bearing area. The expansion of the midfoot portion of the foot keel has as high and low response capability in the case of the foot keels in the example embodiments of FIGS. 3-5 and 8, FIGS. 11 and 12, FIG. 13, and FIG. 14. Since the midfoot forefoot transitional area of these foot keels 15 is deviated 15° to 35° externally from the long axis of the foot, the medial long arch is longer than the lateral long arch. This is important because in the normal foot, during acceleration or deceleration, the medial aspect of the foot is used.

The prosthetic foot longer medial arch has greater dynamic response characteristic than the lateral. The lateral shorter toe lever is utilized when walking or running at slower speeds. The body's center of gravity moves through space in a sinusoidal curve. It moves medial, lateral, proximal, and distal. When walking or running at slower speeds, the body's center of gravity moves more medial and lateral than when walking or running fast. In addition, momentum and inertia is less and the ability to overcome a higher dynamic response capability is less. The prosthetic foot of the invention is adapted to accommodate these principles in applied mechanics.

In addition, in the human gait cycle at midstance the body's center of gravity is as far lateral as it will go. From mid stance through toe off the body's center of gravity (BCG) moves from lateral to medial. As a consequence, the body's center of gravity progresses over the lateral side of the foot keel 2. First (low gear) and as the BCG progresses forward, it moves medially on foot keel 2 (high gear). As a consequence, the prosthetic foot keel 2 has an automatic transmission effect. That is to say, it starts in low gear and moves into high gear every step the amputee takes.

As the ground forces push anteriorly on the prosthetic foot which is pushing posteriorly on the ground, as the heel begins to rise the anterior portion of the long arch of the midfoot portion is contoured to apply these posteriorly directed forces perpendicular to its plantar surface. This is the most effective and efficient way to apply these forces. The same can be said about the posterior hindfoot portion of the prosthetic foot. It is also shaped so that the posteriorly directed ground forces at initial contact are opposed with the foot keel's plantar surface being perpendicular to their applied force direction.

In the later stages of heel rise, toe off walking and running activities, the ray region of the forefoot portion is dorsiflexed 15°-35°. This upwardly extending arc allows the anteriorly directed ground forces to compress this region of the foot. This compression is less resisted than expansion and a smooth transition occurs to the swing phase of gait and running with the prosthetic foot. In later stages of stance phase of gait, the expanded calf shank and the expanded midfoot long arch release their stored energy adding to the propulsion of the amputee's soon to be swinging lower extremity One of the main propulsion mechanisms in human gait is called the active propulsion phase. As the heel lifts the body weight is now forward of the support limb and the center of gravity is falling. As the body weight drops over the forefoot rocker FIG. 5, line C-C there is a downward acceleration, which results in the highest vertical force received by the body. Acceleration of the leg forward of the ankle, associated with lifting of the heel, results in a posterior shear against the ground. As the center of pressure moves anterior to the metatarsal heads axis of rotation the effect is an ever-increasing dorsiflexion torque. This creates a full forward fall situation that generates the major progression force used in walking. The signs of effective ankle function during the active propulsion are heel lift, minimal joint motion, and a nearly neutral ankle position. A stable midfoot is essential for normal sequencing in heel lift.

The posterior aspect of the hindfoot and the forefoot region of the foot keel incorporate expansion joint holes and expansion joint struts in several of the embodiments as noted previously. The orientation of the expansion joint holes act as a mitered hinge and biplaner motion capabilities are improved for improving the total contact characteristics of the plantar surface of the foot when walking on uneven terrain.

The Syme foot keels in FIGS. 9-12 are distinctively different in dynamic response capabilities—as these capabilities are associated with walking, running, and jumping activities. These foot keels differ in four distinct features. These include the presence of a concavity in the proximate, posterior of the midfoot portion for accommodating the Syme distal residual limb shape better than a flat surface. This concavity also lowers the height of the foot keel which accommodates the longer residual limb that is associated with the Syme level amputee. The alignment concavity requires that the corresponding anterior and posterior radii of the arched foot keel midportion be more aggressive and smaller in size. As a consequence, all of the midfoot long arch radii and the hindfoot radii are tighter and smaller. This significantly affects the dynamic response characteristics. The smaller radii create less potential for a dynamic response. However, the prosthetic foot responds quicker to all of the aforementioned walking, running and jumping ground forces. The result is a quicker foot with less dynamic response.

Improved task specific athletic performance can be achieved with alignment changes using the prosthetic foot of the invention as these alignment changes affect the vertical and horizontal components of each task. The human foot is a multi-functional unit—it walks, runs, and jumps. The human tibia fibula calf shank structure on the other hand is not a multifunctional unit. It is a simple lever which applies its forces in walking, running and jumping activities parallel to its long proximal-distal orientation. It is a non-compressible structure and it has no potential to store energy. On the other hand, the prosthetic foot of the invention has dynamic response capabilities, as these dynamic response capabilities are associated with the horizontal and vertical linear velocity components of athletic walking, running, and jumping activities and out-performing the human tibia and fibula. As a consequence, the possibility exists to improve amputee athletic performance. For this purpose, according to the present invention, the fastener 8 is loosened and the alignment of the calf shank and the foot keel with respect to one another is adjusted in the longitudinal direction of the foot keel. Such a change is shown in connection with FIGS. 1 and 2. The calf shank is then secured to the foot keel in the adjusted position with the fastener 8. During this adjustment, the bolt of the fastener 8 slides relative to one or both of the opposed, relatively longer, longitudinally extending openings 9 and 10 in the foot keel and calf shank, respectively.

An alignment change that improves the performance characteristic of a runner who makes initial contact with the ground with the foot flat as in a midfoot strike runner, for example, is one wherein the foot keel is slid anterior relative to the calf shank and the foot plantar flexed on the calf shank. This new relationship improves the horizontal component of running. That is, with the calf shank plantarflexed to the foot, and the foot making contact with the ground in a foot flat position as opposed to initially heel contact, the ground immediately pushes posteriorly on the foot that is pushing anteriorly on the ground. This causes the calf shank to move rapidly forward (by expanding) and downwardly. Dynamic response forces are created by expansion which resists the calf shank's direction of initial movement. As a consequence, the foot pivots over the metatarsal plantar surface weight-bearing area. This causes the midfoot region of the keel to expand which is resisted more than compression. The net effect of the calf shank expansion and the midfoot expansion is that further anterior progression of the calf shank is resisted which allows the knee extenders and hip extenders in the user's body to move the body's center of gravity forward and proximal in a more efficient manner (i.e., improved horizontal velocity). In this case, more forward than up than in the case of a heel toe runner whose calf shank's forward progression is less resisted by the calf shank starting more dorsiflexed (vertical) than a foot flat runner.

To analyze the sprint foot in function, an alignment change of the calf shank and foot keel is made. Advantage is taken of the foot keel having all of its concavities with their longitudinal axis orientation parallel to the frontal plane. The calf shank is plantar flexed and slid posterior on the foot keel. This lowers the distal circles even further than on the flat foot runner with the multi-use foot keel like that in FIGS. 3-5 and 8, for example. As a consequence, there is even greater horizontal motion potential and the dynamic response is directed into this improved horizontal capability.

The sprinters have increased range of motion, forces, and momentum (inertia)-momentum being a prime mover. Since their stance phase deceleration phase is shorter than their acceleration phase, increased horizontal linear velocities are achieved. This means that at initial contact, when the toe touches the ground, the ground pushes posteriorly on the foot and the foot pushes anteriorly on the ground. The calf shank which has increased forces and momentum is forced into even greater flexion and downward movement than the initial contact foot flat runner. As a consequence to these forces, the foot's long arch concavity is loaded by expansion and the calf shank is loaded by expansion. These expansion forces are resisted to a greater extent than all the other previously mentioned forces associated with running. As a consequence, the dynamic response capability of the foot is proportional to the force applied. The human tibia fibula calf shank response is only associated with the energy force potential—it is a straight structure and it cannot store energy. These expansion forces in the prosthetic foot of the invention in sprinting are greater in magnitude than all the other previously mentioned forces associated with walking and running. As a consequence, the dynamic response capability of the foot is proportional to the applied forces and increased amputee athletic performance, as compared with human body function, is possible.

Figure 25:
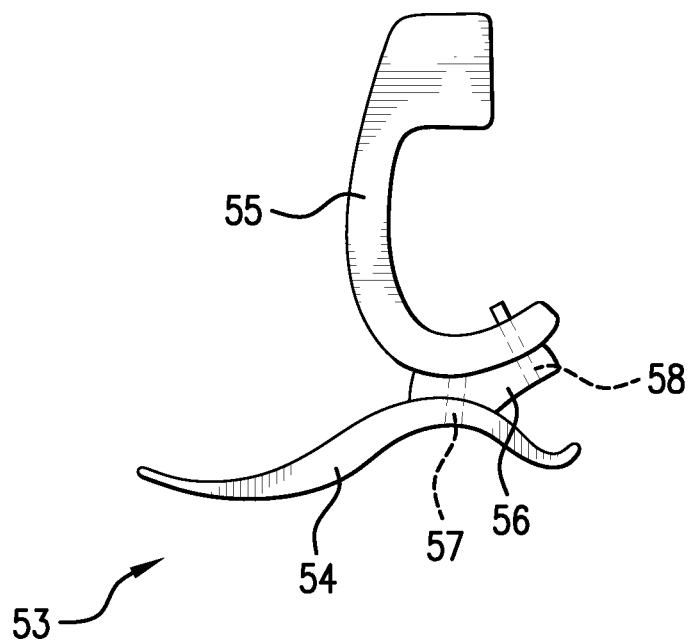
FIG. 25 is a side view of another prosthetic foot of the invention similar to that in FIG. 3, but showing use of a coupling element with two releasable fasteners spaced longitudinally connecting the element to the calf shank and foot keel, respectively.

The prosthetic foot 53' depicted in FIG. 25 is like that in FIG. 3 except for the adjustable fastening arrangement between the calf shank and the foot keel and the construction of the upper end of the calf shank for connection to the lower end of a pylori. In this example embodiment, the foot keel 54' is adjustably connected to the calf shank 55 by way of a plastic, a composite, or metal alloy coupling element 56. The coupling element is attached to the foot keel and calf shank by respective releasable fasteners 57 and 58 which are spaced from one another in the coupling element in a direction along the longitudinal direction of the foot keel. The fastener 58 joining the coupling element to the calf shank is more posterior than the fastener 57 joining the foot keel and the coupling element. By increasing the active length of the calf shank in this way, the dynamic response capabilities of the calf shank itself are increased. Changes in alignment are made in cooperation with longitudinally extending openings in the calf shank and foot keel as in other example embodiments.

The upper end of the calf shank 55 is formed with an elongated opening 59 for receiving a pylori 15. Once received in the opening, the pylori can be securely clamped to the calf shank by tightening bolts 60 and 61 to draw the free side edges 62 and 63 of the calf shank along the opening together. This pylori connection can be readily adjusted by loosening the bolts, telescoping the pylori relative to the calf shank to the desired position and clamping the pylori in the adjusted position by tightening the bolts. This shank configuration 55 is advantageous for the pediatric lower extremity amputee. By utilizing a tubular pylori in receptacle 59 the length of the prosthesis can easily accommodate growth length adjustments.

Figure 28:
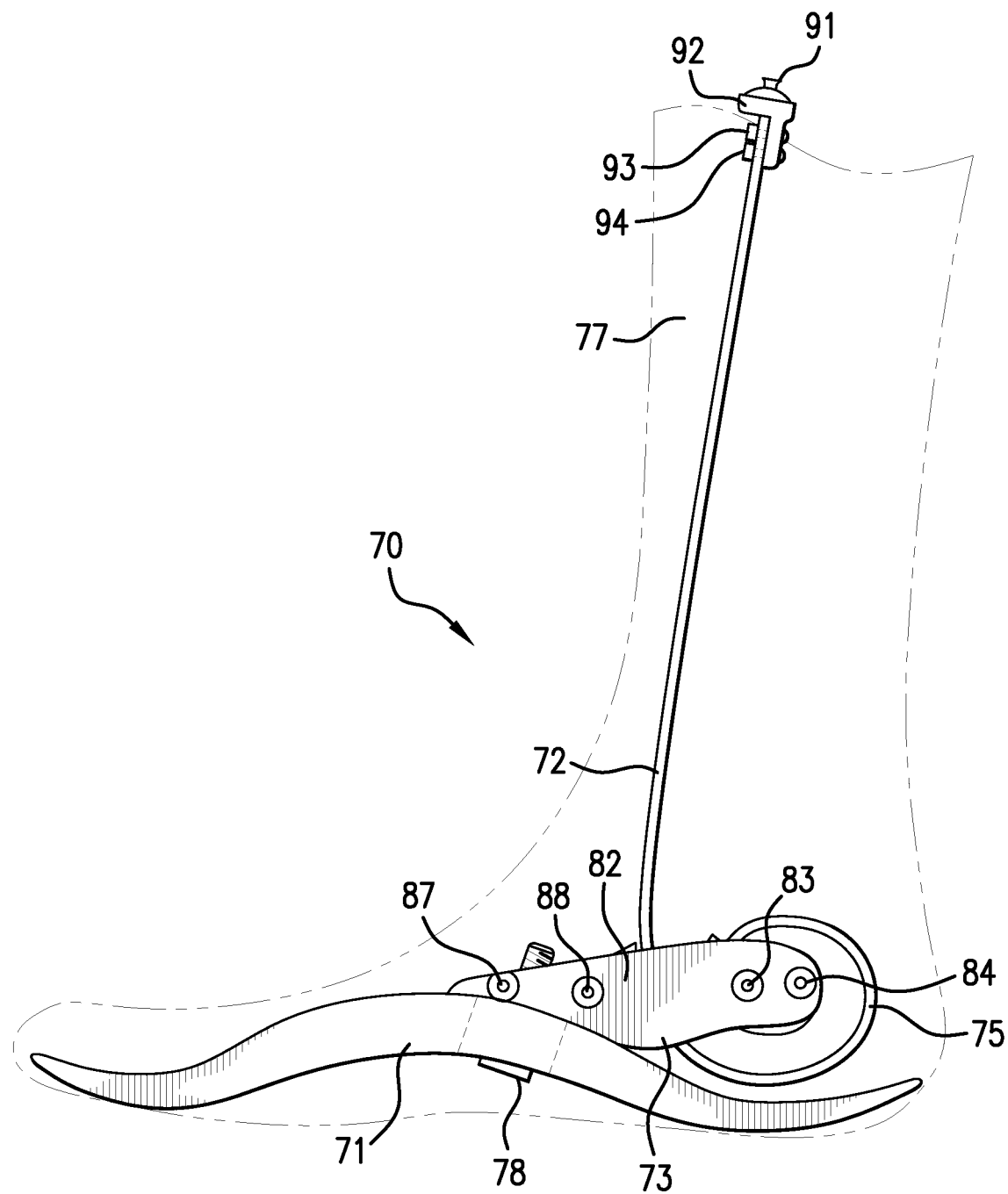
FIG. 28 is a side view of another embodiment of the prosthetic foot wherein the calf shank is utilized within a cosmetic covering.
Figure 29:
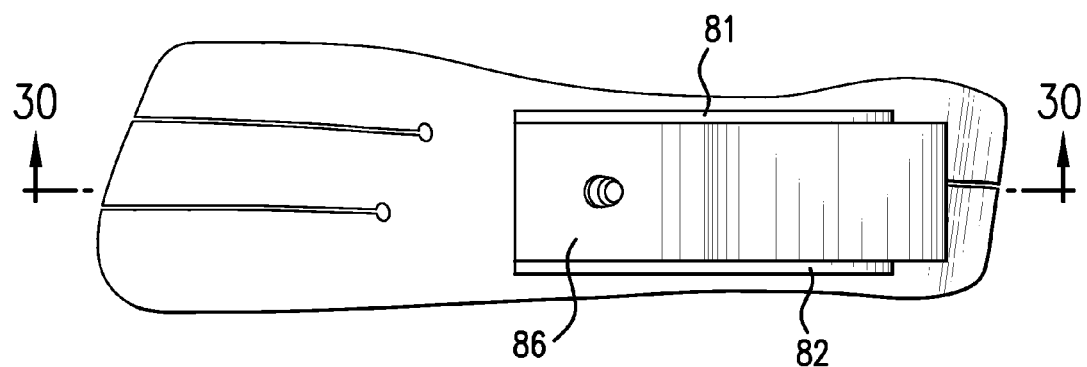
FIG. 29 is a top view of the prosthetic foot in FIG. 28

The prosthetic foot 70 according to a further embodiment of the invention is depicted in FIGS. 28-31B. The prosthetic foot 70 comprises a foot keel 71, a calf shank 72 and a coupling element 73. The prosthetic foot 70 is 20 similar to the prosthetic foot 53 in the embodiment of FIGS. 25-27, except that the calf shank 72 is formed with a downward, anteriorly facing convexly curved lower end 74 which is in the form of a spiral 75. The calf shank extends upward anteriorly from the spiral to an upstanding upper end thereof as seen in FIG. 28. The calf shank can be advantageously formed of metal, such as titanium, but other resilient materials could be used, such as composite or plastic, to form the semi-rigid, resilient calf shank.

The spiral shape at the lower end of the calf shank has a radius of curvature which progressively increases as the calf shank spirals outwardly from a radially inner end 76 thereof and as the calf shank extends upwardly from its lower, spiral end to its upper end, which may be curved or straight. It has been found that this construction creates a prosthetic foot with an integrated ankle and calf shank with a variable radii response outcome similar to the parabola shaped calf shank of the invention, while at the same time allowing the coupling element 73 and the calf shank 72 to be more posterior on the foot keel 71. As a result, the calf shank and coupling element are more centrally concealed in the ankle and leg of a cosmetic covering 77, see FIG. 28.

The coupling element 73 and 11 is formed of plastic, composite, or metal alloy, and is adjustably fastened at its anterior end to the posterior of foot keel 71 by a threaded fastener 78 as shown in FIG. 30. The foot keel has a longitudinally extending opening 79 in an upwardly arched portion thereof which receives the fastener 78 to permit adjusting the alignment of the calf shank and foot keel with respect to one another in the longitudinal direction, e.g. along the line 30-30 in FIG. 29, in the manner explained above in connection with the other embodiments.

The posterior end of the coupling element includes a cross member 80 which is secured between two longitudinally extending plates 81 and 82 of the coupling element by metal screws 83 and 84 at each end of the cross member. The radially inner end 76 of the spiral 75 is secured to the cross member 80 of the coupling element by a threaded fastener 85 as depicted in FIG. 30. From its point of connection to the cross member, the calf shank spirals around the radially inner end 76 above the heel portion of the foot keel and extends upward anteriorly from the spiral through an opening 85 through the coupling element between plates 81 and 82 anterior of the cross member 80. A cross member 86 in the anterior end of coupling element 73 is secured between plates 81 and 82 by fasteners 87 and 88 at each end as seen in FIGS. 28 and 30. The fastener 78 is received in a threaded opening in cross member 86.

The posterior surface of the cross member 86 supports a wedge 89 formed of plastic or rubber, for example, which is adhesively bonded at 90 to the cross member. The wedge serves as a stop to limit dorsiflexion of the upwardly extending calf shank in gait. The size of the wedge can be selected, wider at 89' in FIG. 31A, or narrower at 89" in FIG. 31B, to permit adjustment of the desired amount of dorsiflexion. A plurality of the wedges could be used at once, one atop another and adhesively bonded to the coupling element for reducing the permitted dorsiflexion. The coupling element 73 can also be monolithically formed.

A prosthetic socket, not shown, attached to the amputee's lower leg stump can be connected to the upper end of the calf shank 72 via an adapter/leg attachment 92 secured to the upper end of the calf shank by fasteners 93 and 94 as shown in FIG. 28. The adapter has an inverted pyramid-shaped attachment fitting 91 connected to an attachment plate attached to an upper surface of the adapter. The pyramid fitting is received by a complementarily shaped socket-type fitting on the depending prosthetic socket for joining the prosthetic foot and prosthetic socket on the user's leg.

Figure 32:
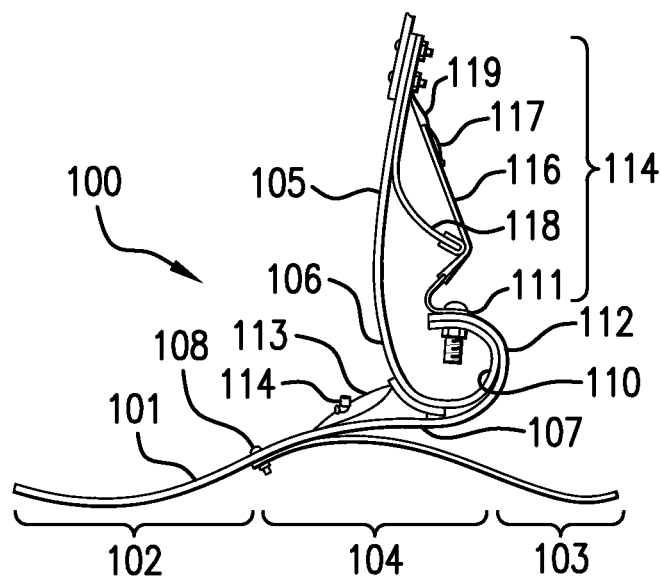
FIG. 32 is a side view of a further embodiment of the prosthetic foot wherein the lower end of the calf shank is reversely curved in the form of a spiral and housed within and supported by a coupling element monolithically formed with the forefoot portion of the foot keel.
Figure 32A:
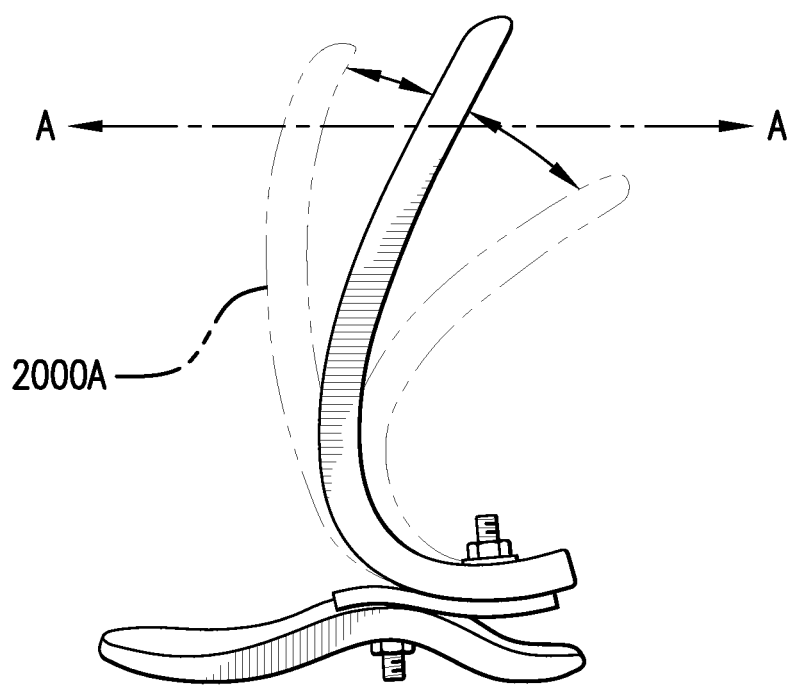
FIG. 32A is a side view of a prosthetic system showing the calf shank flexing/compressing and extending/expanding with the upper end of the shank being displaced in a longitudinal direction as shown by line A-A.
Figure 33:
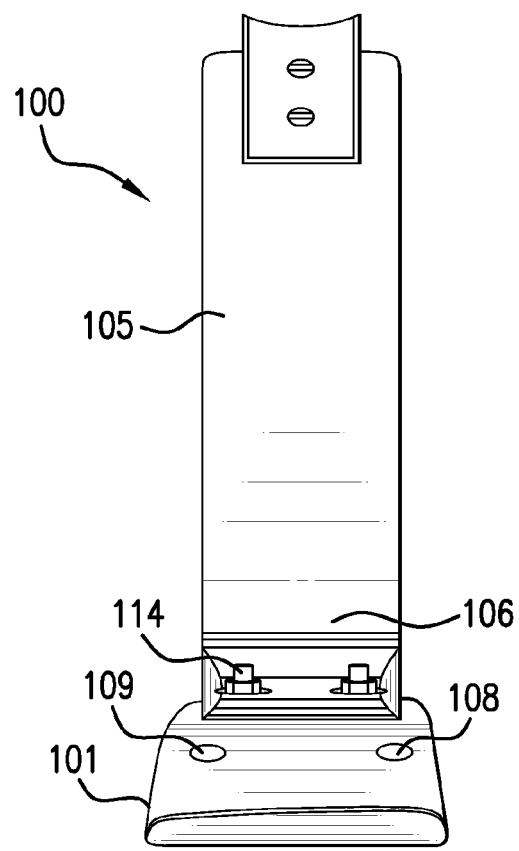
FIG. 33 is a front view of the prosthesis of FIG. 32.
Figure 34:
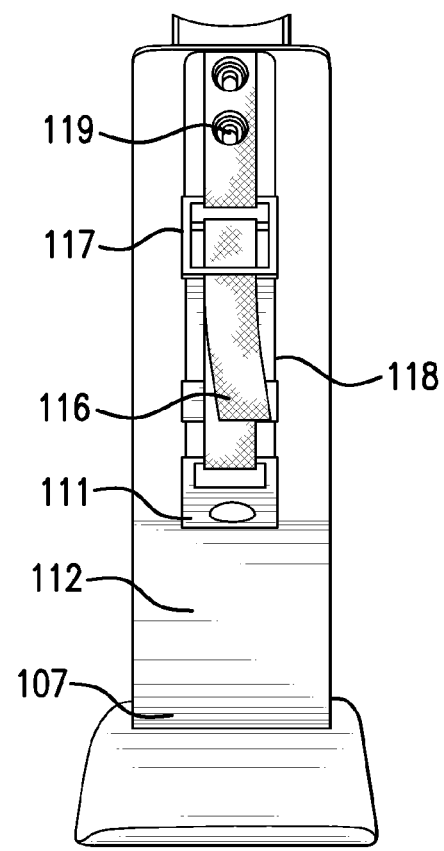
FIG. 34 is a rear view of the prosthesis of FIG. 32.

The prosthetic foot 100 of the embodiment of the invention of FIGS. 32-34 comprises a longitudinally extending foot keel 101 having a forefoot portion 102 at one end, a hindfoot portion 103 at an opposite end and a midfoot portion 104 extending between the forefoot and hindfoot portions. An upstanding calf shank 105 is secured to the foot keel at a lower end of the calf shank to form an ankle joint of the prosthetic foot and extends upward from the foot keel byway of an anterior facing convexly curved portion 106 of the calf shank. The calf shank is secured to the foot keel by way of a coupling element 107 which is monolithically formed with the forefoot portion 102 of the foot keel. The coupling element extends posteriorly from the forefoot portion as a cantilever over the midfoot portion 104 and part of the hindfoot portion 103. The hindfoot portion and the midfoot portion of the foot keel are monolithically formed and connected to the monolithically formed forefoot portion and coupling element by fasteners 108 and 109.

The lower end of the calf shank 105 is reversely curved in the form of a spiral 110. A radially inner end of the spiral 110 is fastened to the coupling element by a connector 111 in the form of a threaded bolt and nut extending through facing openings in the calf shank and the coupling element. The coupling element posterior portion 112 is reversely curved to house the spiral lower end of the calf shank, which is supported at the upper end of the curved portion 112 by the connector 111.

A stop 113 connected to the coupling element of the foot keel by fasteners 115 limits dorsiflexion of the calf shank. A cosmetic covering anterior of the calf shank in the shape of a human foot and lower leg is optionally located over the foot keel 101 and at least he lower end of the calf shank 105 with the calf shank extending upwardly from the foot keel within the lower leg covering in the manner illustrated and described in connection with the embodiment of FIG. 28.

The prosthetic foot 100 of the embodiment of FIGS. 32-34 has increased spring efficiency of the foot keel. Increasing the length of the resilient foot keel from the toe region to the connection to the lower end of the calf shank by the use of the monolithically formed forefoot portion and coupling element results in a significant spring rate gain. When the toe region of the foot keel is loaded in the late midstance phase of gait, the downward facing concavity of the cantilevered coupling element expands and the reversely curved, anterior facing concavity at the posterior end of the coupling element is compressed. Each of these resilient flexures of the coupling element of the foot keel stores energy for subsequent release during unloading in a direction which aids the forward propulsion of the limb in gait. The ankle formed by the lower end of the calf shank in the prosthesis replicates human ankle joint function, the prosthesis helping to conserve forward momentum and inertia. The configuration of the foot keel in the embodiment is not limited to that shown but could be any of the foot keel configurations shown previously including those having a high-low gear or a high gear only, having one or more expansion joints, or being formed with plural longitudinal sections, for example. Similarly, the calf shank of the embodiment could have its upper end, e.g. above the ankle and the anterior facing convexly curved portion extending upward from the foot keel, configured differently as for example with a configuration in any of the other embodiments disclosed herein. The upper end of the calf shank can be connected to a socket on the lower limb of a person for use by means of an adapter for example that in FIG. 3, FIG. 27 or FIG. 28, or other known adapter attachments.

The prosthetic foot 100 in FIGS. 32-34 further includes a posterior calf device 114 to store additional energy with anterior motion of the upper end of the calf shank in gait. That is, in the active propulsion phase of gait force loading of the resilient prosthesis expands the sagittal plane concavity of the shank 105 formed by the anterior facing convexly curved portion 106 of the calf shank which results in anterior movement of the upper end of the calf shank relative to the lower end of the calf shank and the foot keel. A flexible elongated member 116, preferably in the form of a strap, of the device 114 is connected to an upper portion of the calf shank by fasteners 119 and to a lower portion of the prosthetic foot, namely to coupling element 107 and lower end 110 of the shank by connector 111 as discussed above. The length of the flexible strap, which can be elastic and/or non-elastic, is tensioned in gait and can be adjusted by use of a slide adjustment 117 between overlapping lengths of the strap.

A curvilinear spring 118 is adjustably supported at its base on the upper end of the calf shank, for example between the calf shank and an adapter/leg attachment, not shown, secured to the calf shank, with fasteners 119. The lower, free end of the spring is positioned to interact with the flexible strap. When the strap is tensioned the spring changes the direction of the longitudinal extent of the strap. Anterior movement of the upper end of the calf shank in gait tensions/further tensions (if the strap is initially preloaded in tension) the strap and loads/ further loads the spring to store energy in force loading of the prosthetic foot in gait. This stored energy is returned by the spring in force unloading of the prosthetic foot to increase the kinetic power generated for propulsive force by the prosthetic foot in gait.

When the strap 116 is shortened using the slide adjustment 117 to initially preload the strap in tension prior to use of the prosthetic foot, the strap tension serves to assist posterior movement of the upper end of the resilient shank as well as control anterior movement of the calf shank during use of the prosthesis. Assisting the posterior movement can be helpful in attaining a rapid foot flat response of the prosthetic foot at heel strike in the initial stance phase of gait akin to that which occurs in a human foot and ankle in gait at heel strike where plantarflexion of the foot occurs.

The assisting posterior movement and the controlling anterior movement of the upper end of the resilient calf shank during use of the prosthesis using the posterior calf device 114 are each effective to change the ankle torque ratio of the prosthetic foot in gait by affecting a change in the sagittal plane flexure characteristic for longitudinal movement of the upper end of the calf shank in response to force loading and unloading during a person's use of the prosthetic fool. The natural physiologic ankle joint torque ratio in the human foot in gait, defined as the quotient of the peak dorsiflexion ankle torque that occurs in the late terminal stance of gait divided by the plantar flexion ankle torque created in the initial foot flat loading response after heel strike in gait has been reported as 11.33 to 1. An aim of changing the sagittal plane flexure characteristic for longitudinal movement of the upper end of the calf shank using the posterior calf device 114 is to increase the ankle torque ratio of the prosthesis to mimic that which occurs in the human foot in gait. This is important for achieving proper gait with the prosthesis and, for a person with one natural foot and one prosthetic foot, for achieving symmetry in gait. Preferably, through controlling anterior movement and possibly assisting posterior movement using the posterior calf device 114, the ankle torque joint ratio of the prosthesis is increased so that the peak dorsiflexion ankle torque which occurs in the prosthesis is an order of magnitude greater than the plantar flexion ankle torque therein. More preferably, the ankle torque ratio is increased to a value of about 11 to 1, to compare with the reported natural ankle torque ratio of 11.33 to 1.

A further purpose of the posterior calf device is to improve the efficiency of the prosthetic foot in gait by storing additional elastic energy in the spring 118 of the device during force loading of the prosthesis and to return the stored elastic energy during force unloading to increase the kinetic power generated for propulsive force by the prosthetic foot in gait. The device 114 may be considered to serve the purpose in the prosthetic foot that the human calf musculature serves in the human foot, ankle and calf in gait, namely efficiently generating propulsive force on the person's body in gait utilizing the development of potential energy in the body during force loading of the foot and the conversion of that potential energy into kinetic energy for propulsive force during force unloading of the fool. Approaching or even exceeding the efficiencies of the human foot in the prosthetic foot of the invention with the posterior calf device is important for restoring "normal function" to an amputee for example. The control of anterior movement of the upper end of the calf shank 105 by the posterior calf device 114 is effective to limit the range of anterior movement of the upper end of the calf shank. The foot keel in the prosthetic foot 100 by the expansion of its resilient longitudinal arch in the coupling element 107 and the compression of reversely curved portion 112 of the coupling element also contributes to storing energy during force loading in gait as discussed above. This potential energy is returned as kinetic power for generating propulsive during force unloading in gait.

Figure 35:
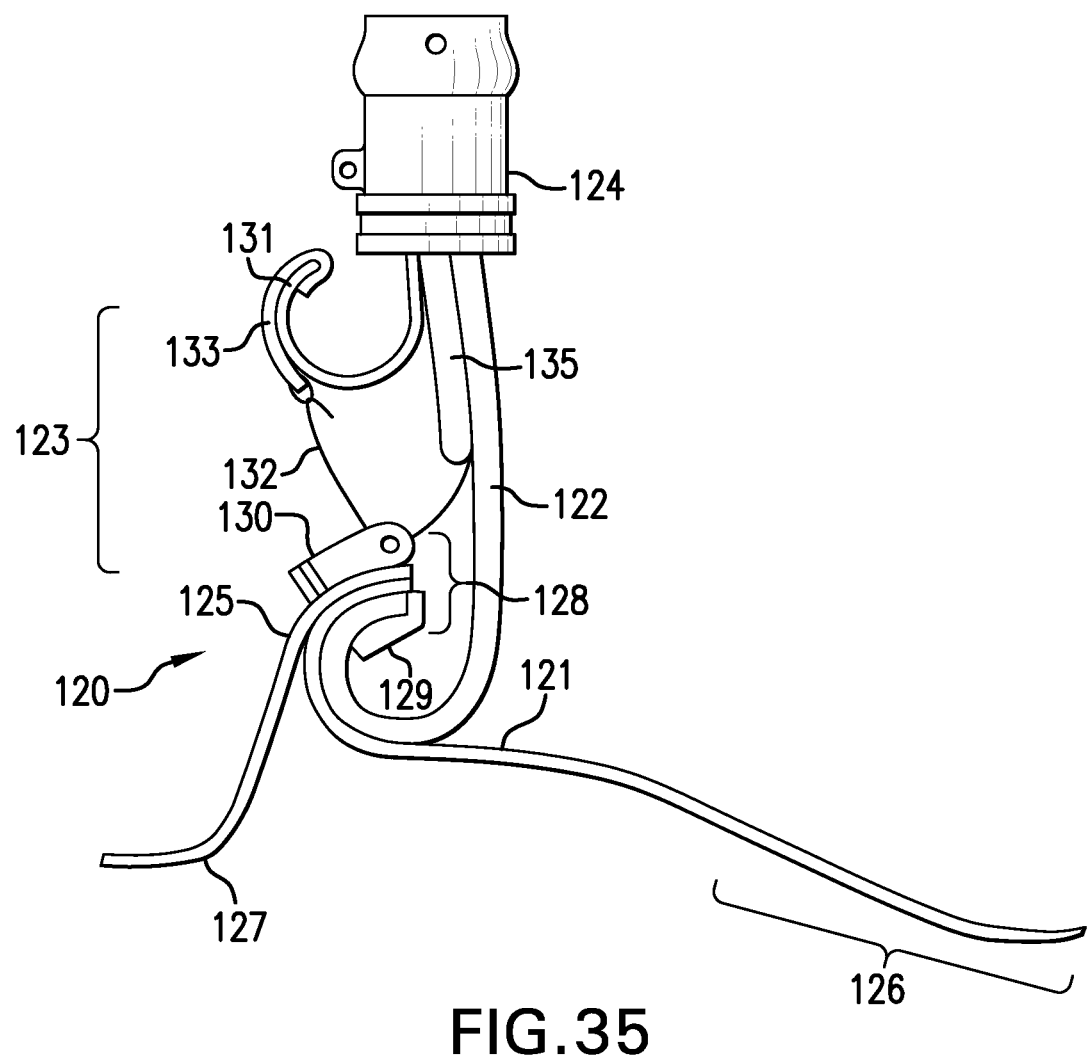
FIG. 35 is a side view of another embodiment of the prosthesis wherein a posterior component of the foot keel is joined to the reversely curved upper end of the coupling element which is monolithically formed with the forefoot portion of the foot keel.
Figure 39A:
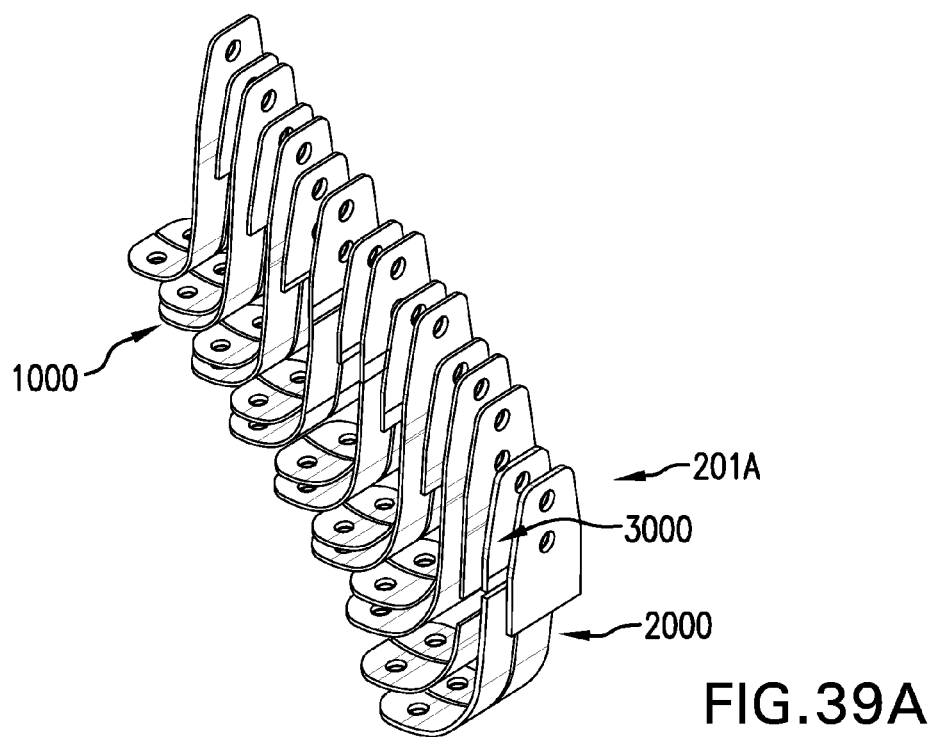
FIG. 39A is an exploded isometric view of the multiple sections of the shank of FIG. 38 showing the individual sections which make up the resilient shank/leg member.
Figure 39B:
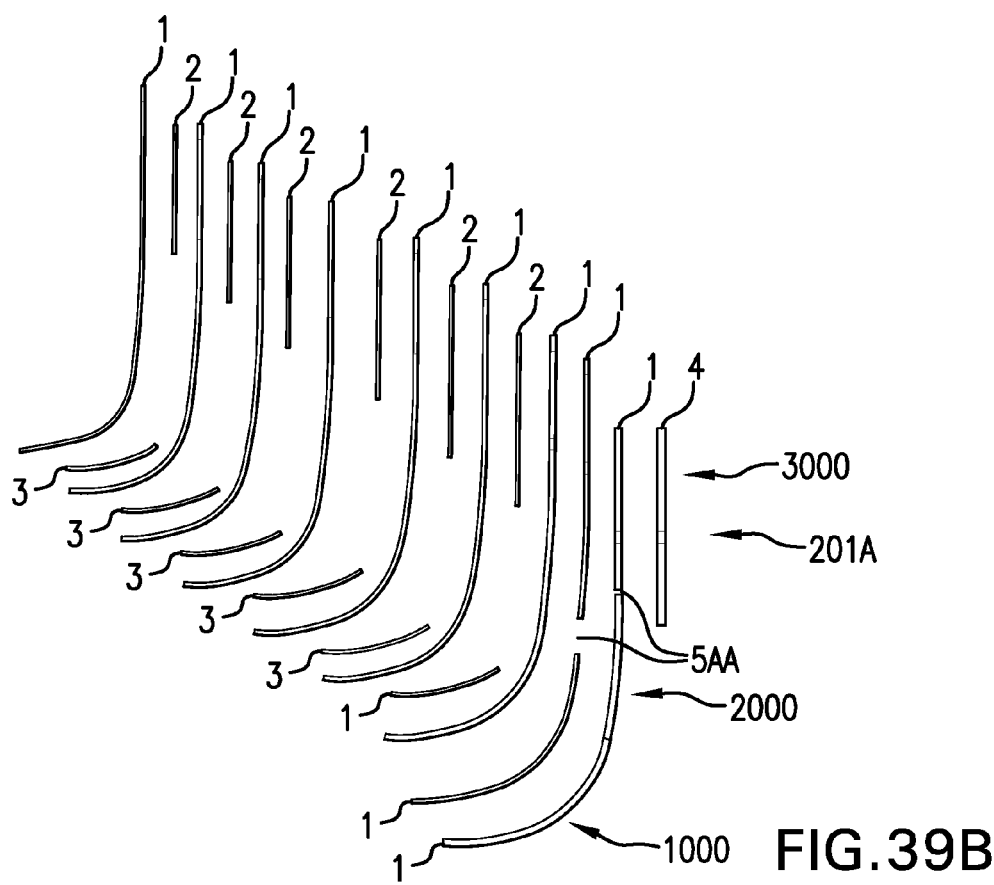
FIG. 39B is a side view of FIG. 39A showing the individual elements which make up the sagittally oriented, multiple sections/struts of the shank of FIG. 38.

The prosthesis 120 in FIG. 35 comprises a foot keel 121, a calf shank 122 and a posterior calf device 123. An adapter/leg attachment 124 is connected by suitable fasteners, not shown, to the upper end of the calf shank for securing the prosthesis to a socket on the lower limb of a person for use. Like the embodiment of FIGS. 32-34, a coupling element 125 of the prosthesis is monolithically formed with a forefoot portion 126 of the foot keel. A hindfoot portion 127 of the foot keel is joined to the upper end of the reversely curved portion of the coupling element by a fastener arrangement 128, shown disassembled in FIG. 39 prior to connection to the coupling element and calf shank. The fastener arrangement includes a radially inner component 129 against the radially inner end of the reversely curved spiral of the lower end of the calf shank, and a radially outer component 130 against the upper end of the hindfoot portion 127. A mechanical fastener, not shown, such as a through bolt and nut, extends through aligned openings in the components 129 and 130 and the complementarily curved portions of the hindfoot portion, coupling element and calf shank lower end which are sandwiched between and joined to one another by the fastening arrangement.

The posterior calf device 123 on the prosthetic foot 120 includes a coiled spring 131 supported at its one end at the upper end of the calf shank for movement therewith. A second, free end of the coiled spring has one end of a flexible elongated member, strap 132, secured thereto by a metal clip 133. The clip is connected at its one end to a first end of the strap and at its other end is hooked over in clamping engagement with the free end of the coiled spring as depicted in FIG. 35. An intermediate portion of the flexible strap 132 extends down to the foot keel and lower end of the calf shank where it extends about a return 134 in the form of a cylindrical pin 135 mounted on the component 130 of the fastener arrangement 128. To minimize sliding resistance of the strap against the pin, the pin 134 may be rotatably mounted in the component 130. The second end of the strap is retained at the upper end of the calf shank between the posterior surface of the shank and a complementarily shaped spring retainer member 135 which extends part way down the length of the shank. The upper end of the member 135 is secured between the upper end of the coiled spring and the upper end of the shank by suitable fasteners, not shown. The length of the flexible strap, which can be elastic and/or non-elastic, is tensioned in gait and can be adjusted by use of a slide adjustment, not shown, between overlapping lengths of the strap adjacent the connection to the metal clip 133, for example.

Anterior movement of the upper end of the shank relative to the foot keel and lower end of the shank in gait is yieldingly resisted by expansion of the coiled spring 131 and by posterior flexing of the lower end of the retainer member 135 to store energy during force loading of the prosthesis in the late mid-stance phase of gait, which stored energy is released during force unloading thereby contributing to ankle power generation in the prosthesis and improving efficiency. The coiled spring 131 is formed of spring steel in the embodiment but other metal alloys or non-metals such as plastic could be employed. The spring member 135 is formed of carbon fiber encapsulated in epoxy resin in the embodiment but other materials, including a metal alloy, could be used. The flexible strap 132, like the strap 116 in FIGS. 32-34, is made of a woven Kevlar (DuPont) material having a width of ⅝ inch and a thickness of 1/16 inch but other materials and dimensions could be employed as will be apparent to the skilled artisan.

The first end of the strap 132 extends through an opening in the end of the metal clip 133 and is doubled back on the strap where it is adjustably retained by a slide adjustment or other fastener. The strap could also be of fixed, non-adjustable length.

Figure 36:
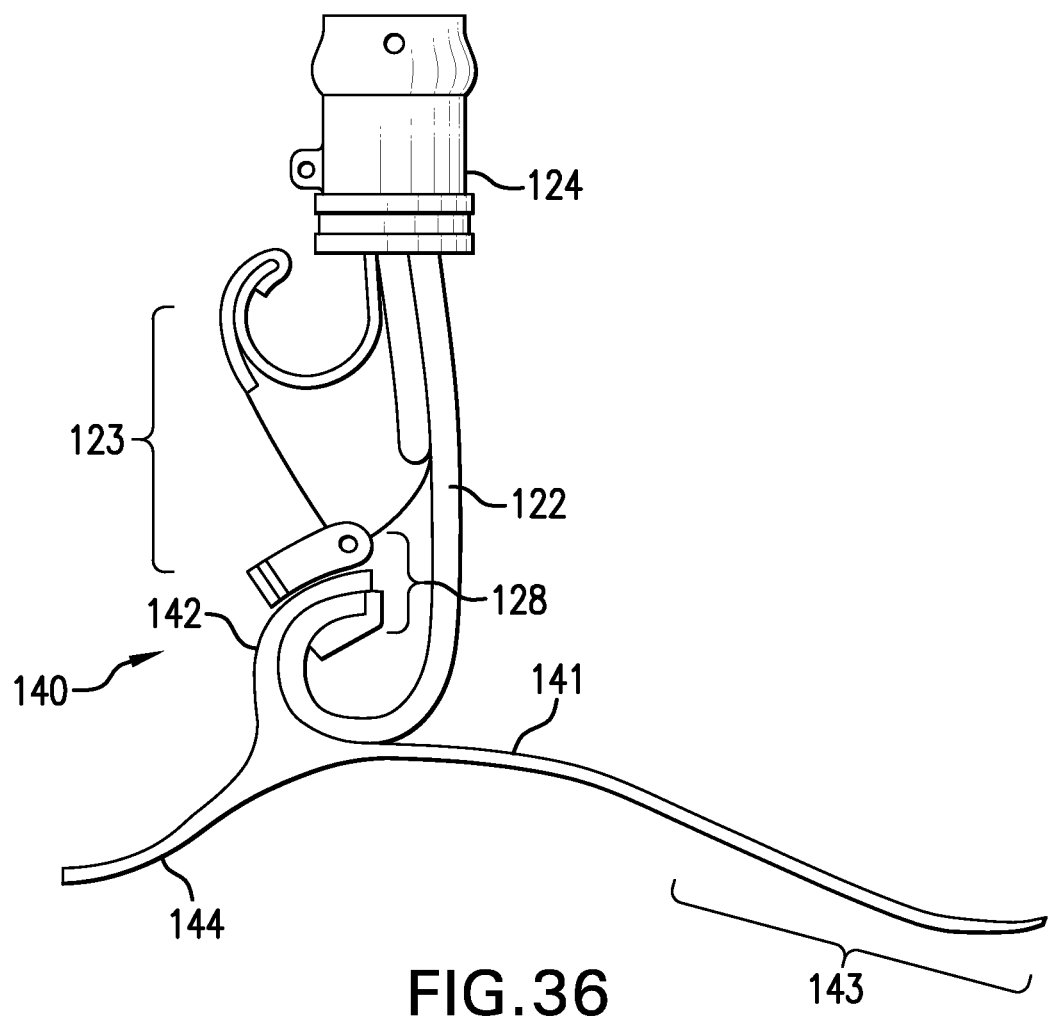
FIG. 36 is a side view of another form of the invention wherein the coupling element is monolithically formed with the foot keel.

The prosthesis 140 in the embodiment of FIG. 36 employs the calf shank 122 and posterior calf device 123 used with the prosthesis 120 of FIG. 35. The foot keel 141 of the prosthetic foot 140 includes a reversely curved coupling element 142 connected to the lower end of the calf shank by fastener arrangement 128 for housing and supporting the spiral lower end of the calf shank. In this form of the invention the coupling element is monolithically formed with both the forefoot portion 143 and the hindfoot portion 144 of the foot keel.

Figure 42:
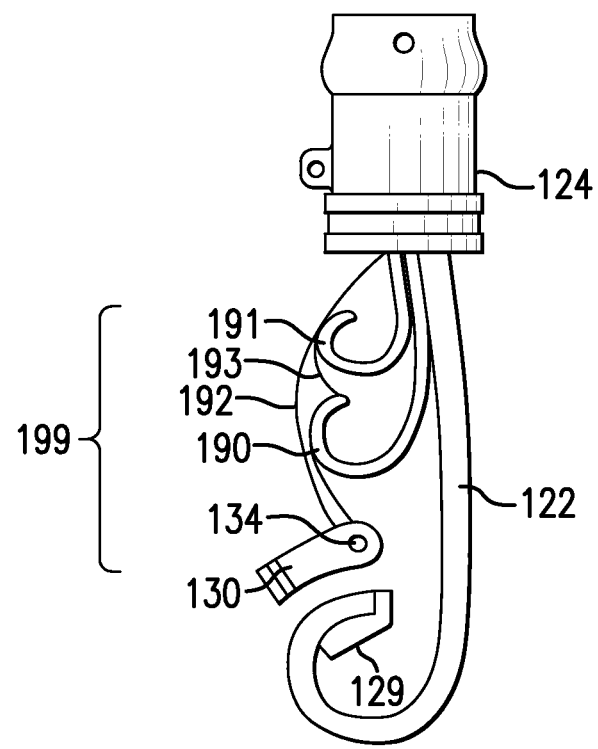
FIG. 42 is a side view of an additional posterior calf device of the invention with the two coiled springs shown in relation to the calf shank with adapter/leg attachment and fastener arrangement for use with a foot keel as in any of FIGS. 32-36 lower extremity prosthesis.
Figure 43:
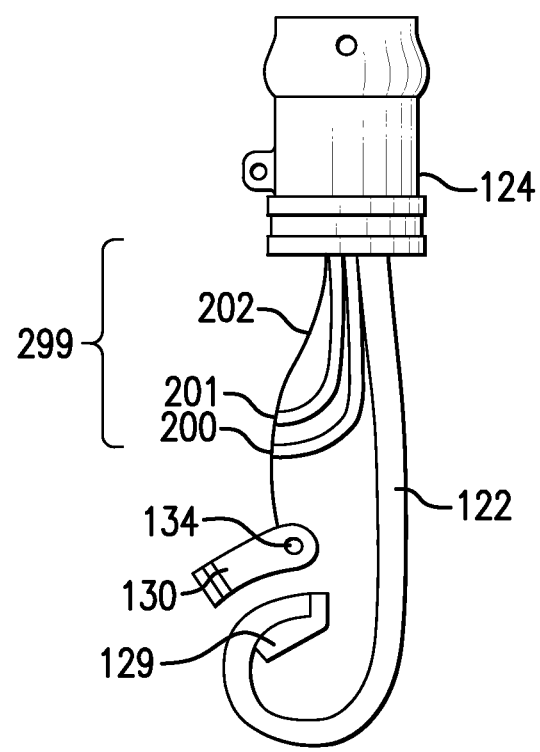
FIG. 43 is a side view of a calf shank with reversely curved lower end in the form of a spiral for use with a foot keel as in the embodiments of FIGS. 32-36, together with a further variation of a posterior calf device of the invention employing two curvilinear "J" shaped springs.
Figure 44:
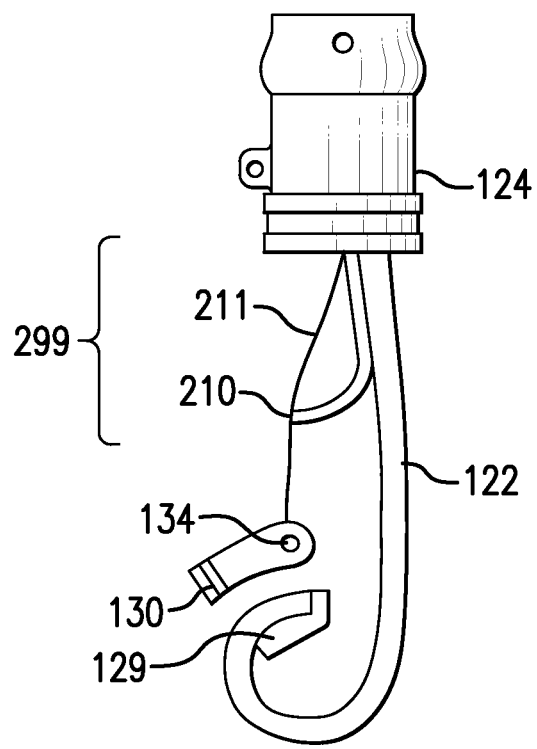
FIG. 44 is a side view of a calf shank with adapter/leg attachment, fastener arrangement, and an additional variation of a posterior calf device of the invention wherein a single curvilinear "J" shaped spring is employed.
Figure 45:
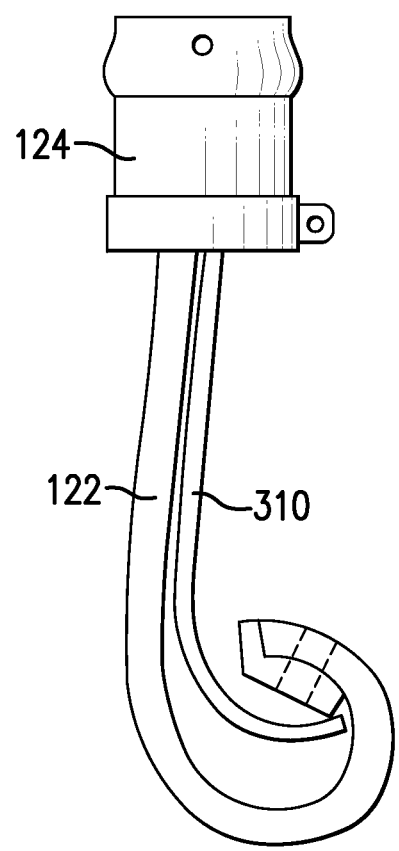
FIG. 45 is a side view of a calf shank and posterior calf device of the invention wherein a single curvilinear spring of the device is elongated to fit within the reversely curved distal end of the calf shank.
Figure 46:
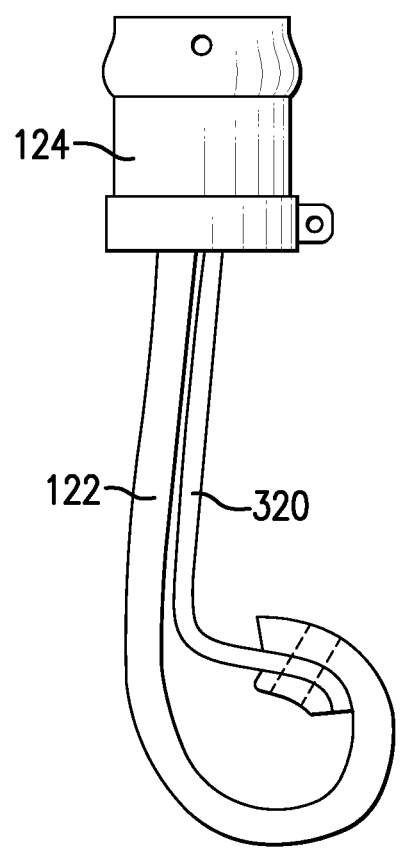
FIG. 46 is a side of a calf shank and posterior calf device of the invention wherein a single curvilinear spring of the device is elongated to fit with the reversely curved distal end of the calf shank where the spring is fastened to the shank.

In another form of the invention shown in FIG. 42 first and second coiled springs 190 and 191 are utilized in the posterior calf device. The free ends of the coiled springs are linked by a connecting strap 193 and the free end of coiled spring 190 is connected to an end of flexible strap 192 extending downwardly to and about return 134 and then upward to the upper end of the calf shank 122 where it is connected, along with the upper ends of springs 190 and 191 to the shank and adapter 124. In FIGS. 43 and 44 curvilinear springs 200, 201 and 210 are supported intermediate the flexible strap, 202 and 211, and the calf shank 122. Free ends of the spring are resiliently biased by tensioning of the flexible strap in gait to store energy. FIGS. 45, 46, 49, 50, 51, and 52 show other embodiments of the posterior calf device. In FIGS. 45 and 46 the posterior springs (310 and 320) are elongated and run into the coiled lower end of the calf shank area of the prosthetic foot. In FIG. 45, the distal terminal end of curvilinear spring 310 is free floating within the coiled ankle area. In FIG. 46, the distal end of curvilinear spring 320 has a hole so a fastener, not shown, bolts the unit together. The spring 320 can also be fastened to the top of the shank (see FIG. 52).

Figure 49:
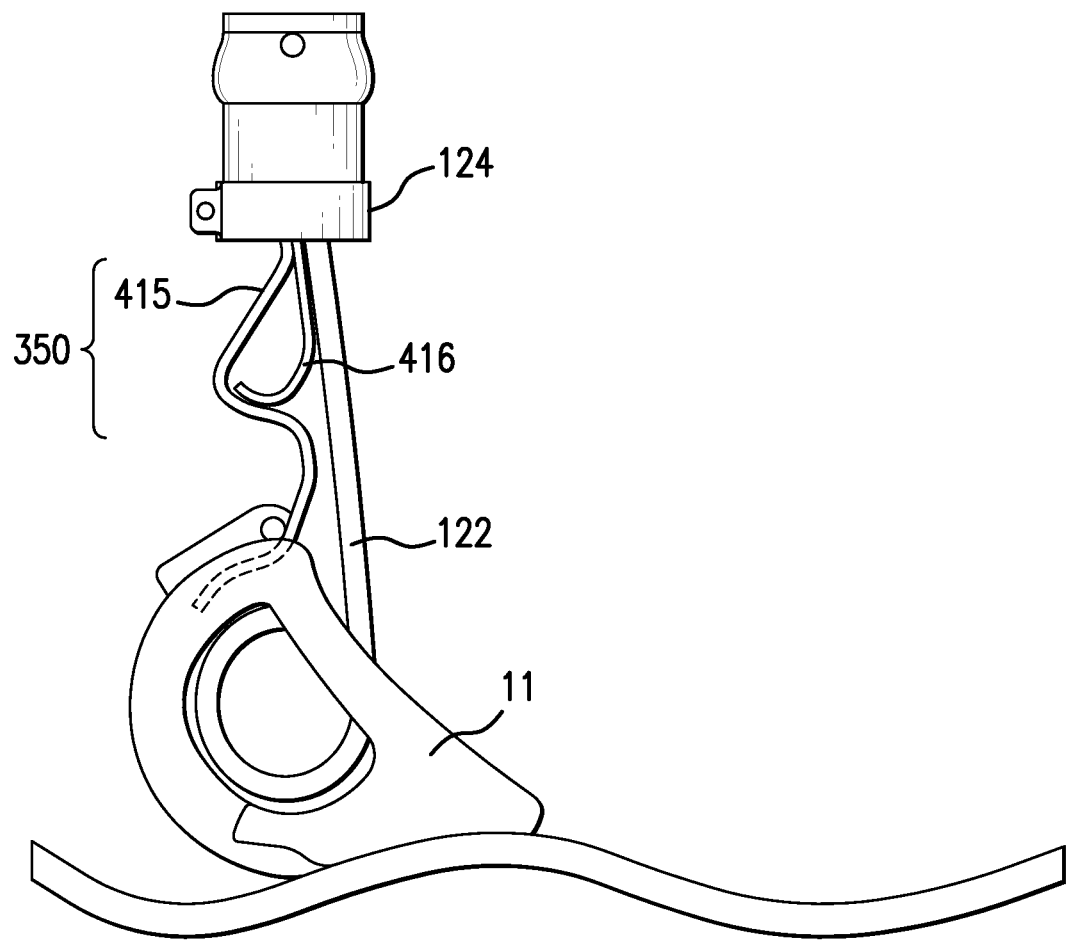
FIG. 49 is a side view of another embodiment of the prosthetic foot wherein a posterior calf device has a posterior spring in the shape of an "S" connected between an upper portion of the calf shank and a coupling element which connects the lower end of the calf shank to a foot keel, and wherein a second spring having a "J" shape is located between the S shaped spring and an upper portion of the calf shank.
Figure 50:
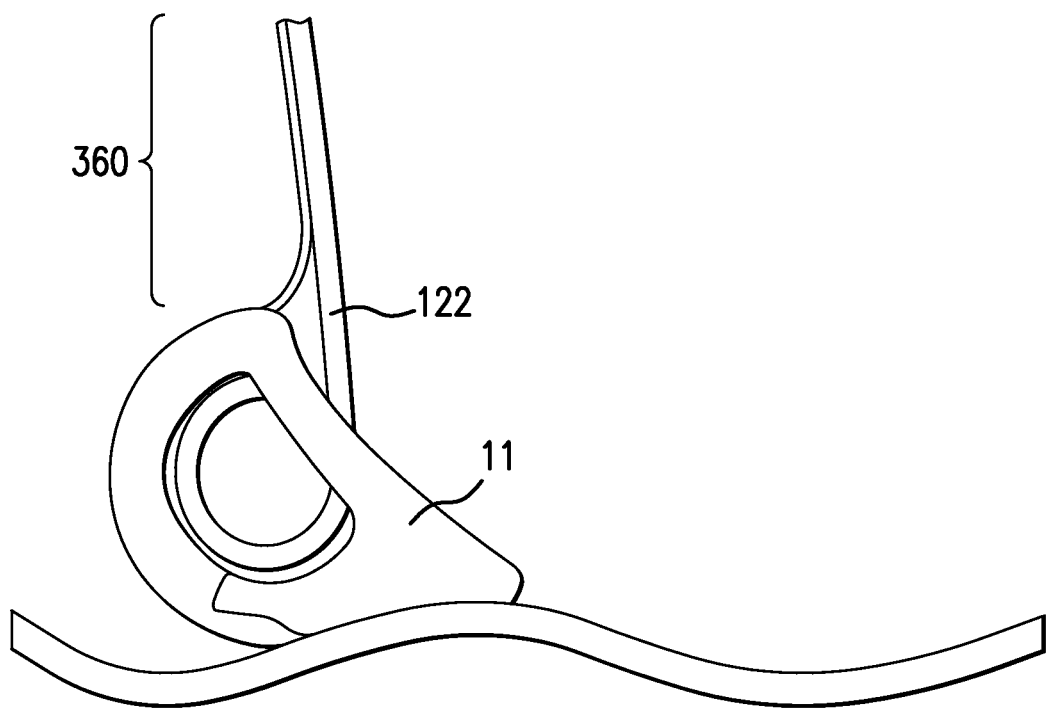
FIG. 50 is a side view of another embodiment wherein the posterior calf device has a "J: shaped spring connected between an upper portion of the calf shank and a proximal edge of a coupling element connecting the calf shank to a foot keel of the prosthesis.
Figure 51:
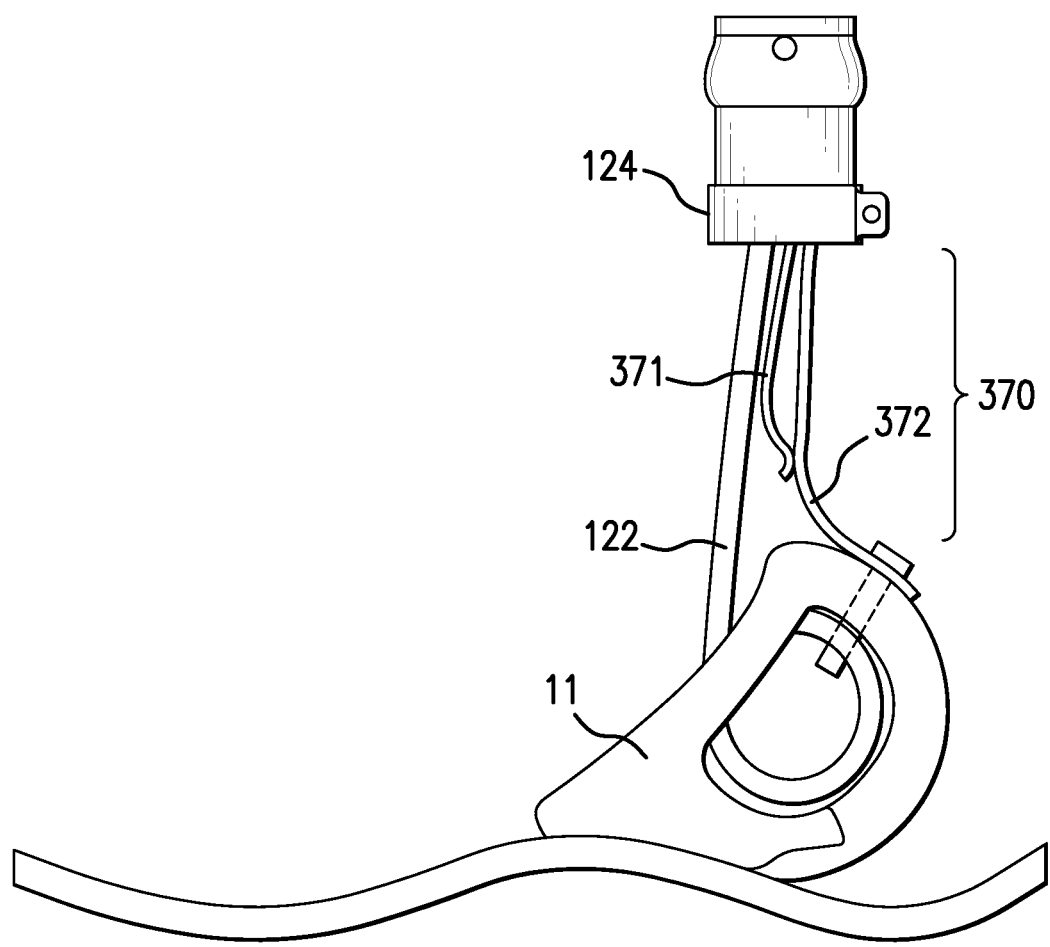
FIG. 51 is a side view of a further embodiment of the prosthetic system of the invention wherein a posterior calf device includes a plurality of leaf springs.
Figure 52:
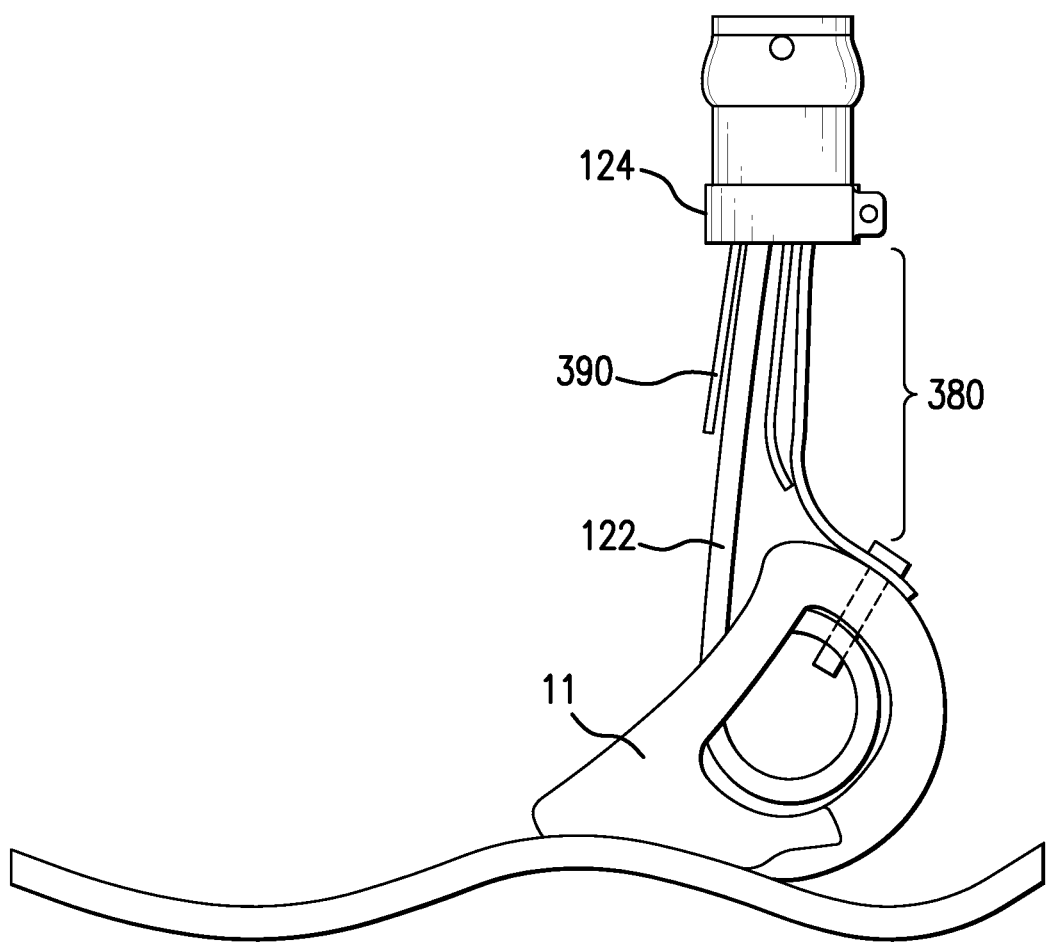
FIG. 52 is a side view of an additional embodiment of a prosthesis of the invention wherein an anterior leaf spring is provided in addition to a posterior calf device made up a plurality of posterior leaf springs.

FIGS. 49, 51, and 52 show double spring configurations. In FIG. 49 the posterior spring 415 is 'S' curved, wherein a second 'J' spring 416 is located proximally. During initial contact force heel loading, the 'S' spring compresses; however, during heel to toe loading the 'S' spring straightens and engages the 'J' spring, which increases the rigidity of the prosthetic system. The use of the two springs 415 and 416 thus results in a progressive spring rate during heel to toe loading. Other forms of springs such as asymmetric springs and multiple leaf spring arrangements could also be used to provide a progressive spring rate or spring constant with higher loading forces. FIG. 50 shows a single 'J' spring (360) attached to the proximal edge of the shank and the upper edge of the coupling element. This spring could be made with a plurality of spring elements, such as a plurality of curvilinear springs of different lengths.

As disclosed in commonly owned U.S. patent application Ser. No. 10/594,798; and the priority provisional application Nos. 60/558,119 filed Apr. 1, 2004; and 61/336,375 filed Jan. 21, 2010 in this regard, the following previously disclosed figures show a substantially, vertically oriented calf shank/leg member comprising at least a plurality of sagittally oriented sections/struts with at least an intermediate gap, wherein the gap is created by removing a proximal portion of at least one sagittally oriented section thereby creating a gap between two adjacent sections/struts and wherein the sagittally oriented struts are anterior facing convexly curved in a lower portion, see FIGS. 37A (200A); 37B (200A); 54 (208); and 56 (208); for example. Furthermore in related U.S. patent application Ser. No. 10/594,798 it was disclosed "The foot keels and calf shanks in the disclosed embodiments could also be made in a plurality of sagittally oriented struts". In the preferred embodiment of the present invention, as shown in FIGS. 37A, 37B, 38, 39, 40, 47 B-C, 48 A-C, 54, 56, 60, 61, and 62, the resilient prosthetic shank/leg member comprises a lower portion 1000; a middle portion 2000; an upper portion 3000; wherein the member incorporates at least a plurality of sagittally oriented resilient sections/struts 1, 1A, 1A-B with at least an intermediate gap 5A, 5A', 5AA" between the sections/struts, the struts being anterior facing convexly curved in the lower portion 1000, the middle portion 2000 arising from the lower portion 1000, the upper portion 3000 arising from said middle portion 2000 and the upper portion 3000 incorporating an adaptor/leg attachment 13 allowing the member to be attached to a component worn by an amputee, the upper 3000 and middle 2000 portions being substantially vertically oriented, whereby in response to midstance to late midstance gait force at least the middle portion 2000 of the member deflects in a longitudinal direction FIG. 32A, 2000A for storing energy, thereby causing the proximal adapter 13 to be displaced in the longitudinal direction.

Operation of the Multi-strutted Component Preferred Embodiment

The multi-strutted component more accurately replicates the human biomechanical function of a weight bearing structure (bone) with muscular function than a single solid structure. It is recognized that a ratio of moments exists between the below knee complexes anterior pretibial and posterior triceps surae muscle groups whereby in response to amputee gait the ankle joint with its anterior and posterior muscles experiences plantarflexion and dorsiflexion moments. The muscles physiological cross-sectional areas and moment arm length work in synergy with the human ankle joint to create ankle joint moments. Dr. Perry reported in her second edition "Gait Analysis Normal and Pathological Function" book that the physiological (muscles) cross-sectional areas and moment arm lengths of the anterior pretibials and posterior triceps surae to be 21.5 (cm2)/4.1 cm and 141.4 (cm2)/5.2 cm respectively. By multiplying the cross-sectional area by the moment arm length, the anterior pretibial and posterior triceps surae have values of 88.15 and 735.28 respectively. 735.28 divided by 88.15 equals 8.34. This is less than the 11 to 1 moment ratio previously recognized, however, a ratio exists and the anterior pretibials have a substantially smaller moment than the posterior triceps surae. Furthermore, many of assignees earlier patents, U.S. Pat. Nos. 7,507,259, 7,410, 503, and 7,611,543 have taught the utilization of spring elements which are positioned posterior in a calf shank/leg member. The addition of at least a resilient spring element not only functions as an artificial muscle but adds resilient mass to the system; any increase in prosthetic resilient mass that replicates human function will improve prosthetic and orthotic function.

Figure 60:
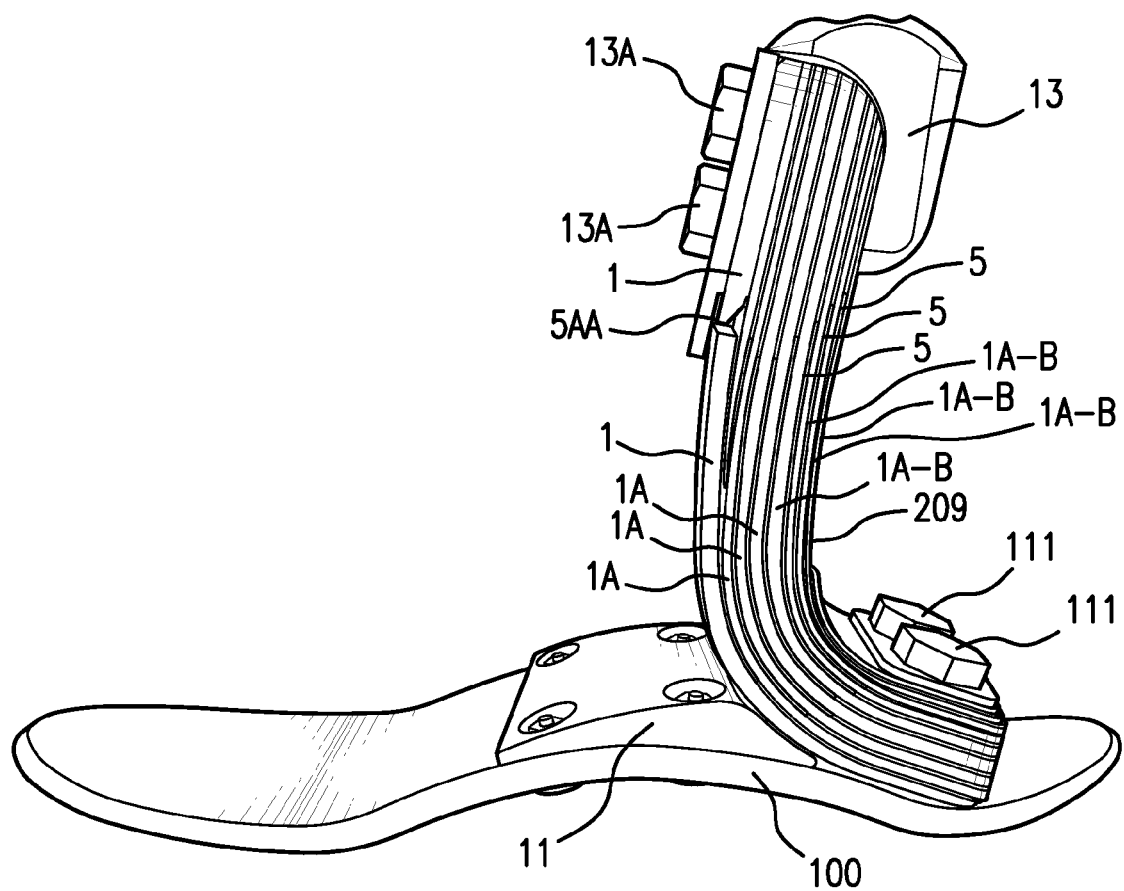
FIG. 60 is a side view of another embodiment of a prosthesis showing a resilient calf shank/leg member with at least a plurality of sagittally oriented sections/struts with at least a portion removed from at least a section/strut located between adjacent sections forming a space or void between the sections.
Figure 62:
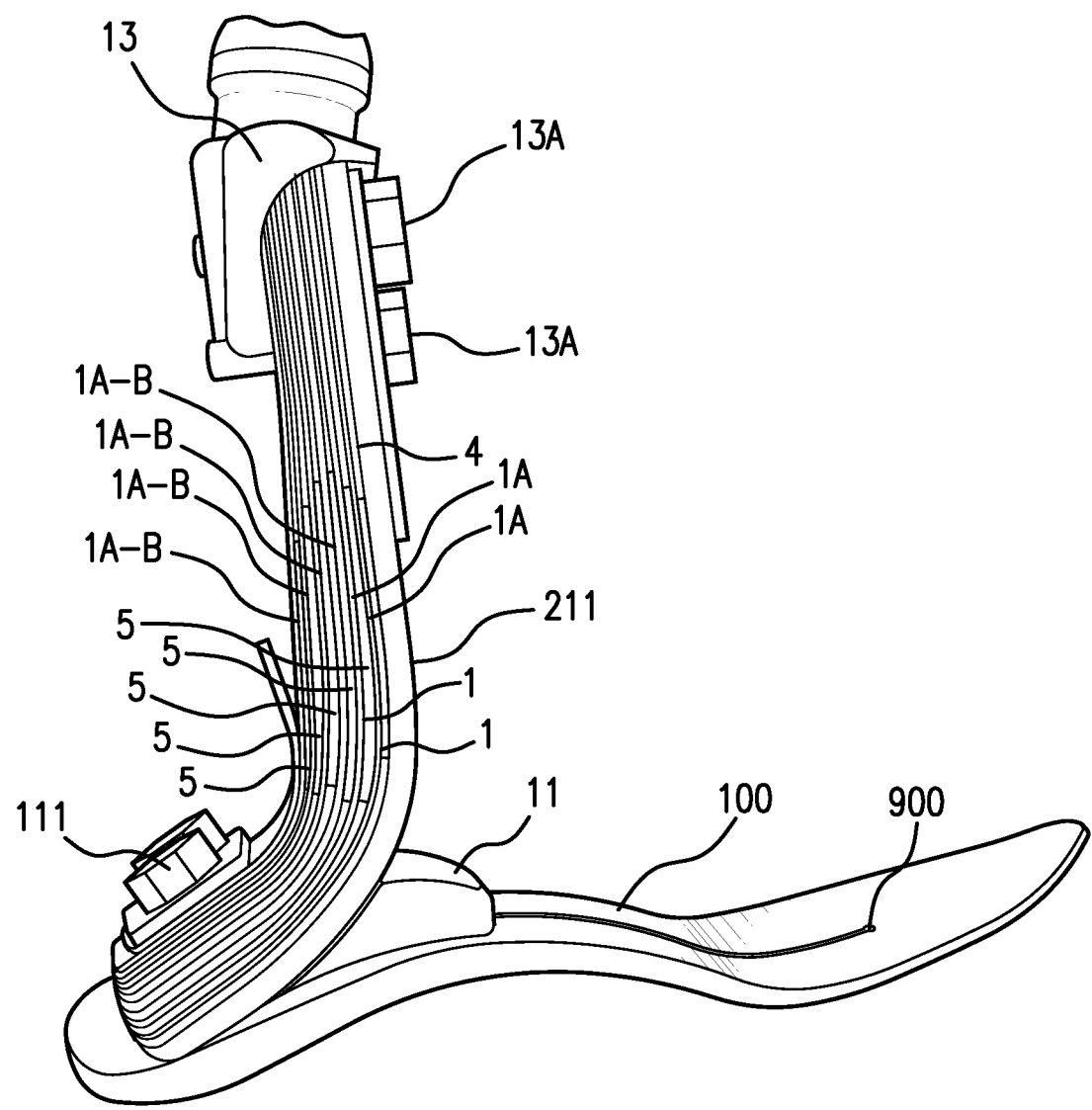
FIG. 62 is a side view of the prosthetic system under toe loading thereby showing the shank/leg with multiple sections/struts being expanded without experiencing failure from interlaminate shear.

The multiple sections/struts of the shank/leg members as shown in FIGS. 38, 40, 54, 56, 60, and 62 incorporate these types of posterior spring elements 1A-B and as a consequence in response to amputee gait force the member will compress and expand. In loading response phase of the gait, all the sections/struts 1, 1A, 1A-B compress and this compression replicates human ankle joint plantarflexion. This strut compression is augmented by two anterior sections/struts 1 as shown in FIGS. 38 and 60 because these two struts have a gap 5AA between their ends. This gap, which extends fully across the width of the shank sections, increases in length in response to loading response gait force and as a consequence all the struts compress thereby replicating ankle joint plantarflexion. Since the two anterior struts are not solid members, which are they have an intermediate gap between their ends 5A. A compression of these members is resisted less than if the two anterior struts were solid, e.g. part of a single section/strut which extended continuously the length of the shank between the upper and lower ends as sections 1A and 1A-B. It has been taught, in assignees previous patents, that compression of a resilient member is less resisted than expansion. Furthermore, the compression of the sections/struts stores elastic kinetic energy which is subsequently released causing the proximal end of the shank/leg member to move anterior longitudinally. In midstance phase of gait, the prosthetic system is in a neutral state with the sections/struts neither compressed nor expanded. However, in the midstance to late midstance phase of the amputee gait, the ground reaction force moves forward of the shank/leg member which causes all the struts 1, 1A, 1A-B to expand (i.e. lengthen), most specifically see FIG. 62, 1A-B. This expansion is resisted more than compression. This expansion simulates ankle joint dorsiflextion with the proximal end of the member moving anterior longitudinally. During this phase of gait, the prosthetic system is storing elastic kinetic energy. Elastic kinetic energy storage is enhanced by the number of (sagittally oriented) resilient sections/struts 1, 1A, 1A-B, nine total, as shown in FIGS. 38, 60, and 62. Furthermore, the expansion of the posterior four struts 1A-B are performing the function of a resilient posterior shank/leg artificial muscle device, see FIGS. 32, 114; FIG. 35, 123; FIG. 36, 123; FIG. 42, 199; FIG. 43, 299; FIG. 44, 299; FIG. 45, 310; FIG. 46, 320. FIG. 49, 350; FIG. 50, 360; FIG. 51, 370; and FIG. 52, 380, for example.

This design concept has been disclosed in many of assignee's previous patents. Dr. Perry reports in the aforementioned book that human ankle joint dorsiflexion (approximately 10 degrees) in the midstance to late midstance phase of gait is derived by the posterior triceps surae muscle group isometrically contracting so the Achilles tendon, which is the largest spring in the human body, can store elastic kinetic energy. Perry states "that the last five degrees of ankle dorsiflexion motion functions to load the Achilles tendon with elastic kinetic energy." As heel rise occurs in late midstance phase of the gait i.e. pre-swing phase of gait, the human and prosthetic ankle plantarflex thereby causing the ankle joint area to move upward and forward. Therefore, the expanded sections/struts extending in the longitudinal direction of the shank, which have stored kinetic energy release their stored kinetic energy in a plantarflexion burst of kinetic power and wherein these sections/struts compress back to their resting state. Prosthetically, the importance of an anterior facing convexly curved ankle joint area is paramount in replicating the human ankle joint's $1^{st}$ class lever status, wherein open kinetic chain motion patterns the toe moves vertically upward and horizontally forward and the heel moves vertically upward and horizontally posterior. However, in closed kinetic chain motion analysis, the toe and heel are not moving because of the ground. As a consequence, ankle motion is the source of kinetic motion and this motion can be either translational or rotational. In closed kinetic chain, with the foot on the ground, analysis shows the ankle joint/area moves in an opposite direction to open kinetic chain toe and heel motions. Therefore, in gait, closed kinetic chain ankle joint/area motions are: in loading response; the translational motion is horizontally forward and vertically downward; the rotational motion is plantarflexion. Once the foot has plantarflexed and foot flat has been achieved, the ankle joint/area dorsiflexes into midstance; there is not any translational motion only rotational dorsifelxion. In the midstance to late midstance phase of gait, there is no translational motion only rotational dorsifelxion motion; as heel rise occurs in late midstance pre-swing phase of gait; the ankle joint/area translational motion is vertically upward and horizontally forward and the rotational motion is plantarflexion. This motion pattern is counter intuitive because closed kinetic chain ankle motion is supposed to be in an opposite direction to open kinetic chain heel and toe motion. But a simple explanation will provide the solution, closed kinetic chain ankle motion represents resisted ankle motion; therefore, if open kinetic chain toe motion is vertically upward and horizontally forward, then ankle joint/area resisted motion is vertically downward and horizontally posterior, which it is.

Figure 11:
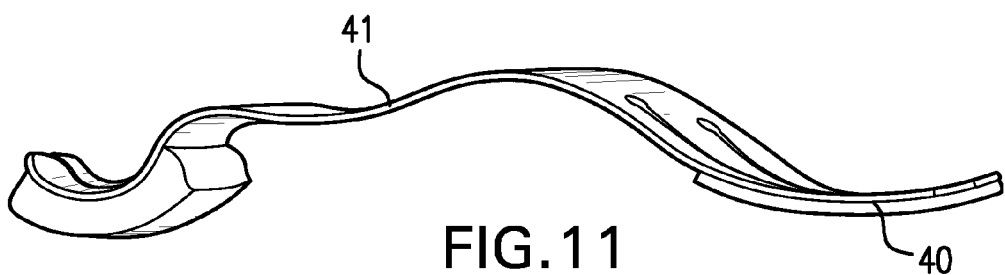
FIG. 11 is a further variation of foot keel for the prosthetic foot of the invention for a Syme amputee, the foot keel providing the prosthetic foot with high low dynamic response characteristics as well as biplaner motion capabilities.
Figure 12:
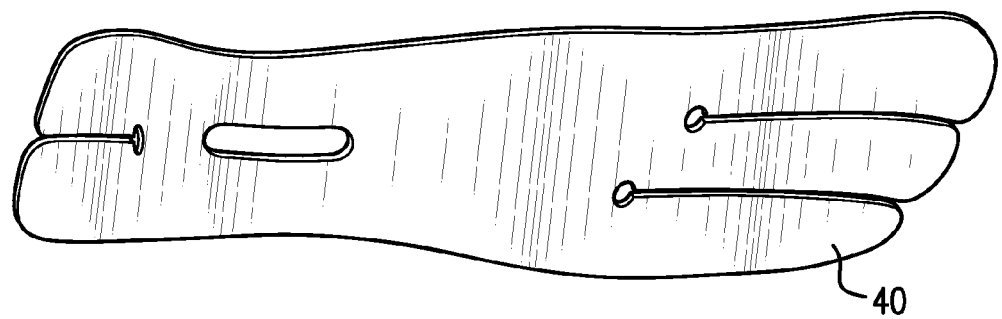
FIG. 12 is a top view of the foot keel of FIG. 11.
Figure 61A:
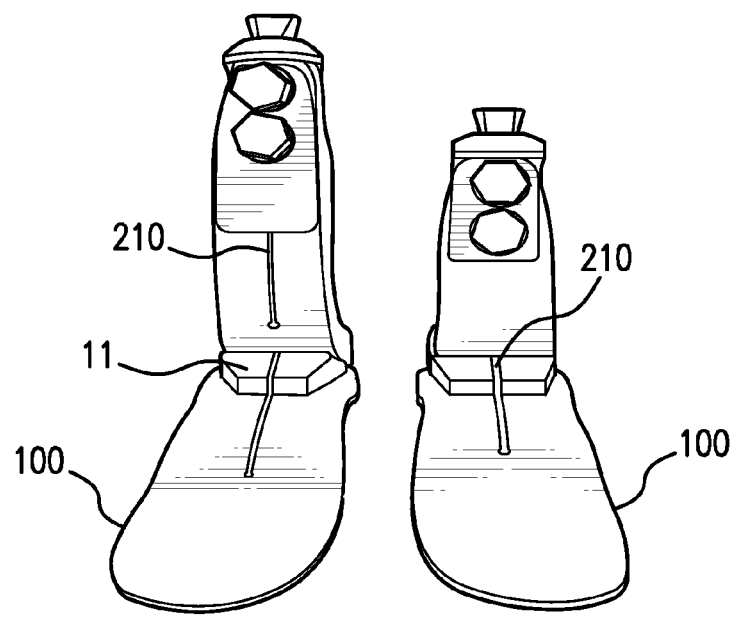
FIG. 61A shows an anterior view of a tall and short prosthetic foot, ankle, and shank system with a longitudinal slot/bifurcated mid foot, hind foot, and shank.
Figure 61B:
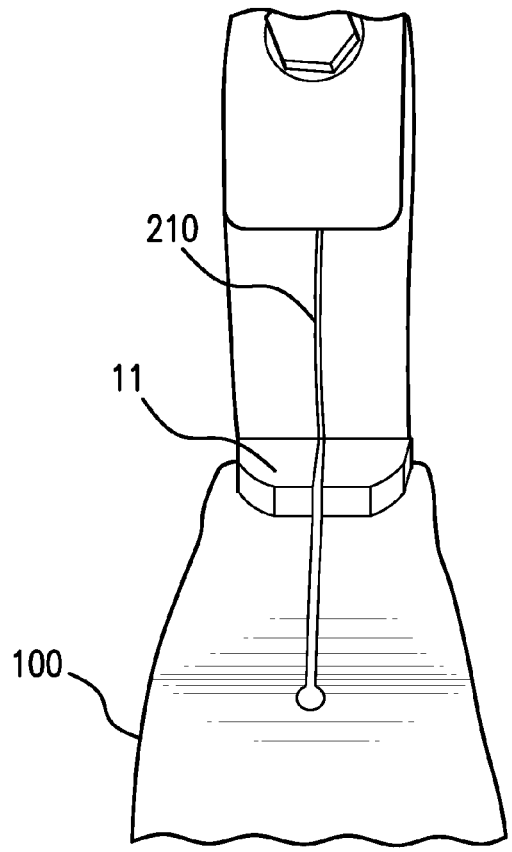
FIG. 61B shows an enlarged anterior view of the prosthetic foot, ankle, and shank system in FIG. 61A with a forefoot expansion joint hole whereby an expansion slot/bifurcation splits the foot keels mid foot, hind foot, and foot coupler in their entirety, the shank being bifurcated in its distal two thirds.
Figure 61C:
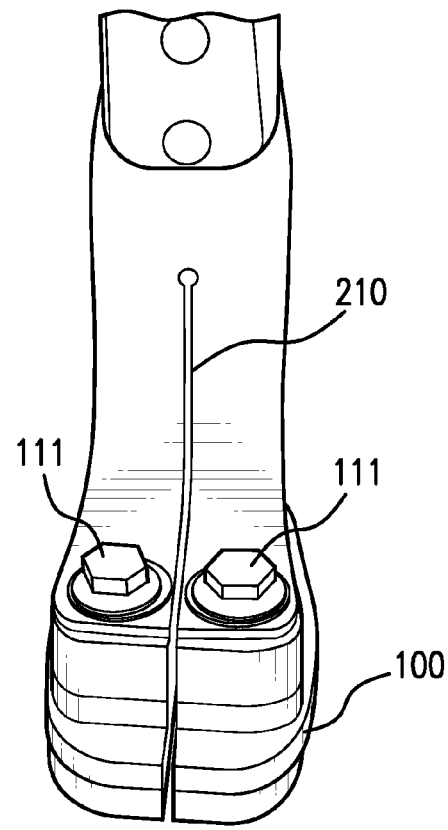
FIG. 61C shows a posterior view of FIGS. 61A and 61B wherein the shank has an expansion joint hole and an expansion split/bifurcation extending downwardly from the expansion hole thereby splitting the shank, keel coupler and keel into at least a plurality of longitudinally extending struts.

The monolithically formed multi-strutted resilient shank/leg member resistance to dorsifelxion in midstance to late midstance phase of gait is enhanced by the coupling element riser portion, see FIG. 38, 11; FIG. 41A, 11A; FIG. 41B, 11B; FIGS. 47B-47C, 11; FIGS. 48A-48C, 11; FIG. 49, 11; FIG. 61, 11; and FIG. 61B, 11 for example. As disclosed herein and in assignees previous patents, the coupling element 11 includes a dorsiflexion limiting riser portion in the midstance to late midstance dorsiflexion phase of gait. The distal anterior surface of the shank/leg member engages the riser which further increases the ankle joints dorsiflexion moment. The riser portion can be made in different thicknesses, see FIGS. 41A and 41B, 11A and 11B. A thicker riser portion, FIG. 41A, 11A, is utilized to accommodate higher heel shoes. The thicker riser accommodates ⅝" to 1¼" heel heights. The thinner riser in FIG. 41B, 11B accommodates flat to ⅝" heel heights.

Any of the previously disclosed foot keels can be utilized with the monolithically formed multi-strutted resilient member because they are designed with a hindfoot, midfoot, and forefoot wherein the midfoot has a raised longitudinal arch area. However, even a flat non-curvilinear foot keel would work with a coupling element 11 with riser portion and the resilient multi-strutted shank/leg member of the present invention. Referring now to FIGS. 41A and 41B, the foot keel may be further divided into three areas for reference: (1) the forefoot portion 101; (2) the midfoot portion 102; and (3) the hindfoot portion 103. In the preferred embodiment, see FIGS. 41A and 41B, the foot keel is constructed of carbon fiber. However, any of several different light weight materials may be used. In the preferred embodiment both the fore- and hindfoot areas, 101 and 103, are tapered in decreasing thickness at their ends which curve upwards or proximally. The midfoot portion 102 of the foot keel 100 also curves upward or proximally in an arch and incorporates toward its posterior end a fastening arrangement which attaches the multi-strutted shank/leg member directly to the foot keel; see FIGS. 54, 106 and 111. In the FIG. 54 embodiment this is accomplished through two bolts 111 which extend through a posterior end of the shank and the keel in connection with a single proximally placed metal washer 106. However, the fastening arrangement may take any number of alternative forms or designs. As shown in FIGS. 41A, B, and FIG. 61B, a coupling element 11 with riser portion is utilized between the calf shank/leg member 210 and the foot keel 100. The skilled artisan will recognize that a foot keel's curvilinear form could create the riser's proximal surface shape thereby eliminating the coupling element 11 and directly connecting the shank on the foot keel. Further, in the embodiment of FIGS. 41A and 41B, 100, the foot keel is relatively thicker in the midfoot 102 portion than in the fore- and hindfoot portions, 101 and 103, and tapers to a decreasing thickness toward both the forefoot and hindfoot. One function of these tapered sections, among others, is to optimize the strength, flexibility, and displacement of the foot keel during use. More precisely, the thinner toe and heel design facilitates deflection thereby providing a softer feel to the user which would not be found in a foot keel where thickness is relatively equal throughout. In another form of the invention, various portions of the keel may incorporate portions of uniform or varying thickness, depending on the flex characteristics desired. As shown in FIGS. 54-56, 58, and 59 towards its anterior end, the midfoot portion of the foot keel incorporates a single metal bolt 104 with its head exposed on the proximal surface of the keel. As discussed in further detail below, this bolt may be used in connection with the shank during loading of the prosthesis in particular embodiments. Other embodiments may omit the bolt.

Figure 55:
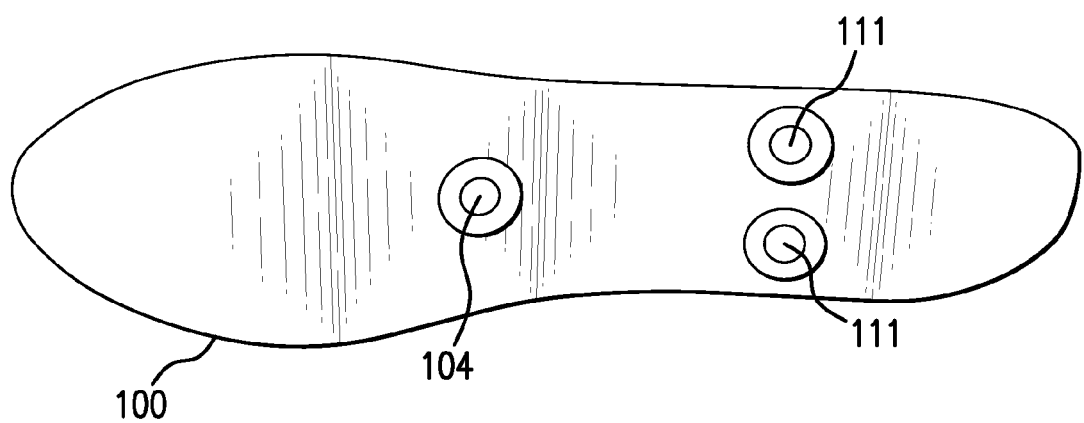
FIG. 55 is a bottom view of the foot keel from the prosthesis of FIG. 54.
Figure 56:
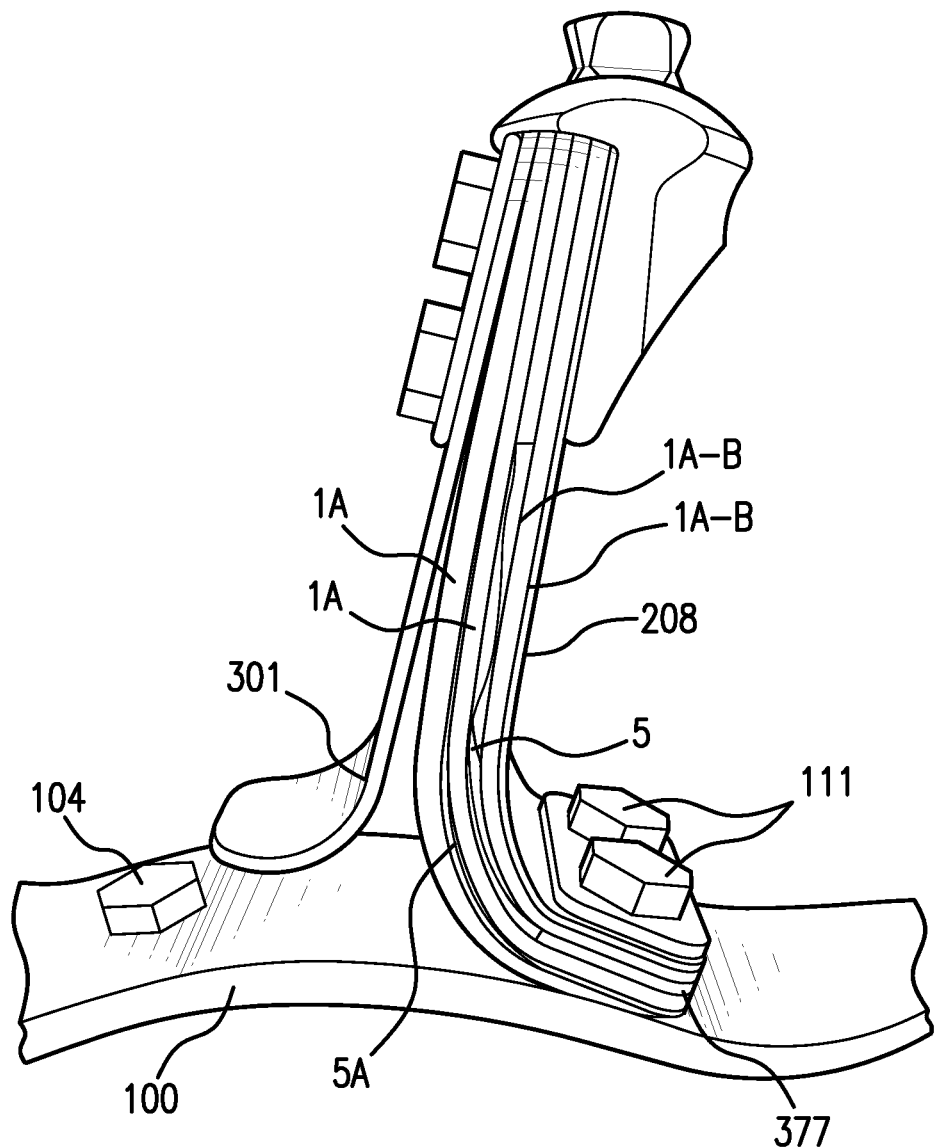
FIG. 56 is a close up view of the prosthesis in FIG. 54 showing a resilient calf shank/leg member with at least a plurality of sagittally oriented sections/struts and with at least an intermediate gap between adjacent sections.
Figure 57:
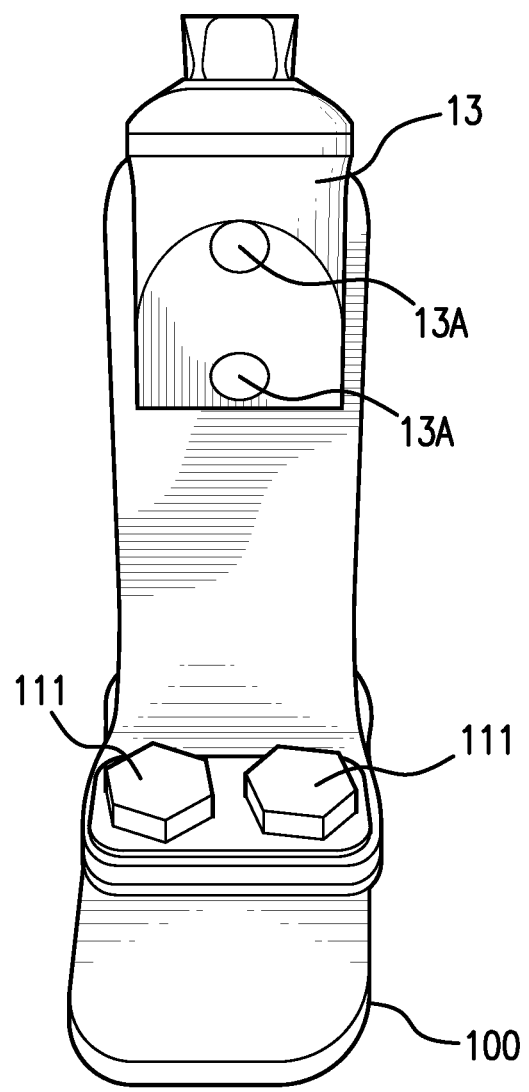
FIG. 57 is a posterior view of the prosthesis as shown in FIG. 54.
Figure 58:
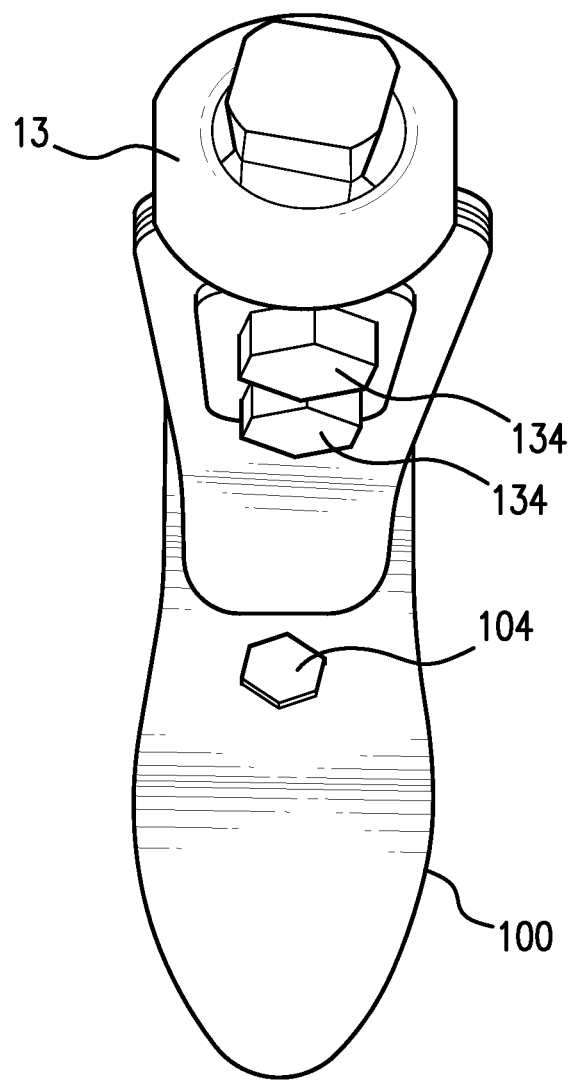
FIG. 58 is an anterior-proximal view of the prosthesis as shown in FIG. 54.
Figure 59:
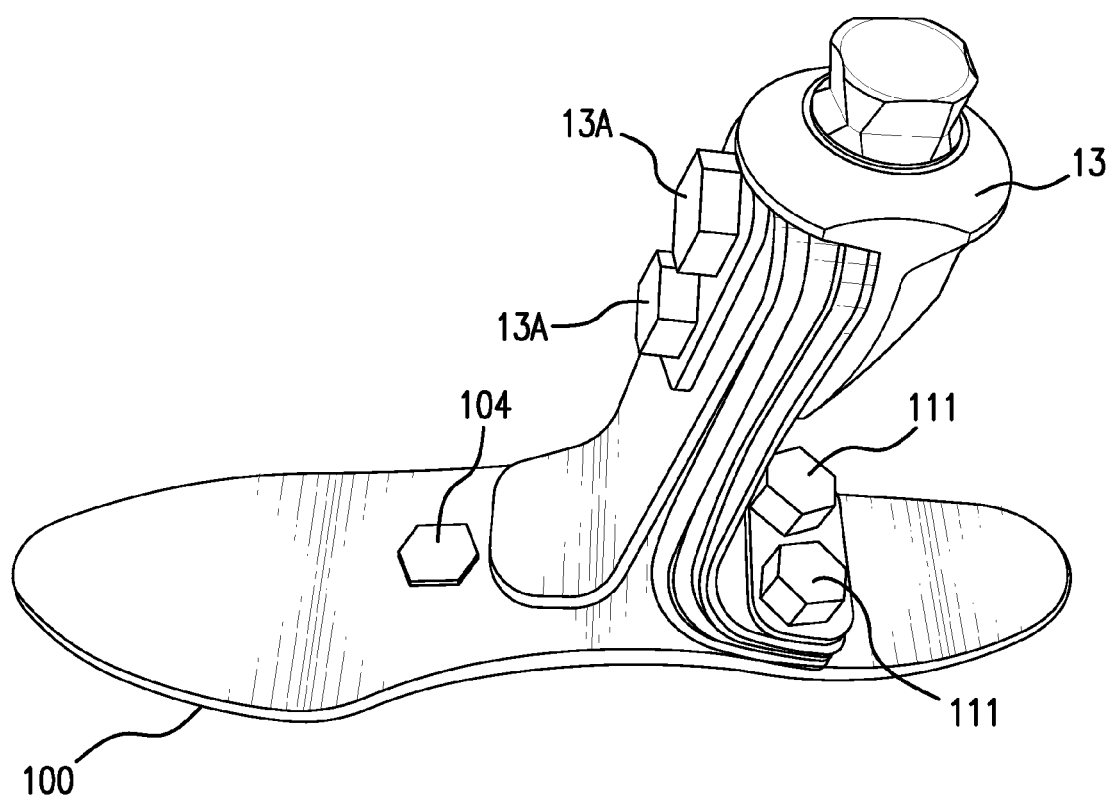
FIG. 59 is a side-proximal view of the prosthesis as shown in FIG. 54.

Referring now to FIG. 55, the distal or bottom surface of one embodiment of the invention is shown, with the single bolt toward the anterior end of the keel 104 and the two bolts fastening the shank to the keel 111. FIG. 56 shows an expanded side view of the multi-strutted shank/leg member 208 in the embodiment. The shank includes multiple sections/struts 1A and 1A-B, which connect to the foot keel via fastener 111, and an anterior facing strut which will be called an anterior load transfer spring 301. The embodiment incorporates a plurality of sagittally oriented sections/struts which together make an anterior facing convexly curved-shaped shank/leg member that includes a single anterior load transfer spring 301 J-shaped strut. In the preferred embodiment, the shank/leg sections/struts and anterior load transfer spring are constructed of carbon fiber. However, any of several different light weight materials may be used.

In the embodiment of the invention, shown in FIG. 56, the distal end of the anterior load transfer spring 301 is positioned above and does not normally contact the foot keel 100 when a load not exceeding a certain predetermined threshold is placed on the prosthesis in the unloaded position; however, the spring 301 may come into contact with the foot keel 100 or the single bolt on the anterior foot keel 104, or both of them during loading which exceeds the predetermined threshold. When in contact with the anterior load transfer spring 301 and the single bolt 104, or the foot keel 100 in connection with the single bolt 104 act as a stop to engage or facilitate loading upon the anterior load spring 301. In various other embodiments, the anterior load spring may contact the foot keel 100, the single bolt 104 or the anterior end of the foot keel 100, or other stop in an unloaded position or without exceeding the predetermined threshold. In certain other embodiments, a slot may be made in the foot keel to allow variation in the positioning of a stop on the anterior end of the keel and to allow the strut to engage the top at different loads. Ultimately, many different configurations which allow for a wide range of loading and support scenarios are possible.

Figure 40:
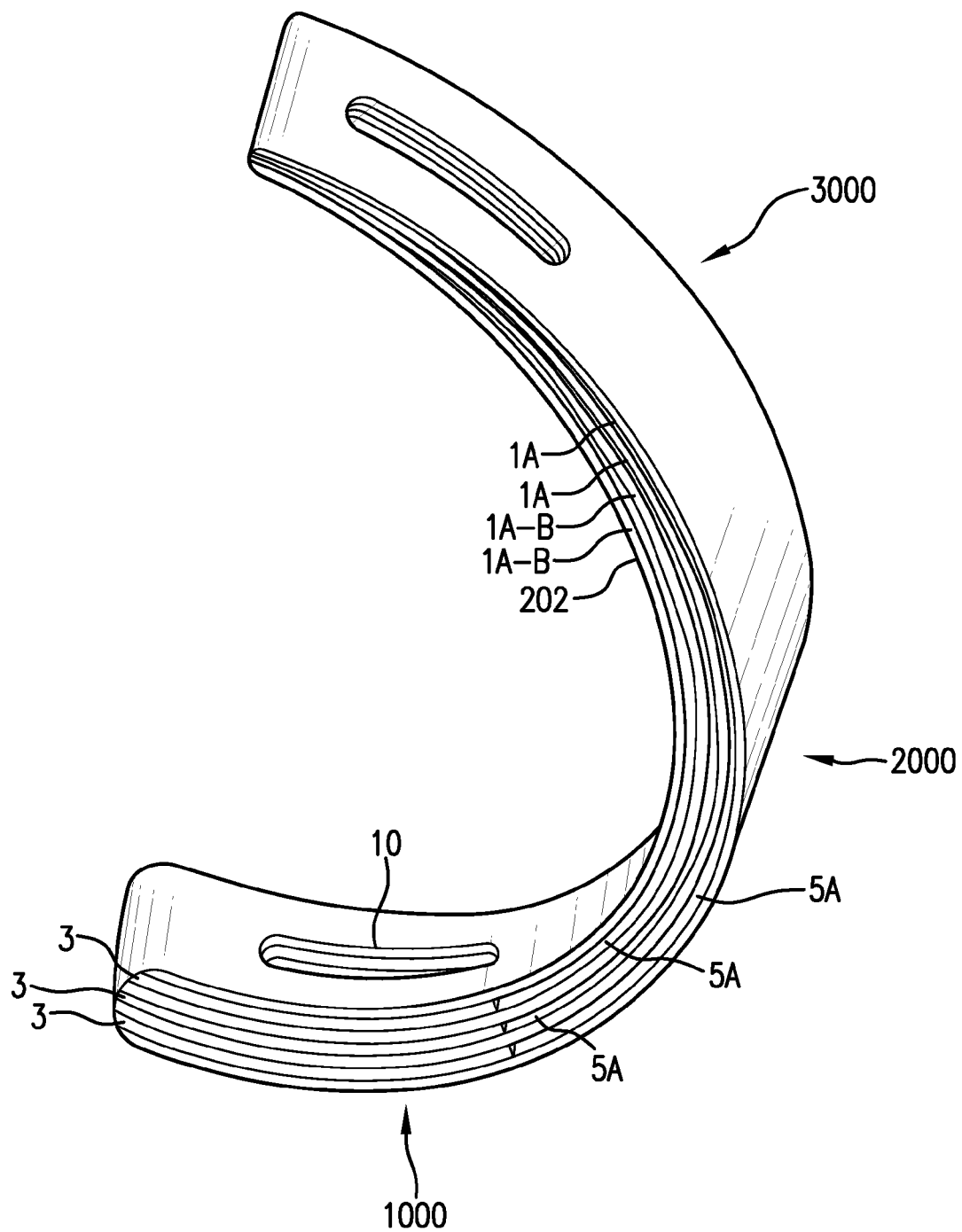
FIG. 40 is a perspective view of a still further variation of the resilient shank/leg member wherein the shank is parabolic in shape and has multiple sections with gaps there between, the gaps being larger distally than they are proximally.
Figure 54:
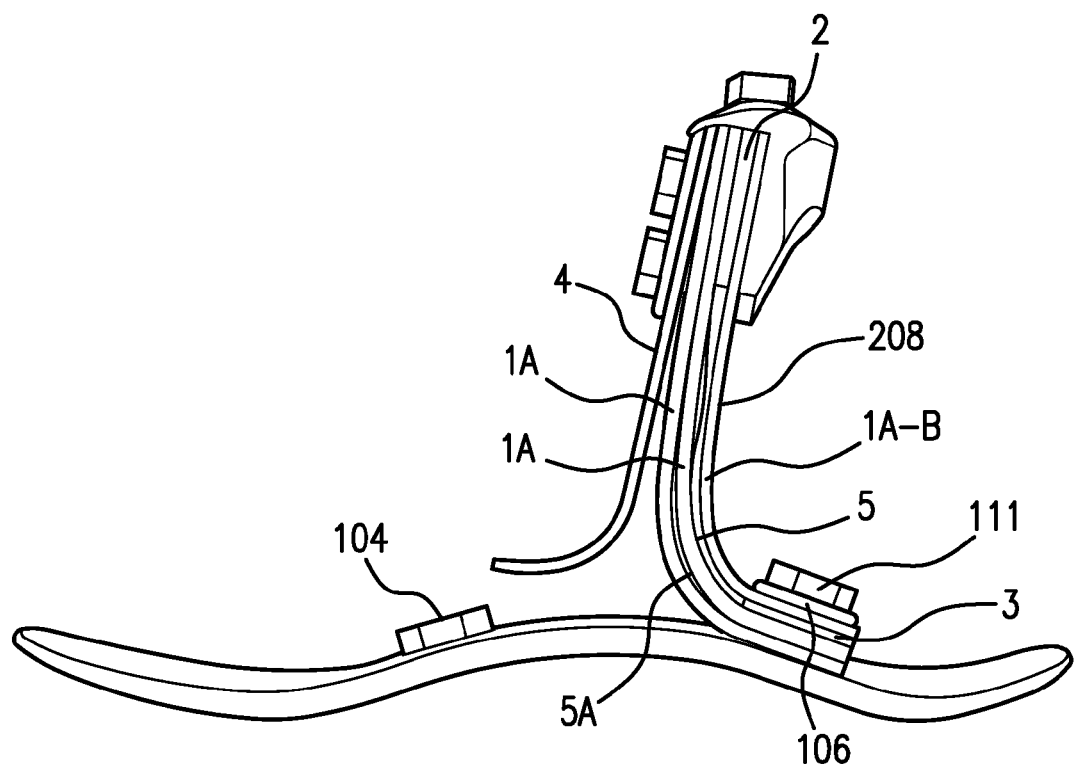
FIG. 54 is a side view of another embodiment of the prosthesis.

FIGS. 37, 38, 54, 56, 60, and 62 show a monolithically formed resilient multi-strutted member with intermediate gaps or spaces 5 created by removing material in selected sections/struts intermediate its ends/the ends of the shank. However, another gap type embodiment of the member would require selectively removing material proximally on a selected strut, wherein a distal portion of the selected strut remains, this is shown in FIGS. 40, 54, and 56 as 5A. In this embodiment, the intermediate gap/space between sections is not symmetrical through its proximal, middle, and distal ends; it is wider distally and tapers to be non-existent at the proximal portion. The advantage this produces is that motion in the monolithically formed multi-strutted resilient member is concentrated to be more distally oriented. This could be advantageous in generating more ankle joint/area kinetic power because ankle joint/area kinetic power is derived by multiplying ankle moments times ankle angular velocity. Therefore, any mechanical structure change that concentrates angular change at the ankle joint/area would increase angular velocity which would increase kinetic power.

Figure 53:
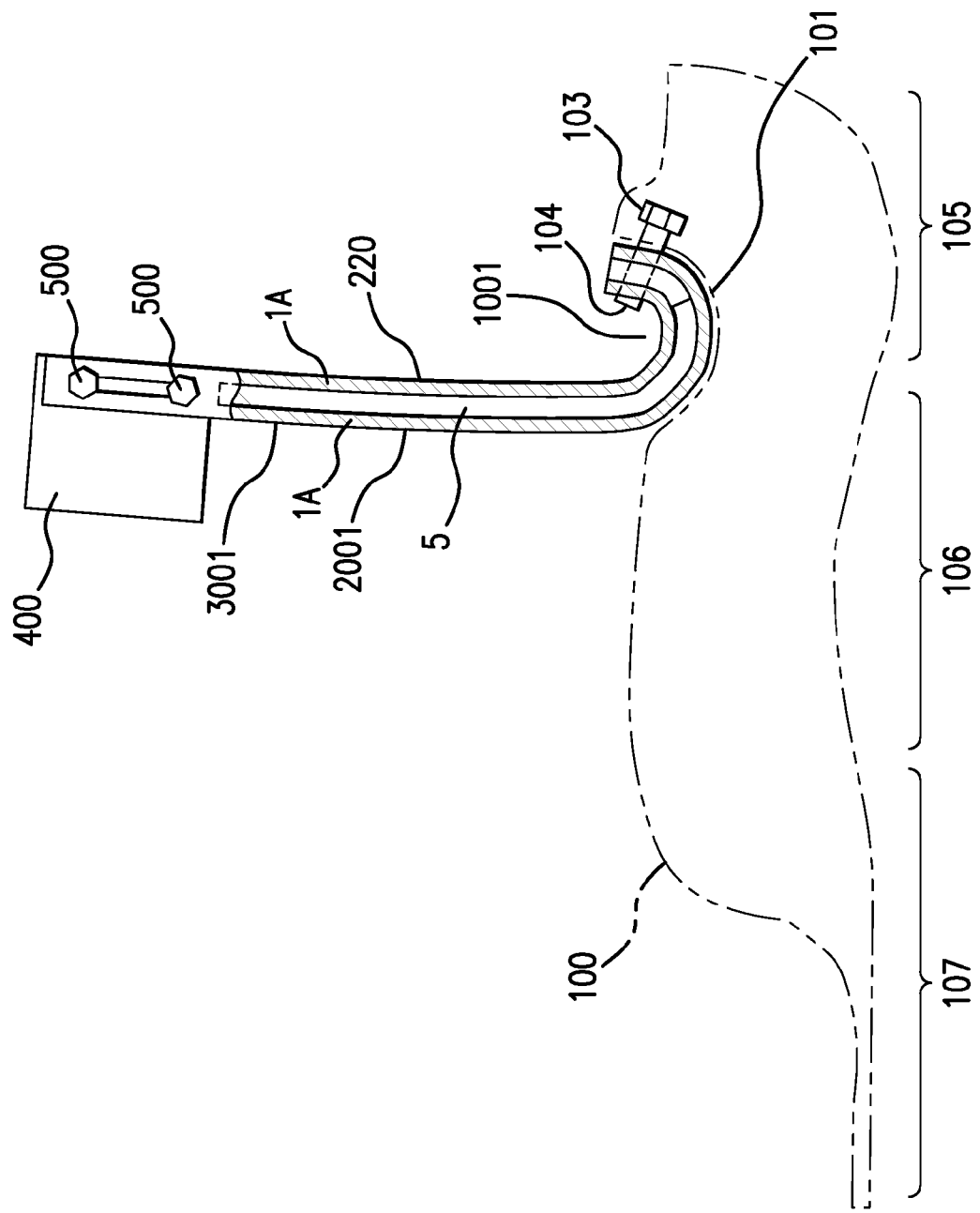
FIG. 53 is a side view of an orthotic embodiment wherein the orthotic ankle joint is made in at least a plurality of sagittally oriented sections/struts with an intermediate gap between at least two of said struts.

FIG. 53 shows a side view of an orthotic foot plate 100 which could be made in plastic, or carbon composite, or any other suitable material known in the orthotics industry. The foot plate 100 has a hindfoot area 105, a midfoot area 106, and a forefoot area 107. Coupled to a proximal surface 101 of the orthotic foot plate is an orthotic resilient ankle joint member 220. The ankle joint member has a substantially longer vertical member 3001 and a substantially shorter horizontal member 1001. The member 220 can be made of plastic, composites, alloys, or other suitable materials. The member 220 has at least a plurality of sagittally oriented sections/struts 1A, and at least an intermediate gap 5 located between struts 1A. The gap 5 was created by removing at least a proximal portion of an intermediate section/strut which is sandwiched between the at least two struts 1A. Furthermore, the member is coupled to a proximal surface of the foot plate which includes a mounting shelf 101 and a releasable fastener 103. The fastener does not have to be releasable because a rivet or other permanent fasteners will work. The fastener 103 goes through a hole in the posterior portion of the member and is secured by a nut 104. Proximally, the resilient multi-strutted orthotic ankle joint is coupled to an anterior or posterior calf cuff. An anterior calf cuff is shown in FIG. 53 as 400. This coupling/leg attachment can be rigid by using two rigid fasteners per side. In another embodiment not shown, the calf cuff could be coupled on both sides with a rotatable fastener thereby allowing the calf cuff to tilt in a sagittal plane.

The function of the resilient multi-strutted ankle joint is substantially similar to the function of our resilient prosthetic multi-strutted calf shank/leg member. In loading response phase of the orthotic gait, the member compresses/plantarflexes to store energy and once foot flat is achieved the stored compression energy is released thereby assisting forward tibial progression to midstance. In the midstance to late midstance phase of the gait, the member 220 expands/dorsiflexes thereby storing elastic kinetic energy. The mounting shelf 101 has an anterior edge that acts the same as the prosthetic coupler element 11 riser portion which helps to create greater resistance to ankle joint dorsifelxion moment. In the preswing phase of gait, the member releases its stored elastic kinetic energy in an elastic burst of energy by plantarflexing back to neutral. This plantarflexion functions to accelerate the foot ankle and leg horizontally forward and vertical upward.

Manufacturing Preferred Embodiments of Multi-strutted Composite Structures

Traditional monolithically formed composite structures include a fiber and a resin. The fibers can be made of kevlar, graphite, carbon, boron, rayon, nylon, fiberglass, other plastics, or other polymer materials. Graphite nano tubes may also be used. The resin or binding material may include thermosetting resin systems, epoxies, ceramics, or thermoplastics. The fibers are impregnated with resin to form a composite material. These traditional monolithically formed structures are well known in the art of prosthetics and orthotics. These structures are made with multiple layers of material bound together with resins. These materials are usually placed in forms under heat and pressure, where they are formed, and wherein each successive layer of material becomes mechanically bonded to the next layer. Many layers of materials can be bound together to form prosthetic and orthotic components. This method of manufacturing creates a monolithically formed structure which in most cases is a single solid resilient structure. The flexibility of these structures can be improved by removing material intermediate theirs ends as illustrated and described therein. This removal of material creates a gap or space or void 5 as shown in FIGS. 37, 38, 40, and 56 between two adjacent sections/struts and this gap creates a plurality of (sagittally oriented) struts. These sagittally oriented struts 1, 1A, 1A-B have many layers of material mechanically bonded together to form each strut. FIGS. 38, 39, 60, and 62 shows another embodiment wherein a multiplicity of sagittally oriented struts 1, 1A, and 1A-B have been created. These sagittally oriented struts 1, 1A, 1A-B may or may not vary in anterior/posterior thickness; however, they are usually wider in width than they are thick anterior to posterior. The anterior/posterior thickness of each (sagittally oriented) strut is based on how many successive layers of material are utilized wherein more layers of the same material creates a thicker strut, for example.

Manufacturing the prosthetic and orthotic components as shown in FIGS. 37-40, 53, 56, 60, and 62 requires non-traditional techniques. The method of manufacturing disclosed herein to create a multi-strutted prosthetic and/or orthotic component according to the invention exploits the concept disclosed in US Publication No. 2004//0209716A1 for making a composite baseball bat. In this patent publication, a composite baseball bat is made with a plurality of circular elements. The disclosed method is changed in accordance with the invention for making prosthetics since the method of manufacturing cylindrical baseball bats disclosed therein would not work for the components of the present invention.

To cost effectively manufacture a monolithically formed resilient composite structure with a plurality of sagittally oriented struts with at least an intermediate gap between the struts extending longitudinally in the composite structure in accordance with the invention, required the use of a release element film. This film is usually a polypropylene, and/or nylon film but other materials could be utilized, without varying from the teachings of this patent. These release films are readily available from composite retailers. This film provides a release layer; a release layer is further defined as a film layer between adjacent layers of material that prevents mechanical bonding from occurring. In our manufacturing method, this release layer film is selectively placed between adjacent layers of material. In the molding process, the release layer film between adjacent layers of material functions to keep the adjacent layers of material from mechanically bonding to each other. This lack of mechanical bond allows us to separate the adjacent members see FIGS. 39A and 39B. The benefit of being able to separate adjacent strut member/elements allows us to disassemble the monolithically formed structure into several individual elements modifying some resilient elements into resilient spacer element. As an example, during manufacturing the ankle and shanks in FIGS. 37A, 37B, and 38 are formed as a single monolithic unit where a release film is placed between sections/struts. The release film allows the layers to be separated after molding to form the monolithic shank member structure due to the lack of mechanical bonding imposed by the addition of the release film. The resulting structure is comprised of multiple sections/struts.

The ankles and shanks in FIGS. 37A, 37B, and 38 are comprised of three and fifteen sections/struts, respectively. Once these sections are disassembled, selective sections/struts are chosen to have an intermediate section between their ends removed/eliminated (this creates void/spaced gap type 5) or a proximal portion of a selected section/strut is removed thereby creating a void/space gap style 5A as shown in FIGS. 40 and 56 for example. This removal/elimination of material is done by grinding or cutting. The net effect of removing/eliminating this intermediate portion of material between the ends of the sections/struts and the ends of the shank is to create an intermediate gap/space/void between two adjacent struts, as shown in FIGS. 37A, 37B, and 38, gap 5, and/or an intermediate gap between the same proximal and distal element as shown by FIGS. 38 and 60 gap, 5AA. Each of these gap types 5, 5A, and 5AA may be utilized in the monolithically formed component. Furthermore, as discussed in assignees U.S. provisional application No. 61/277,414, these gap types could be back filled with silicone rubber or any number of other softer materials may be between or among the plurality of sagittally oriented sections/struts. Other manufacturing techniques and materials could be utilized to manufacture the multi-strutted calf shank/leg component. For example, the calf shank/leg member could be cut out of a solid member and the gap types 5 and 5A could be formed by cutting, grinding, or machining away material.

The primary benefit of removing material intermediate the ends, of a selective strut, is to create a gap between the adjacent struts thereby creating at least a plurality of sagittally oriented struts with at least a gap between said struts. Assignee's research shows that a plurality of resilient sections/struts are much more flexible than a similar single solid resilient member. An analogy can be drawn to a phone book. A phone book with its multiplicity of pages is more flexible than a solid block of wood. Similarly, a plurality of resilient struts, with at least a gap between adjacent sections/struts, is more flexible than a resilient single solid member with the same combined mass.

The posterior elongated struts 1A-B of the posterior calf device could also have a form other than a J-shaped spring. They could be a curvilinear form. For example, a coiled spring could be used as an elastic elongated member between upper and lower portions of the prosthesis. Further, reasonable variations and modifications are possible in the component parts and/or arrangements of the subject combination arrangement within the scope of the foregoing disclosure, the drawings, and the appended claims without departing from the spirit of the invention. In addition to variations and modifications in the component parts and/or arrangements, alternative uses will also be apparent to those skilled in the art.

This concludes the description of the example embodiments. Although the present invention has been described with reference to a number of illustrative embodiments, it should be understood that numerous other modifications and embodiments can be devised by those skilled in the art that will fall within the spirit and scope of the principles of this invention. For example, the lower end of the calf shank in the prosthetic foot of the invention is not limited to a parabola shape or a spiral shape but can be hyperbolic or otherwise downward convexly, curvilinearly configured to produce the desired motion outcomes of the foot when connected to the foot keel to form the ankle shank/leg areas of the foot, ankle and shank. The features of the various embodiments including the materials for construction could also be used with one another. For example, the posterior calf devices of the embodiments of FIGS. 32-44 could be used on other prosthesis of the invention including those disclosed in the embodiments of FIGS. 1-31.

We claim:

1. A method of making a resilient prosthetic component comprising the step of:
    monolithically forming a plurality of resilient elements utilizing at least one part form, heat and pressure,
    disassembling the formed; resilient elements,
    removing material from an intermediate portion of at least one of the formed resilient elements to form at least one gap, void or space therein,
    assembling the formed elements to form the resilient prosthetic component wherein the gap, void or space therein reduces inter-laminar shear forces in the component.

2. The method according to claim 1, wherein the material is removed by cutting.

3. The method according to claim 1, wherein the assembling includes connecting the formed resilient elements together at ends of the component.

4. The method according to claim 1, wherein the prosthetic component is a resilient leg member for a lower extremity prosthesis.

* * * * *